US012746018B2

(12) United States Patent
Komistek et al.

(10) Patent No.: US 12,746,018 B2
(45) Date of Patent: Sep. 29, 2026

(54) METHODS AND APPARATUS FOR MID-FLEXION BALANCING DURING KNEE ARTHROPLASTY

(71) Applicant: Knimble Designs, Inc., Menlo Park, CA (US)

(72) Inventors: Richard David Komistek, Knoxville, TN (US); Thomas Jefferson Blumenfeld, Davis, CA (US); Derek F. Amanatullah, Menlo Park, CA (US); Michael LaCour, Knoxville, TN (US)

(73) Assignee: Knimble Designs, Inc., Menlo Park, CA (US)

( * ) Notice: Subject to any disclaimer, the term of this patent is extended or adjusted under 35 U.S.C. 154(b) by 0 days.

(21) Appl. No.: 19/263,224

(22) Filed: Jul. 8, 2025

(65) Prior Publication Data

US 2025/0331869 A1 Oct. 30, 2025

Related U.S. Application Data

(60) Division of application No. 18/127,250, filed on Mar. 28, 2023, now Pat. No. 11,786,262, and a continuation of application No. 18/503,600, filed on Nov. 7, 2023, which is a division of application No. 18/242,612, filed on Sep. 6, 2023, now Pat. No. 11,849,960.

(51) Int. Cl.
*A61B 17/17* (2006.01)
*A61F 2/46* (2006.01)

(52) U.S. Cl.
CPC .......... *A61B 17/1764* (2013.01); *A61F 2/461* (2013.01)

(58) Field of Classification Search
CPC ............................ A61B 17/1764; A61F 2/461
See application file for complete search history.

(56) References Cited

U.S. PATENT DOCUMENTS

| | | | |
|---|---|---|---|
| 5,630,820 | A | 5/1997 | Todd |
| 5,688,280 | A | 11/1997 | Booth, Jr. |
| 5,800,438 | A | 9/1998 | Tuke |
| 7,367,984 | B2 | 5/2008 | Kulcinski |
| 11,701,097 | B2 | 7/2023 | Capote |

(Continued)

FOREIGN PATENT DOCUMENTS

| | | |
|---|---|---|
| WO | 2024206057 | 10/2024 |
| WO | 2025213055 | 10/2025 |

*Primary Examiner* — Sameh R Boles
(74) *Attorney, Agent, or Firm* — Dorton & Willis LLP; Ryan Willis

(57) ABSTRACT

Joint balancing methods and apparatus for arthroplasty procedures are disclosed. An example knee balancing jig may include a tibial placement guide configured for mounting to a tibial reference in a generally medial-lateral orientation in position generally anterior to a knee and/or at least one balancing assembly. The balancing assembly may include a vertical guide configured to releasably mount to the tibial placement guide in a generally inferior-superior orientation, at least one posteriorly extending paddle selectively vertically movable along the vertical guide, the paddle configured to selectively engage a distal femur and/or a proximal tibia, and/or at least one pin guide selectively vertically movable along the vertical guide, the at least one pin guide comprising at least one opening configured to receive at least one of a drill bit and a bone pin therethrough.

29 Claims, 45 Drawing Sheets

(56) References Cited

U.S. PATENT DOCUMENTS

| | | | |
|---|---|---|---|
| 11,786,261 | B2 | 10/2023 | Nielsen et al. |
| 11,786,262 | B1 | 10/2023 | Komistek |
| 11,812,978 | B2 | 11/2023 | Trabish et al. |
| 11,911,050 | B2 | 2/2024 | Amanatullah et al. |
| 2008/0195110 | A1 | 8/2008 | Plassy et al. |
| 2018/0085134 | A1 | 3/2018 | Uthgenannt |
| 2019/0358056 | A1 | 11/2019 | Lerat |
| 2020/0085420 | A1 | 3/2020 | Capote |
| 2020/0305942 | A1 | 10/2020 | Oden |
| 2021/0259713 | A1* | 8/2021 | Trabish .................. A61B 90/94 |
| 2022/0133338 | A1 | 5/2022 | Amanatullah et al. |
| 2022/0354512 | A1 | 11/2022 | Rock |
| 2023/0172600 | A1 | 6/2023 | Dumpe et al. |
| 2024/0342036 | A1 | 10/2024 | Walkington |

* cited by examiner

METHODS AND APPARATUS FOR MID-FLEXION BALANCING DURING KNEE ARTHROPLASTY

CROSS REFERENCE TO RELATED APPLICATIONS

This application is a continuation of U.S. Nonprovisional application Ser. No. 18/503,600, filed Nov. 7, 2023, and titled, “METHODS AND APPARATUS FOR MID-FLEXION BALANCING DURING KNEE ARTHROPLASTY,” which is a divisional of U.S. Nonprovisional application Ser. No. 18/242,612, filed Sep. 6, 2023, and titled, “METHODS AND APPARATUS FOR MID-FLEXION BALANCING DURING KNEE ARTHROPLASTY,” now U.S. Pat. No. 11,849,960, which is a divisional of U.S. Nonprovisional application Ser. No. 18/127,250, filed Mar. 28, 2023, and titled, “METHODS AND APPARATUS FOR MID-FLEXION BALANCING DURING KNEE ARTHROPLASTY,” now U.S. Pat. No. 11,786,262, the disclosure of each of which is incorporated by reference herein.

INTRODUCTION TO THE INVENTION

The present disclosure is directed to surgical equipment and methods and, more specifically, to surgical equipment for use in joint arthroplasty and associated methods for balancing joints other than at zero and ninety degrees of flexion.

Referencing FIG. 1, the present disclosure contemplates that, at full extension, a normal human knee joint includes the lateral and medial femoral condyles contacting the tibia plateau anterior of the anteroposterior midline, with the lateral femoral condyle contact being more anterior than the medial femoral condyle contact in full extension. As the knee joint is repositioned from full extension toward full flexion (approximately 160 degrees, which varies depending upon anatomical constraints and a person’s ability to flex their knee), the lateral femoral condyle contact with the tibial plateau moves posteriorly in a progressive manner until reaching approximately 120 degrees of flexion. After this amount of flexion is reached, the lateral femoral condyle rolls off of the tibia plateau and moves down the posterior aspect of the tibia a small amount. In contrast, the medial femoral condyle initially moves posteriorly from full extension to mid-flexion (ranging from 60-80 degrees), followed by moving anteriorly as the knee progressively flexes to full knee flexion. Accordingly, compared to the lateral femoral condyle, the medial femoral condyle remains more central on the tibial plateau throughout knee flexion, mainly due to the medial collateral ligament (MCL) as it resists too much posterior medial condyle motion. The present disclosure contemplates that, at times, some total knee arthroplasty (TKA) designs try to induce too much medial condyle rollback leading to the MCL become too tight and resisting weight-bearing knee flexion. The contact patterns exhibited by the medial and lateral femoral condyles lead to a fan-like motion pattern, where the lateral femoral condyle rotates around the medial femoral condyle in a non-pivoting pattern. As is indicative of the motion patterns of FIG. 1, movement of both medial and lateral femoral condyles across the flexion range of motion is progressive in nature and omits directional changes that are sudden and “jerky.”

The present disclosure contemplates that when structural changes occur in the contact surfaces of the knee joint, due to arthritis or degeneration, that the body cannot adequately repair, it may be time for a patient to consider total or partial knee arthroplasty. Knee arthroplasty involves a surgical procedure where contact surfaces of the knee joint are replaced with orthopedic implants, with partial knee arthroplasty replacing a portion of the contact surfaces, while total knee arthroplasty replaces all contact surfaces. Time honored concepts of total knee arthroplasty have yielded excellent survivorship outcomes at greater than 10-year follow-up both in single surgeon, institutional, and in large registry data. These concepts may include coronal alignment, resection of the distal femur, proximal tibia, and posterior femur, and balancing of the medial and lateral collateral ligaments.

With regards to FIGS. 2 and 3, the present disclosure contemplates that once the anterior cruciate ligament (ACL) is resected for posterior cruciate retaining (PCR) TKA surgery, the femoral condyle experiences very abnormal or paradoxical motion patterns where the kinematics are often opposite of the normal knee and the knee often experiences sliding with progressive knee flexion rather than rollback. FIG. 2 shows the lateral condyle motion pattern for five subjects with a PCR TKA and FIG. 3, the medial condyle for these subjects. These subjects are experiencing very erratic motion patterns opposite of the normal knee motion pattern. In a posterior cruciate retaining (PCR) TKA, the ACL is sacrificed while the posterior cruciate ligament (PCL) is left intact. Without the ACL, the PCL no longer has a counterbalancing force to ensure a smooth motion pattern. In a posterior stabilized (PS) TKA and posterior cruciate sacrificing (PCS) TKA, the ACL and PCL are both sacrificed. With the cruciate ligaments in a PS and PCS TKA, and the ACL sacrificed in a PCR TKA, the femoral condyles can slide and move in abnormal manners.

The present disclosure contemplates that TKA knee joints often exhibit motion of the femoral condyles that is opposite of the normal knee, where one or both femoral condyles can slide anteriorly prior to reaching mid-flexion. The motion patterns of TKA femoral condyles reflected in FIGS. 2 and 3 can be “jerky” or oscillating and include abrupt changes of direction in proximity to mid-flexion, which a patient can perceive as instability of the knee joint and feeling insecure during normal daily activities.

The present disclosure contemplates that, unlike TKA knee joints, normal knee joints lateral femoral condyle at full extension contact points start around 5 to 10 millimeters anterior the anteroposterior midline and progressively move posteriorly until reaching full flexion around 10 to 20 millimeters posterior of the anteroposterior midline. These contact points from full extension to full flexion allow greater flexion of the femur with respect to the tibia.

The present disclosure contemplates that using in vivo fluoroscopy in three-dimensions, many studies conducted on TKA patients document very different kinematic knee joint motion patterns compared to the normal knee. It is presumed that these joint motion pattern differences are due to the loss of the ACL in a PCR TKA and the loss of both cruciate ligaments in a PS TKA, along with improper balancing of the collateral ligaments. Unlike the normal knee where the lateral femoral condyle contact progressively moves in the posterior direction with increasing knee flexion, TKA patients often demonstrate significant anterior motion (the opposite of normal knee kinematics) during flexion. In the normal knee, the medial femoral condyle contact begins around 0-5 millimeters anterior of the anteroposterior midline at full extension and remains very stable with increasing knee flexion. In TKA patients, the medial femoral condyle often exhibits abnormal motion that reverses direction in between full extension and mid-flexion, thus leading to mid-flexion instability.

The present disclosure contemplates that these abnormal medial and lateral femoral condyle contact points, especially near mid-flexion, often result in patients noticing the abnormal motion and having stability concerns. During fluoroscopy it has been seen that patients have to hold onto railings or gain support from other people while flexing their knee because of this sliding motion, causing them to feel unstable. In the normal knee, the femoral condyles start anterior on the tibia and progressively move posteriorly, but with TKA knee joints, the contact patterns are quite variable and often lead to sudden directional changes that a patient feels due the femoral condyles sliding on the tibial tray. Therefore, when a TKA patient bends his/her knee joint, the femur slides forward rather than rolling back. Also, during chair rise and step-up maneuvers, the femoral condyles slide posteriorly rather than rolling forward. In the normal knee, rolling feels stable to a person, but in a TKA knee joint, abnormal sliding and directional changes translate into a patient feeling mid-flexion instability.

The present disclosure contemplates that during knee replacement surgery, the knee joint is typically balanced at either full extension and/or 90 degrees of flexion. Therefore, even though mid-flexion is the area when a patient experiences significant abnormal motion, the knee joint is typically not balanced by the surgeon at this flexion degree or proximate this degree of flexion. Therefore, during the transition range of motion from full extension to 90 degrees of flexion, the absence of balancing within this range of motion may lead to ligaments not being properly balanced throughout the knee joint range of motion. And this improper balancing may lead to improper femoral and tibial bone cuts or it can be viewed in an opposite manner where improper or incorrect bone cuts lead to poor knee balance. The present disclosure contemplates that if balancing was conducted in the mid-flexion range, then the knee could feel more stable between full extension to 90 degrees of flexion, because, for example, the transitional amount to either full extension or 90 degrees of flexion would only be about 45 degrees. Understanding ligament balancing proximate mid-flexion, may result in knowledge about ligament lengths, strain, and forces for improved balancing of a knee arthroplasty joint. Unfortunately, the balancing of the knee at full extension and or 90 degrees of flexion is often done by feel and in a passive environment. Therefore, load is not applied to the bearing surface and the ligaments are not in tension. This form of knee balancing could be reason for knee instability and the patients feeling abnormal slipping occurring with their knee.

Accordingly, there is a need in the art to ligament balance a knee arthroplasty joint that includes balancing at least proximate mid-flexion of the joint. In some example embodiments according to at least some aspects of the present disclosure, mid-flexion may include angles such as about 30 degrees to about 70 degrees, but midflexion instability does appear at other flexion angles, between full extension (zero degrees) and 90 degrees away from full extension. In this manner, the knee arthroplasty joint is balanced at an angle proximate where the majority of abnormal motion of an orthopedic knee joint would otherwise be present if balancing of the knee arthroplasty joint was not undertaken between full extension and 90 degrees from full extension.

There is also a need in the art for surgical tools and equipment specifically directed to facilitate ligament balancing of a knee arthroplasty joint at mid-flexion angles between full extension and 90 degrees from full extension, and specifically encompassing angles between about 30 and about 70 degrees from full extension.

It is an aspect of the present disclosure to provide a knee balancing jig for an arthroplasty procedure, including a tibial placement guide configured for mounting to a tibial reference in a generally medial-lateral orientation in position generally anterior to a knee including a femur and a tibia; and/or at least one balancing assembly. The at least one balancing assembly may include a vertical guide configured to releasably mount to the tibial placement guide in a generally inferior-superior orientation, at least one posteriorly extending paddle selectively vertically movable along the vertical guide, the at least one paddle configured to selectively engage at least one of a distal femur and a proximal tibia; and/or at least one pin guide selectively vertically movable along the vertical guide, the at least one pin guide including at least one opening configured to receive at least one of a drill bit and a bone pin therethrough.

In a detailed embodiment, the at least one balancing assembly may include at least two of the balancing assemblies, the at least two balancing assemblies including a medial balancing assembly configured to releasably mount medially on the tibial placement guide; and/or a lateral balancing assembly configured to releasably mount laterally on the tibial placement guide.

In a detailed embodiment, the at least one paddle of the medial balancing assembly may be configured to selectively engage at least one of a medial condyle of the distal femur and a medial condyle of the proximal tibia; and/or the at least one paddle of the lateral balancing assembly may be configured to selectively engage at least one of a lateral condyle of the distal femur and a lateral condyle of the proximal tibia.

In a detailed embodiment, the at least one paddle may include two of the paddles including a superior paddle and an inferior paddle. The superior paddle may be configured to selectively engage the distal femur. The inferior paddle may be configured to engage the proximal tibia.

In a detailed embodiment, the at least one pin guide may include two of the pin guides including a femoral pin guide and a tibial pin guide. The femoral pin guide may be configured for use in connection with placing a femoral bone pin in the femur. The tibial pin guide may be configured for use in connection with placing a tibial bone pin in the tibia.

In a detailed embodiment, the knee balancing jig may include the tibial reference. In a detailed embodiment, the tibial reference may include a tibial extramedullary rod.

In a detailed embodiment, the knee balancing jig may include a femoral placement guide configured for mounting to the tibial reference. The femoral placement guide may include a receiving device configured to engage a femoral reference. In a detailed embodiment, the femoral placement guide may be configured to engage the femoral reference at a fixed angle associated with a mid-flexion position of the knee. The mid-flexion position of the knee may correspond approximately to a posterior chamfer cut angle of a femoral implant associated with the arthroplasty procedure.

In a detailed embodiment, the mid-flexion position of the knee may be between about 30 degrees of flexion and about 70 degrees of flexion. In a detailed embodiment, the mid-flexion position of the knee may be between about 30 degrees of flexion and about 60 degrees of flexion. In a detailed embodiment, the mid-flexion position of the knee may be about 45 degrees of flexion.

In a detailed embodiment, the femoral placement guide may be configured to engage the femoral reference at an adjustable angle associated with a mid-flexion position of the knee.

In a detailed embodiment, the knee balancing jig may include the femoral reference. The femoral reference may include a femoral intramedullary rod. The femoral reference may include an external femoral component.

In a detailed embodiment, the knee balancing jig may include at least one cut guide. The at least one cut guide may be configured to guide a cutting device in connection with resection of at least one of the femur and the tibia. The at least one cut guide may be configured to mount to the at least one of the femur and the tibia using the bone pine associated with the opening of the at least one pin guide of the at least one balancing assembly.

In a detailed embodiment, the at least one cut guide may include two of the cut guides including a femoral cut guide and a tibial cut guide. The femoral cut guide may be configured to guide the cutting device in connection with resection of the femur. The tibial cut guide may be configured to guide the cutting device in connection with resection of the tibia.

In a detailed embodiment, the femoral cut guide may include two of the femoral cut guides including a posterior chamfer cut guide and a femoral extension cut guide. The posterior chamfer cut guide may be configured to guide the cutting device in connection with a posterior chamfer cut of the femur. The femoral extension cut guide may be configured to guide the cutting device in connection with a femoral extension cut of the femur.

In a detailed embodiment, the at least one posteriorly extending paddle may include at least one adjustable engagement feature. The adjustable engagement feature may be repositionable in an anterior-posterior direction.

It is an aspect of the present disclosure to provide a method of preparing a knee to receive a knee implant, including positioning a knee including a distal femur and a proximal tibia at a mid-flexion angle; performing soft tissue balancing of the knee at the mid-flexion angle; determining a location of a posterior chamfer cut of the distal femur configured to engage the posterior chamfer angle of a femoral component of a knee implant based at least in part upon the soft tissue balancing of the knee at the mid-flexion angle; and resecting the distal femur to create the posterior chamfer cut.

In a detailed embodiment, the mid-flexion angle may correspond approximately to a posterior chamfer angle of the femoral component of the knee implant. In a detailed embodiment, the mid-flexion angle may be between about 30 degrees of flexion and about 70 degrees of flexion. In a detailed embodiment, the mid-flexion angle may be between about 30 degrees of flexion and about 60 degrees of flexion. In a detailed embodiment, the mid-flexion angle may be about 45 degrees of flexion.

In a detailed embodiment, the method may include performing soft tissue balancing of the knee relative to the posterior chamfer cut; determining a location of a tibial plateau cut configured to engage a tibial component of the knee implant based at least in part upon the soft tissue balancing of the knee relative to the posterior chamfer cut; and/or resecting the proximal tibia to create the tibial plateau cut.

In a detailed embodiment, the method may include positioning the knee at full extension; performing soft tissue balancing of the knee relative to the tibial plateau cut; determining a location of a femoral extension cut configured to engage the femoral component of the knee implant based at least in part upon the soft tissue balancing of the knee relative to the tibial plateau cut; and/or resecting the distal femur to create the femoral extension cut.

In a detailed embodiment, the method may include positioning the knee at about 90 degrees of flexion; performing soft tissue balancing of the knee relative to the tibial plateau cut; determining a location of a femoral flexion cut configured to engage the femoral component of the knee implant based at least in part upon the soft tissue balancing of the knee relative to the tibial plateau cut; and/or resecting the distal femur to create the femoral flexion cut.

In a detailed embodiment, the method may include determining a location of a femoral flexion cut configured to engage the femoral component of the knee implant based at least in part upon a femoral component size determined using an anterior reference guide; and/or resecting the distal femur to create the femoral flexion cut.

In a detailed embodiment, using the anterior reference guide may include placing a movable stylus of the anterior reference guide on an anterior aspect of the distal femur; and/or translating a posterior indicator of the anterior reference guide using the movable stylus.

In a detailed embodiment, the anterior reference guide may include a posterior chamfer cut contact surface; and/or using the anterior reference guide may include positioning the posterior chamfer cut contact surface on the posterior chamfer cut.

In a detailed embodiment, performing soft tissue balancing of the knee at the mid-flexion angle may include performing soft tissue balancing of the knee at the mid-flexion angle relative to a tibial plateau cut of the proximal tibia.

In a detailed embodiment, the method may include, before performing soft tissue balancing of the knee at the mid-flexion angle relative to the tibial plateau cut of the proximal tibia, resecting the proximal tibia to create the tibial plateau cut.

In a detailed embodiment, performing soft tissue balancing of the knee at the mid-flexion angle may include applying a linear separating force to bones including the knee using a gap tensioner.

In a detailed embodiment, applying the linear separating force to bones of the knee using the gap tensioner may include inserting a first paddle and a second paddle into a gap between the bones of the knee; and/or applying the linear separating force to the bones of the knee using the first paddle and the second paddle.

In a detailed embodiment, applying the linear separating force to the bones of the knee using the first paddle and the second paddle may include applying a torsional force to the gap tensioner, the gap tensioner converting the torsional force to the linear separating force.

In a detailed embodiment, applying the torsional force to the gap tensioner may include applying a torsional force to an actuating shaft of the gap tensioner using a torque wrench.

It is an aspect of the present disclosure to provide an intramedullary rod including a straight shaft having a predetermined length, the straight shaft including a surgical grade material, the straight shaft including a collar that differentiates a proximal portion of the straight shaft for insertion into a bone canal and a distal portion of the straight shaft extending externally from the bone canal.

It is an aspect of the present disclosure to provide a knee arthroplasty set of guides including a femoral guide configured to mount to a distal femur; and/or a tibial guide configured to mount to a proximal tibia. The femoral guide and/or the tibial guide may be configured to engage one another and lock in an angle between a longitudinal axis of the distal femur and a longitudinal axis of the proximal tibia of 30-70 degrees.

In a detailed embodiment, the set of guides may include a medial condyle insert configured to measure a gap between a medial condyle of the distal femur and a medial condyle receiver of the proximal tibia; and/or a lateral condyle insert configured to measure a gap between a lateral condyle of the distal femur and a lateral condyle receiver of the proximal tibia. The medial condyle insert and/or the lateral condyle insert may be configured to be repositionably mounted to at least one of the femoral guide and the tibial guide.

In a detailed embodiment, the medial condyle insert and/or the lateral condyle insert may be configured to be repositionably mounted to the tibial guide; the medial condyle insert may include at least two paddles that are repositionable with respect to one another to vary a distance therebetween; and/or the lateral condyle insert includes at least two paddles that are repositionable with respect to one another to vary a distance therebetween.

In a detailed embodiment, the at least two paddles of the medial condyle insert may be configured to engage a medial guide of the tibial guide, where at least one of the medial guide and the at least two paddles includes indicia thereon to determine a distance opposing surfaces of the at least two paddles are from one another; and/or the at least two paddles of the lateral condyle insert may be configured to engage a lateral guide of the tibial guide, where at least one of the lateral guide and the at least two paddles includes indicia thereon to determine a distance opposing surfaces of the at least two paddles are from one another.

In a detailed embodiment, the set of guides may include a medial condyle drill guide; and/or a lateral condyle drill guide. The medial condyle drill guide and/or the lateral condyle drill guide may be configured to be repositionably mounted to at least one of the femoral guide and the tibial guide.

In a detailed embodiment, the medial condyle drill guide and/or the lateral condyle drill guide may be configured to be repositionably mounted to the tibial guide. In a detailed embodiment, the medial condyle drill guide may be configured to engage a medial guide of the tibial guide, where at least one of the medial guide and the medial condyle drill guide includes indicia thereon to determine a distance between a reference point and the medial condyle drill guide; and/or the lateral condyle drill guide is configured to engage a lateral guide of the tibial guide, where at least one of the lateral guide and the lateral condyle drill guide includes indicia thereon to determine a distance between a reference point and the lateral condyle drill guide.

In a detailed embodiment, the set of guides may include a medial condyle receiver drill guide; and/or a lateral condyle receiver drill guide. The medial condyle receiver drill guide and/or the lateral condyle receiver drill guide may be configured to be repositionably mounted to at least one of the femoral guide and the tibial guide.

In a detailed embodiment, the medial condyle receiver drill guide and the lateral condyle receiver drill guide may be configured to be repositionably mounted to the tibial guide.

In a detailed embodiment, the medial condyle receiver drill guide may be configured to engage a medial guide of the tibial guide, where at least one of the medial guide and the medial condyle receiver drill guide includes indicia thereon to determine a distance between a reference point and the medial condyle receiver drill guide; and/or the lateral condyle receiver drill guide may be configured to engage a lateral guide of the tibial guide, where at least one of the lateral guide and the lateral condyle receiver drill guide includes indicia thereon to determine a distance between a reference point and the lateral condyle receiver drill guide.

In a detailed embodiment, the set of guides may include a posterior chamfer cut cutting guide. The posterior chamfer cutting guide may be configured to engage artificial features on the distal femur to align the posterior chamfer cut cutting guide with respect to the distal femur to make a posterior chamfer cut.

In a detailed embodiment, the set of guides may include a tibial cutting guide. The tibial cutting guide may be configured to engage artificial features on the proximal tibia to align the tibial cutting guide with respect to the proximal tibia to make a tibial plateau cut.

In a detailed embodiment, the set of guides may include a femoral extension cutting guide. The femoral extension cutting guide may be configured to engage artificial features on the distal femur to align the femoral extension cutting guide with respect to the distal femur to make a femoral extension cut.

In a detailed embodiment, the set of guides may include an anterior chamfer cut cutting guide. The anterior chamfer cutting guide may be configured to engage artificial features on the distal femur to align the anterior chamfer cut cutting guide with respect to the distal femur to make an anterior chamfer cut.

In a detailed embodiment, the tibial guide may include an extramedullary rod configured to extend longitudinally along the tibia; the tibial guide may include a cross-beam operatively coupled to the extramedullary rod; the tibial guide may include first guide configured to traverse along the cross-beam; and/or the tibial guide may include a second guide configured to traverse along the cross-beam.

In a detailed embodiment, the set of guides may include a medial condyle insert configured to traverse the first guide, the medial condyle insert configured to measure a gap between a medial condyle of the distal femur and a medial condyle receiver of the proximal tibia; and/or a lateral condyle insert configured traverse the second guide, the lateral condyle insert configured to measure a gap between a lateral condyle of the distal femur and a lateral condyle receiver of the proximal tibia.

In a detailed embodiment, the set of guides may include a medial condyle drill guide configured to traverse the first guide; and/or a lateral condyle drill guide configured to traverse the second guide.

In a detailed embodiment, the set of guides may include a medial condyle receiver drill guide configured to traverse the first guide; and/or a lateral condyle receiver drill guide configured to traverse the second guide.

It is an aspect of the present disclosure to provide a method of performing a knee arthroplasty, the method including mounting a femoral guide to a distal femur; aligning and engaging a tibial guide with the femoral guide, where an angle between the femoral guide and the tibial guide is between 30-70 degrees; mounting the tibial guide to a proximal tibia; using the tibial guide to establish at least one of a position and an orientation of a femoral posterior chamfer cut cutting guide; using the femoral posterior chamfer cutting guide to make a posterior chamfer cut on at least one condyle of the distal femur; resecting the proximal tibia to remove at least a portion of bone previously underlying at least one condyle receiver; and/or resecting the at least one condyle of the distal femur, where the resection is angled between 30-70 degrees with respect to the posterior chamfer cut.

It is an aspect of the present disclosure to provide a method of performing a knee arthroplasty, the method including fixing an orientation of a distal femur with respect to a proximal tibia so that a longitudinal axis of the distal femur is angled between 30-70 degrees with respect to a longitudinal axis of the proximal tibia; balancing, while the longitudinal axis of the distal femur is angled between 30-70 degrees with respect to the longitudinal axis of the proximal tibia, at least one of (i) a medial portion of a knee joint that includes the distal femur and proximal tibia, and (ii) a lateral portion of the knee joint that includes the distal femur and proximal tibia; determining, when the balancing is complete, spacing between at least one of (i) a medial condyle of the distal femur and a medial condyle receiver of the proximal tibia, and (ii) a lateral condyle of the distal femur and a lateral condyle receiver of the proximal tibia; and/or using a femoral posterior chamfer cutting guide to make a posterior chamfer cut on at least one condyle of the distal femur before making an anterior chamfer cut or a distal cut.

It is an aspect of the present disclosure to provide a method of performing a knee arthroplasty, the method including fixing an orientation of a distal femur with respect to a proximal tibia so that a longitudinal axis of the distal femur is angled between 30-70 degrees with respect to a longitudinal axis of the proximal tibia; balancing, while the longitudinal axis of the distal femur is angled between 30-70 degrees with respect to the longitudinal axis of the proximal tibia, at least one of (i) a medial portion of a knee joint that includes the distal femur and proximal tibia, and (ii) a lateral portion of the knee joint that includes the distal femur and proximal tibia; determining, when the balancing is complete, spacing between at least one of (i) a medial condyle of the distal femur and a medial condyle receiver of the proximal tibia, and (ii) a lateral condyle of the distal femur and a lateral condyle receiver of the proximal tibia; and/or using a tibial cutting guide to make a tibial plateau cut on at least one condyle of the proximal tibia before making a femoral anterior chamfer cut or a femoral distal cut.

It is an aspect of the present disclosure to provide a gap tensioner for a balancing jig for a joint arthroplasty procedure, the gap tensioner including a first engagement element configured to operatively couple to a first paddle of a balancing assembly; a second engagement element configured to operatively couple to a second paddle of the balancing assembly; and an actuating mechanism configured to change the spacing between the first engagement element and the second engagement element; wherein the balancing jig includes the first paddle and the second paddle disposed on a guide, the first paddle and the second paddle configured to be placed between bones of a joint; and/or wherein the balancing assembly is configured so that at least one of the first paddle and the second paddle is movable along the guide to expand a gap between the bones of the joint.

In a detailed embodiment, the gap tensioner may include a housing; the first engagement element may be linearly slidable relative to the housing; and/or the second engagement element may be rigidly disposed relative to the housing.

In a detailed embodiment, the actuating mechanism may include a rack and pinion mechanism. The rack and pinion mechanism may include a pinion rotatably disposed on the housing, and/or a rack rigidly disposed relative to the first engagement element.

In a detailed embodiment, the gap tensioner may include an actuating shaft operatively coupled to the pinion, the actuating shaft configured to receive an input torsional force.

It is an aspect of the present disclosure to provide an apparatus including a gap tensioner as described above and/or the balancing assembly.

DETAILED DESCRIPTION

Figure 1:
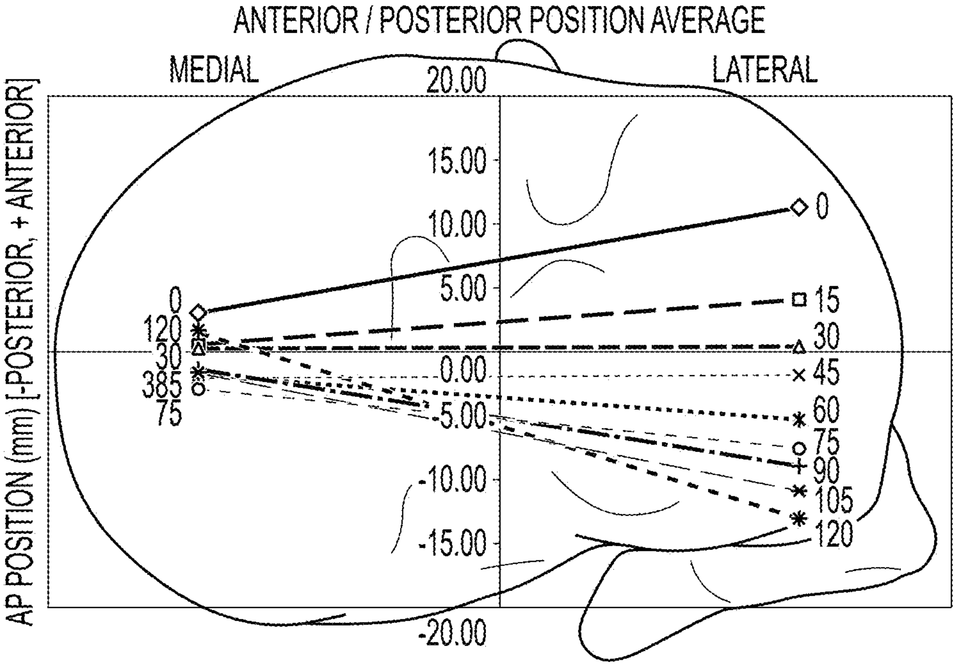
FIG. 1 is a plot of a motion pattern for a normal knee joint showing the anterior-posterior positions of the medial and lateral condyles at various degrees of flexion.
Figure 2:
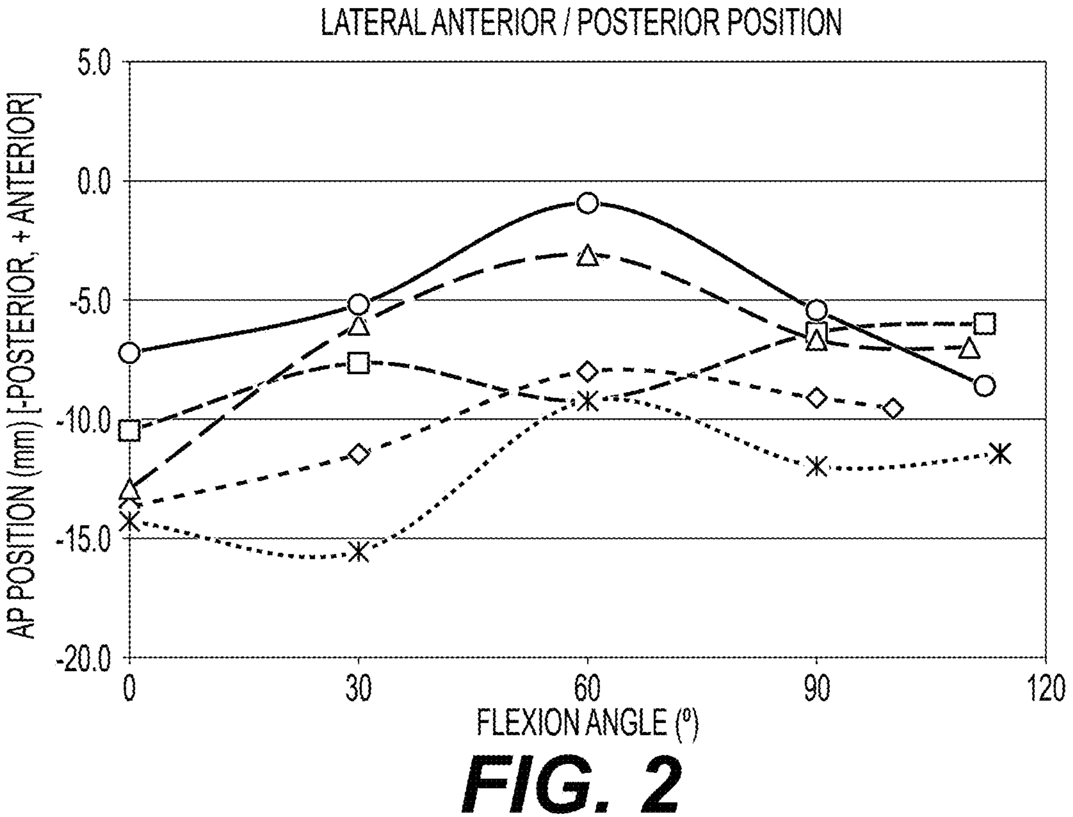
FIG. 2 is a plot of the anterior-posterior position of the lateral condyle as a function of flexion angle for five subjects implanted with a posterior cruciate ligament retaining total knee arthroplasty.
Figure 3:
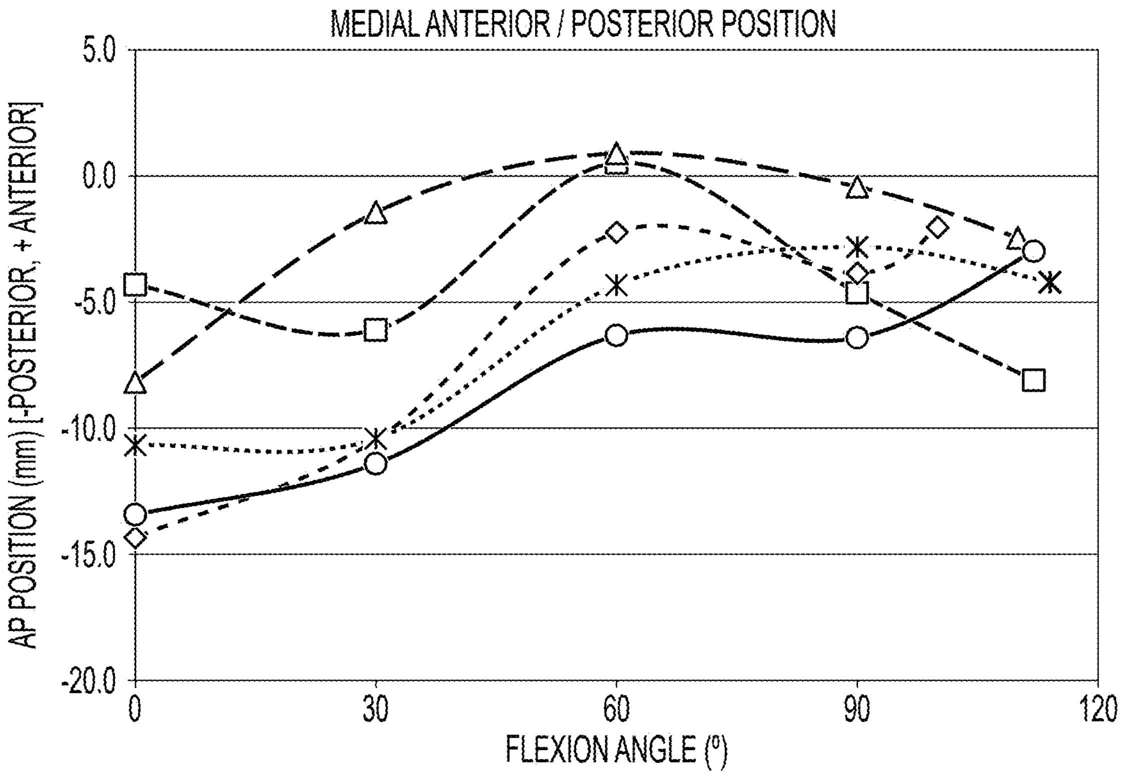
FIG. 3 is a plot of the anterior-posterior position of the medial condyle as a function of flexion angle for five subjects implanted with a posterior cruciate ligament retaining total knee arthroplasty.

The exemplary embodiments of the present disclosure are described and illustrated below to encompass surgical equipment and associated methods for performing a knee arthroplasty procedure. It should be noted that while the discussion hereafter may refer to total knee arthroplasty (TKA), it should be understood that for purposes of explanation herein, TKA is also intended to encompass partial knee arthroplasty (PKA), unicompartmental knee arthroplasty (UKA), and revision knee arthroplasty (RKA). To the extent any surgical equipment and techniques described herein are unique to PKA, UKA, or RKA, an associated discussion will be included. Otherwise, any reference to TKA is intended to encompass PKA, UKA, and RKA. In addition, any reference herein to "patient" includes live and dead humans, as well as any live or dead non-human mammal. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

The present disclosure contemplates that to achieve alignment and component position of femoral and tibial components as part of a TKA procedure, there are two predominant methodologies for performing a knee replacement. In a first methodology, commonly known as the "Gap Balanced" technique, the patient's knee joint is distracted either in extension or 90 degrees of flexion first, with the implication that the collateral ligaments are "balanced" in tension, and thereafter a resection of the femur and proximal tibia is performed. Traditional concepts of bone distance removal of 9 millimeters from the non-deficient distal femoral condyle, and 4 millimeters off the deficient tibial condyle, may be used, with the cuts made in varus and valgus on both the femur and tibia to achieve a neutral mechanical axis (i.e., when the bone ends are placed together the leg is "straight"). Depending upon whether one resects the proximal tibia or distal femur first has implications for the subsequent ligament balance obtained thereafter. With the Gap Balanced technique, the assumption is that a rectangle or near rectangle of known distance is created between the bone ends, where this rectangle includes a dominant distance that is the same in full extension and at 90 degrees of flexion.

The present disclosure contemplates that, in contrast, the second most common methodology, referred to as the "Measured Resection" technique, requires a surgeon to take measured amounts of bone from the distal femur and proximal tibia (similar to that for the Gap Balanced technique), and then perform releases, if necessary, to create a rectangle of known distance. By removing an equal amount of bone from the posterior femur and the distal femur, and performing any releases, the assumption is that a rectangle of known (and equal) distance is created. The present disclosure contemplates that this assumption as to the desirability of rectangularity in either method, as well as where this rectangle should be placed, may be a faulty premise in some circumstances.

The present disclosure contemplates that the desirability of rectangularity and the location of the rectangle may be based on at least four inherent and poorly defined assumptions: 1) that a rectangle of constant distance is created in extension and in flexion; 2) the rectangle does not change in width over a 90 degree arc of motion (extension to 90 degrees of flexion); 3) that the balanced ligaments are equidistant in the positions of extension and flexion; and, 4) that the surgeon can define the rectangle placement in three planes by making cuts at two distinct angles (distal femur and proximal tibia) without any knowledge of the accuracy of the planes created on the femur and tibia.

The present disclosure contemplates that in a study of 101 computer navigated TKA knees, it was discovered that after initial creation of "mechanical neutral" proximal tibial and distal femoral resections and subsequent anterior-posterior (AP) femoral cuts, an average of two "releases" were required for placement of trial components to achieve a balanced knee (balance defined as equal "force" medially and laterally obtained via a tibial sensor when the "heel push test" was performed throughout a range of motion). While of interest, the bone cuts were performed separately, and the total force applied was only alluded to (120-145 Newtons per manuscript). Of note, increasing the tibial insert thickness 2 millimeters increased the total force by approximately 70%, thus tending to prove that one can create a sense of stability. In most manufacturing processes for orthopedic implant components, an inaccuracy of this level would lead to a process redesign; in TKA, such inaccuracy may lead to mid-flexion and flexion laxity, and patient dissatisfaction. The present disclosure contemplates that using either the Gap Balancing or Measured Resection technique may result in inherent inaccuracy.

The present disclosure contemplates that an underlying issue in ligament balancing is not just in achieving some relationship between the medial and lateral collateral ligaments, it is in agreeing on where this relationship should occur. Studies undertaken of the medial and lateral collateral ligaments divided these ligaments into three portions (anterior, middle, and posterior) and examined the in vivo changes in ligament length during flexion. In general, over the range of motion from full extension to at least 90 degrees flexion, the anterior fibers increased in length, the middle fibers did not change, and the posterior fibers reduced in length. Applying these observations to the Gap Balancing technique reveals mechanical conflicts in ligament balancing driven by the technique itself. From the understanding of ligament length, particularly of the medial collateral ligament (MCL), and the range of length change seen from extension to 90 degrees of flexion, balancing in flexion and extension results in a lax MCL in mid-flexion.

The present disclosure contemplates that Gap Balancing can be reduced to the simple imposition of a defined distance between two bone ends (one of which must be cut first) if, after the proximal tibial resection is made, the knee is held in flexion and the ligaments are balanced and the posterior resection cuts are being marked. However, a resection made without reference (except anteriorly) to the prior cut may create a larger or smaller gap posteriorly. The same issue arises in extension when making the distal femoral resection. While the amount of anterior bone to be resected is planned based on the distance identified in flexion, the execution often times fails to keep the flexion extension axis constant. Accordingly, resections/cuts that are not linked in plane are divergent from anterior to posterior. Therefore, a Gap Balanced knee may keep a constant anterior distance between the anterior aspect of the femoral resection(s) and the proximal tibial resection, but not a constant posterior distance. Empirical evidence suggests that creation of a constant rectangle is almost never achieved when using the Gap Balanced technique, which is one of the causes of flexion laxity. In addition, the MCL and lateral collateral ligament (LCL) vary in length between full extension and 90 degrees of flexion and beyond. Thus, if the Gap Balancing technique is predicated on flexion balancing first, the identified "gap" in flexion results in over resecting the distal femur, again leading to mid-flexion laxity. And if the distal femur is cut after the proximal tibia, and thereafter the posterior femoral resection is made, this often results in over resection of the posterior femur. These same issues occur using the Measured Resection technique.

The present disclosure contemplates that despite the technical appearance of a well-done TKA (full range of motion, varus valgus and anterior posterior stability, and radiographic confirmation of appropriate placement of the components), at least 25% of patients report dissatisfaction with their reconstructed knee joint. Typical problems include, but are not limited to, ongoing pain, a feeling of instability, quadriceps soreness, and swelling. Essentially, what is occurring is anterior translation of the tibial component relative to the femoral component, which is equivalent to an anterior cruciate deficient knee. The clinical diagnosis of what is causing this can be broken down into two possibilities (or both) based on where the knee appears to be lax to stress: (a) mid-flexion, defined as increased varus valgus opening to stress at 30 to 60 degrees of flexion; or, (b) flexion, defined as increased anterior laxity at 90 degrees of flexion. Generally, for these conditions to exist, the knee is stable (i.e., no opening to varus/valgus stress) in full extension.

The present disclosure contemplates that flexion laxity at 90 degrees of flexion is often easier to diagnose than mid-flexion laxity. While it is generally accepted that the clinical finding of flexion laxity is greater than 5 mm of anterior-posterior (AP) laxity at 90 degrees of flexion, there may be several caveats. For any midpoint sagittal axis defined by the femoral component, the tibial component is either directly under (neutral), anterior to, or posterior to, this axis. The knee should be pushed posteriorly to a maximal position defined by either the post of the posteriorly stabilized component hitting the femoral cam, or where the posterior translation is stopped by the posterior cruciate ligament. From this position with the leg hanging (note that performance of this test with the patient lying down results in the weight of the thigh, and the conformity of the tibial liner, potentially influencing the findings) the knee is drawered forward and the laxity graded as either less than 5 mm, 5 to 10 mm, or greater than 10 mm. The lax side can be assessed as well by stressing the knee into varus and valgus and noting where femoral rotation begins to be seen. The "hanging clunk" sign has been defined and represents the reduction of the tibia to the posterior femur. This clunk can be identified either by testing for a deep tendon reflex, or asking the patient to rapidly extend the knee from 90 degrees of flexion and noting the superior translation of the tibia prior to the leg extending. It is assumed that at this level of laxity there is mid-flexion laxity as well.

The present disclosure contemplates that mid-flexion laxity is harder to diagnose. Testing of the varus/valgus stability at 30 degrees of flexion may suggest laxity of one of the collateral ligaments, or both.

The present disclosure contemplates that the current state of preparation and procedure for performing a TKA neither addresses nor evaluates the laxity seen when femoral and tibial cuts are performed without planar reference to each other (linked), or suggests where within a soft tissue envelope the orthopedic implants should be placed. In simplest terms, the imposition of a constant rectangle of known width from extension to 90 degrees of flexion is not achieved with accuracy. From a kinematic standpoint, as the knee starts to flex, if the rectangular distance is not a constant, the increased distance results in anterior translation of the tibia. This may be counteracted by quadriceps contraction. Over the first 90 degrees of motion, the tibial component, rather than maintaining a constant relationship in distance to the femoral component, oscillates anteriorly, and then reduces with quadriceps force, and then oscillates, creating a sinusoidal curve over the first 90 degrees of flexion.

The present disclosure contemplates that a main concern for gap balancing is that the determination of tension or spacing on each side is not exact. If a surgeon attempts to gap balance and hopes to achieve 50% tension of the ligaments on the lateral side and 50% tension of the ligaments on the medial side or 50% compression of each condyle, but is not exact, the patients may have 60-80% of the tension or compression on one side and 20-40% on the other side. This would lead to an imbalance and could result in the abnormal kinematics discussed earlier. Having greater tension on one side or greater compression on one slide could lead to excessive abnormal sliding of one condyle leading to abnormal or reverse axial rotation.

Figure 4:
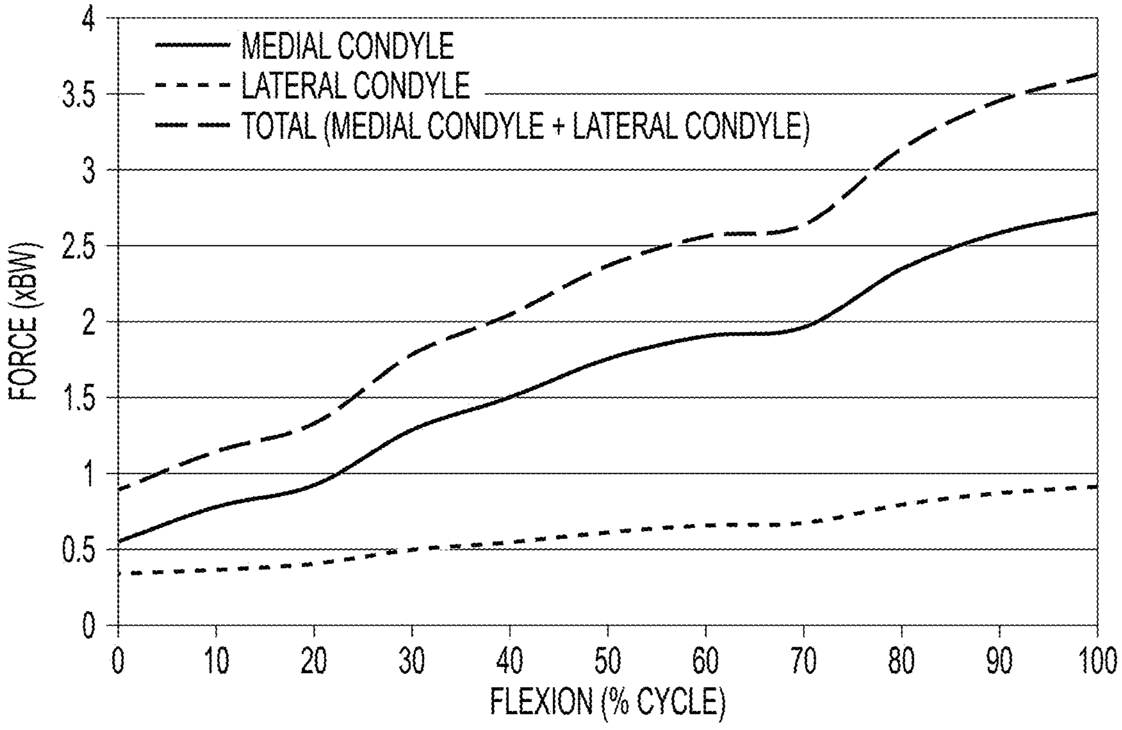
FIG. 4 is a plot of force as a function of flexion for the medial and lateral condyles of a normal knee.
Figure 5:
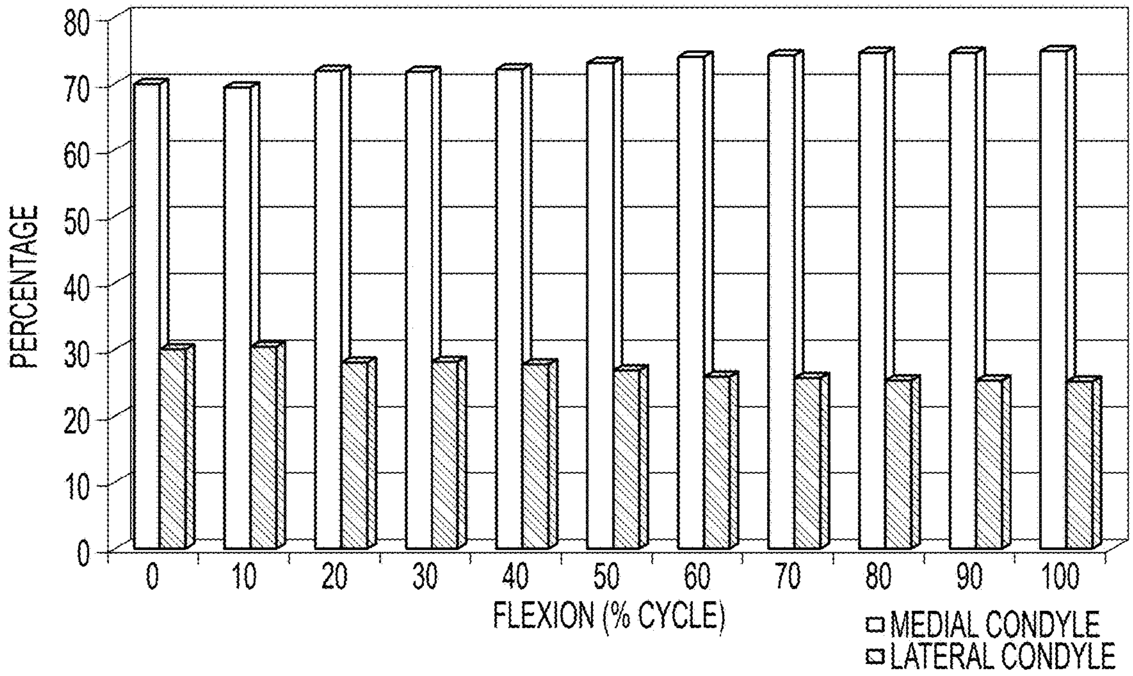
FIG. 5 is a bar graph showing the percentage of the total force that is imposed on each of the medial and lateral condyles at various flexion angles.

FIG. 4 is a plot of force as a function of flexion for the medial and lateral condyles of a normal knee, and FIG. 5 is a bar graph showing the percentage of the total force that is imposed on each of the medial and lateral condyles at various flexion angles. Referring to FIGS. 4 and 5, the present disclosure contemplates that, in a normal knee joint, the femorotibial forces interacting at the medial femoral condyle are higher than those forces interacting at the lateral femoral condyle. The femorotibial force passing through the medial femoral condyle are routinely about 60-70% of the overall force, while the lateral femoral condyle exhibits 30-40% of the overall knee force. In extreme cases, the femorotibial forces passing through the medial femoral condyle can be more than 2.5× that of the forces passing through the lateral femoral condyle.

The present disclosure contemplates that although the forces are not symmetrical in the normal knee, surgeons may attempt to gap balance the knee desiring to have equal forces for the medial and lateral condyles. Unfortunately, this may be done under passive conditions and not using reliable instrumentation to ensure the goal is equal to the outcome. Further, despite the pre-surgical asymmetrical loading, the TKA surgery may be intentionally performed to yield symmetrical loading. This could be a reason why the axial rotation of implanted knees is much less than the axial rotation of the normal knee.

The present disclosure contemplates that since a normal knee joint experiences more rollback of the lateral femoral condyle during knee flexion and axial rotation of the lateral femoral condyle with respect to the medial femoral condyle, allowing the medial femoral condyle to remain more central and the lateral femoral condyle, having less force, is able to swing around the medial femoral condyle. In addition, in the normal knee, the femoral condyles are asymmetric in shape, as well as ligament balancing and soft-tissue forces being asymmetric. When a surgeon attempts to Gap Balance a TKA, the surgeon is changing the knee balance and can cause a hinge-like motion pattern where both condyles move symmetrically and exhibit much less axial rotation. In the normal knee, on average, the knee experiences about 27 degrees of axial rotation, while in an average TKA joint, abnormal axial rotation patterns are exhibited with substantially less axial rotation (on the order of less than 3 degrees). If a surgeon attempts to balance the knee with equal gaps and tension, the result is often a TKA knee experiencing minimal or no axial rotation, or even reverse axial rotation.

Figure 6:
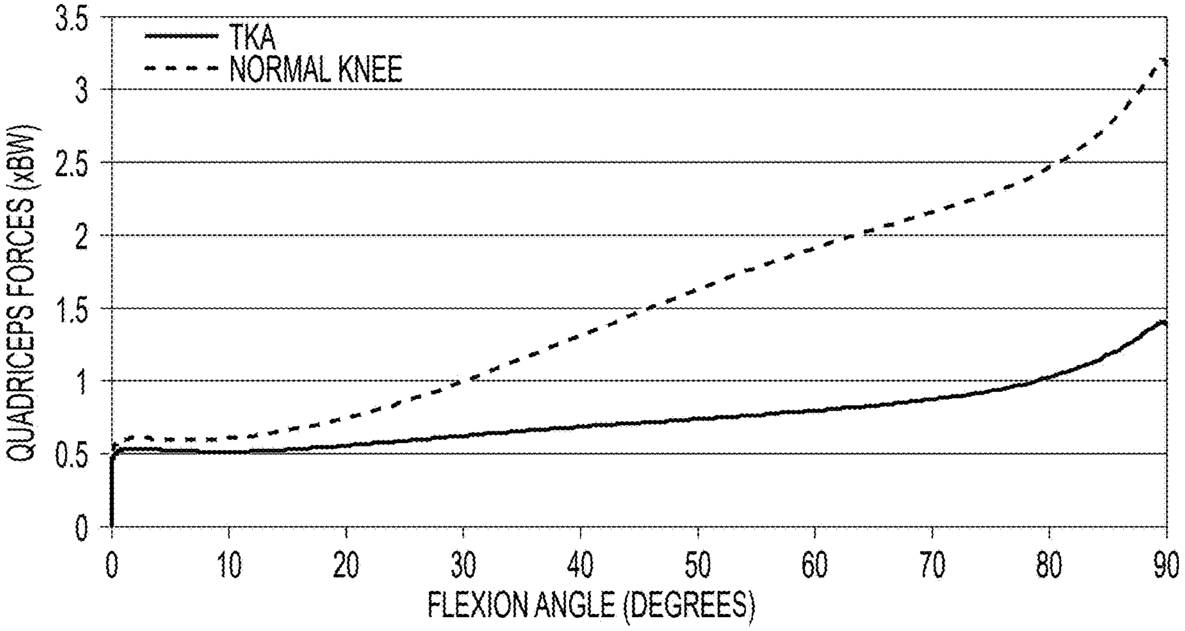
FIG. 6 is a plot of quadriceps force as a function of flexion angle for a normal knee and an implanted knee.

FIG. 6 is a plot of quadriceps force as a function of flexion angle for a normal knee and an implanted knee. Referencing FIG. 6, the present disclosure contemplates that if a TKA joint is improperly balanced (e.g., not balanced at mid-flexion), sliding of the femoral component may lead to a reaction by the quadriceps muscles and cause the force to be much greater than the amount necessary. Quadriceps muscle forces may be firing much earlier for a TKA than for a normal knee, thus leading to higher quadriceps forces in deeper flexion. There is only so much force that the quadriceps can apply to drive knee motion and when the maximum amount is utilized, the implanted knee can no longer flex any further. It has been shown that implanted knee motion is statistically less than the normal knee. This sliding motion of the femoral component induces the quadriceps muscles to apply greater forces in an attempt to stabilize the knee joint. Unfortunately, since the quadriceps muscles are only able to provide a maximum amount of force, and this force is necessary to stabilize the TKA joint in early flexion, some patients can reach flexion limits around 70-90 degrees of flexion due to the fact that their quadriceps muscle becomes too tight and exceeds their maximum allowable force too early. FIG. 6 reflects data obtained during in vivo studies measuring the quadriceps force applied as a function of flexion angle for a normal knee joint and a TKA joint during weight-bearing activities. In the normal knee joint, quadriceps force increases from full extension and are on the order of a 3× increase upon reaching 90 degrees flexion. In contrast, for a TKA joint, quadriceps force increases rather dramatically from full extension and are on the order of a 6.5× increase upon reaching 90 degrees flexion. And these higher quadriceps forces lead to abnormal knee mechanics and less than desired weight-bearing flexion in a TKA joint.

In accordance with the instant disclosure, it has been discovered that balancing a TKA joint at or proximate to mid-flexion obviates most, if not all, of the foregoing issues exhibited when otherwise balancing a TKA joint at full extension (0 degrees flexion) or beyond 90 degrees flexion. Specifically, balancing a TKA joint at mid-flexion may keep the knee joint more stable while performing weight-bearing activities, allowing muscle forces (such as the quadriceps) to be less and allowing for greater range of motion during weight-bearing knee joint flexion.

The present disclosure contemplates that balancing of the ligaments may create the potential for a rectangle to be imposed on two bony surfaces (distal femur, proximal tibia), where that rectangle should be placed may use traditional concepts of some need for measured resection (as noted above; one has to remove some bone, and that removal cannot violate the collateral ligament origin(s) or insertion(s)) and/or gap balancing. Some exemplary techniques in accordance with the instant disclosure may differ from other techniques by imposing a rectangle for symmetric balancing or a trapezoid for asymmetric balancing in six degrees of freedom wherein each cut plane on the femur and tibia (varus-valgus, anterior-posterior, and rotational) is intimately related and parallel to the corresponding cut plane (e.g., after equilateral ligament balancing the varus-valgus of the tibial cut results in the varus-valgus of the femoral cut, with cut resection levels based on known TKA principles).

The present disclosure contemplates that if a surgeon balances a knee at full extension and/or 90 degrees of knee flexion under passive conditions, the ligaments aren't loaded and as the knee flexes or extends away from the point of balancing, the ligaments may not remain balanced at different degrees of flexion and/or extension. The present disclosure contemplates that the instance of greatest instability or laxity in the knee may occur during mid-flexion, which may lead to abnormal knee kinematics and excessive sliding. Patients may feel this sense of sliding, leading to them not feeling confident as the knee doesn't feel stable.

Generally, some example methods according to at least some aspects of the present disclosure include measurement of knee ligament tension and gaps at (or near) the angle corresponding to the femoral chamfer angle. Once the knee is positioned at that angle, ligament and compartment information is derived and recorded. The first cut is the femoral chamfer cut. Then, the tibial cut is made with respect to the femoral chamfer cut. Alternatively, the first cut may be the tibial cut, and then the femoral chamfer cut may be made with respect to the tibial cut. The knee is again measured at this orientation so ligament lengths and tension and distances between the cuts are maintained and recorded. Then, knee is reoriented to full extension and ligament lengths and tension and compartment gaps are properly positioned and referenced with respect to the information gained and recorded at the knee chamfer angle. Then, the femoral extension cut is made. Therefore, the femoral component chamfer cut is the same distance from the tibial cut and the femoral extension cut is also the same distance from the tibial cut. Also, the ligament tensions and lengths when measured between the chamfer cut to the tibial cut are the same as the extension cut to the tibial cut.

FIGS. 7A-7H are sequential, simplified lateral section views of a knee joint undergoing femoral and tibial resections in connection with an example TKA procedure, all according to at least some aspects of the present disclosure. The following description referencing FIGS. 7A-7H is intended to provide an overview and context for the methods and apparatus described in detail below.

Figure 7A:
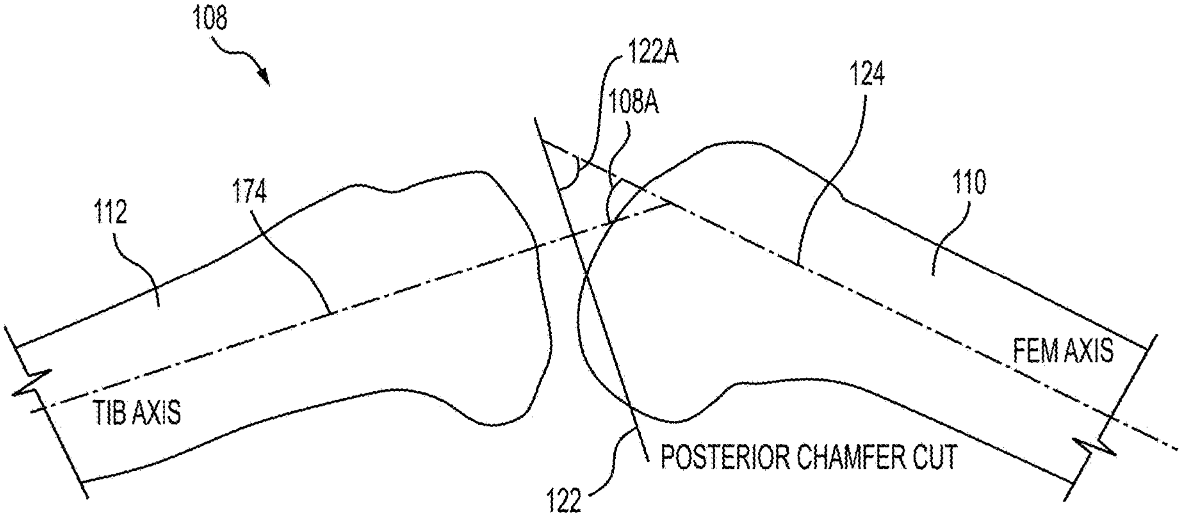
FIGS. 7A-7H are sequential, simplified lateral section views of a knee joint undergoing femoral and tibial resections in connection with a total knee arthroplasty procedure.

Turning to FIG. 7A, a knee joint 108 is positioned at a desired degree of flexion. For example, the knee joint 108 is positioned so that a flexion angle 108A between a femur 110 (e.g., femoral canal axis 124) and a tibia 112 (e.g., tibial longitudinal axis 174) is at a desired mid-flexion angle, such as about 45 degrees. In some example embodiments, balancing a TKA joint in accordance with the instant disclosure is performed at or proximate mid-flexion of the femur 110 with respect to the tibia 112. In exemplary form, the posterior chamfer angle 122A of a TKA may coincide with the mid-flexion angle of the knee joint 108 (e.g., approximately 45 degrees between the femur 110 and tibia 112). By way of example, the posterior chamfer cut 122 may be angled approximately 45 degrees from the femoral canal axis 124. Determination of the posterior chamfer angle 122A with respect to a fixed axis (such as the femoral canal axis 124, also known as the femoral intramedullary canal) allows a surgeon to know the angle that the distal femur 110 should be orientated with respect to the proximal tibia 112 so that the posterior chamfer cut 122 can be made first. If, for instance, the posterior chamfer angle is 45 degrees, then the distal femur 110 may be repositioned by the surgeon to be angled at approximately 45 degrees with respect to the proximal tibia 112. In this fashion, some example TKA procedures according to at least some aspects of the present disclosure may involve making a posterior chamfer cut 122 as the first resection cut to the distal femur 110.

Figure 7B:
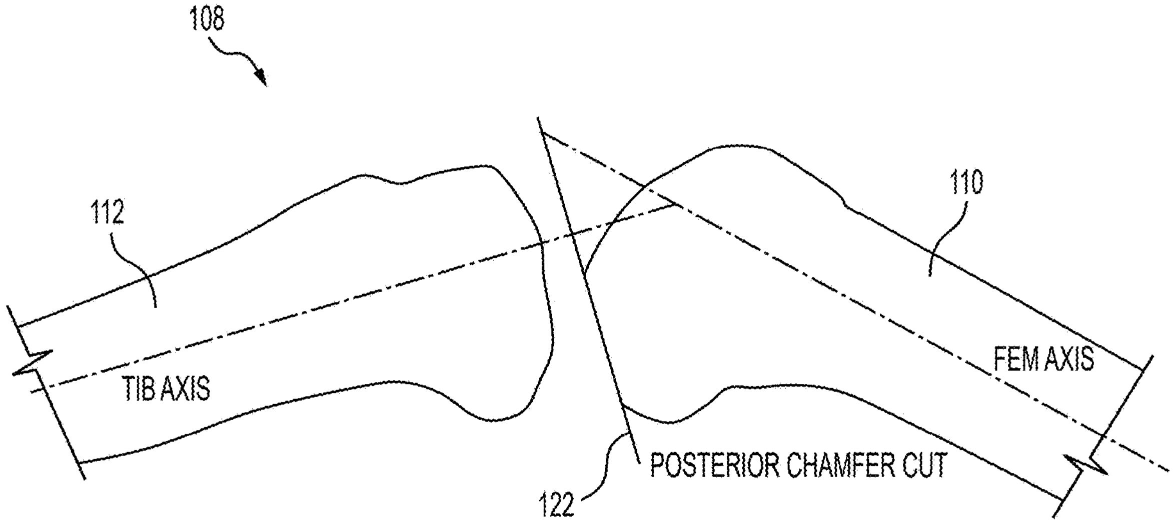
Figure 7C:
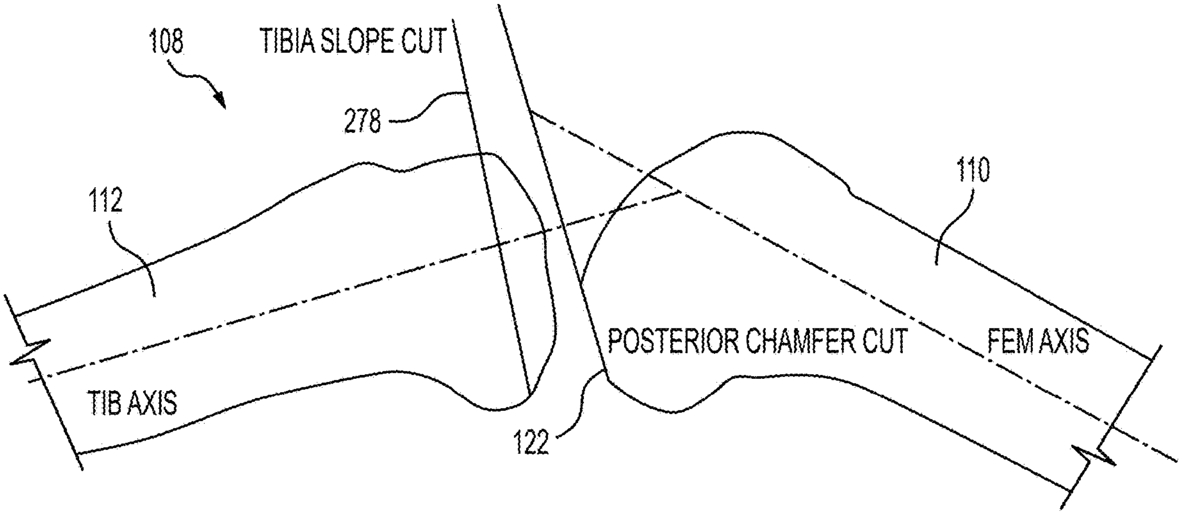
Figure 7D:
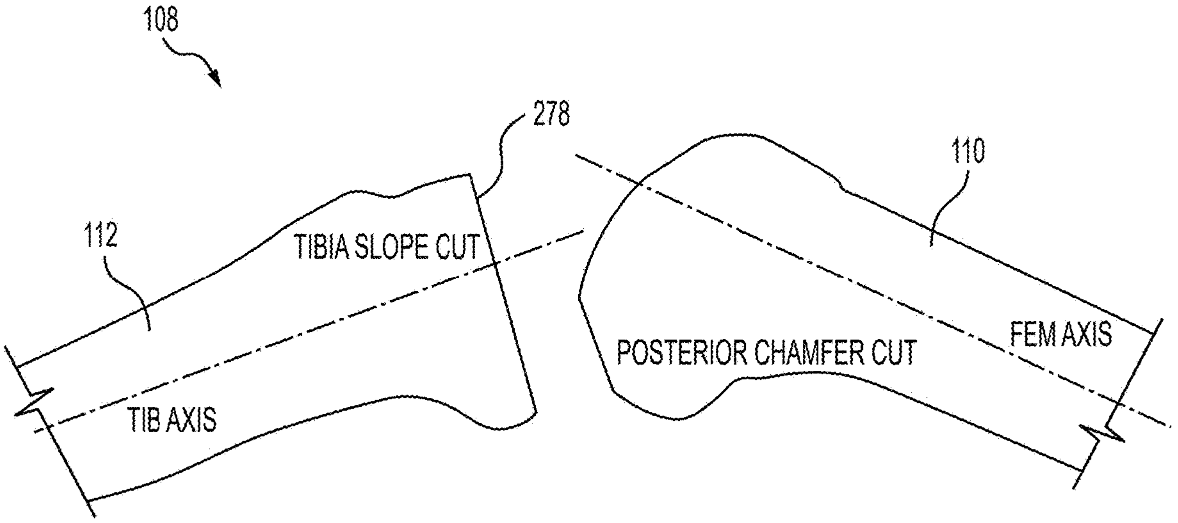
Figure 7E:
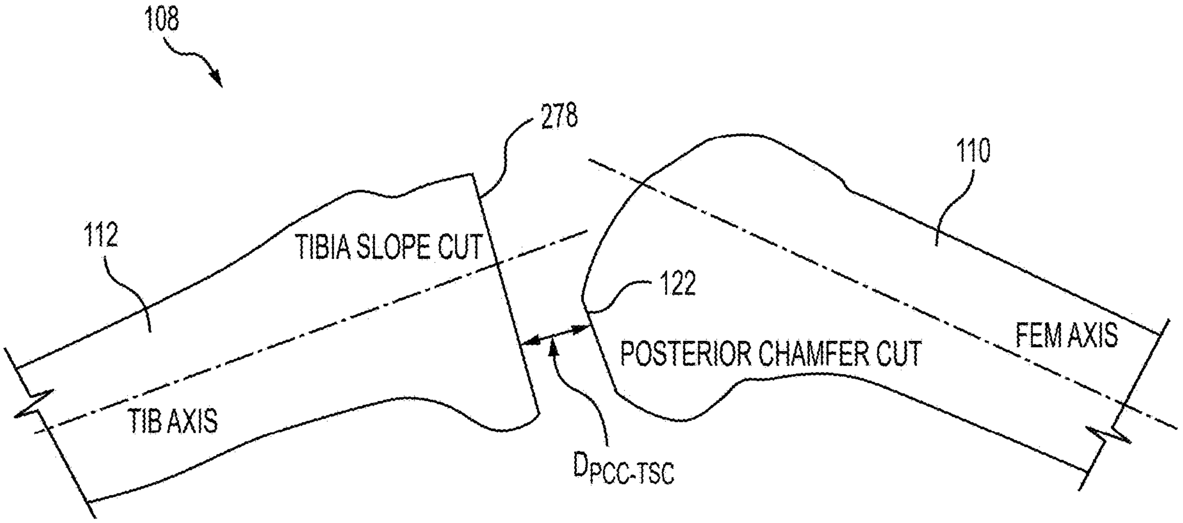

Referring to FIG. 7B, with the knee 108 balanced at the desired mid-flexion angle, the posterior chamfer cut 122 is made. Referring to FIG. 7C, the location and orientation of tibial plateau cut 278 is determined, such as by balancing the knee 108 with reference to the posterior chamfer cut 122. Referring to FIG. 7D, the tibial plateau cut 278 is performed. Referring to FIG. 7E, a distance between the posterior chamfer cut 122 and the tibial plateau cut 278 is determined.

In some alternative methods, the tibial plateau cut 278 may be made first. Then, the posterior chamfer cut 122 may be made, such as by balancing the knee 108 with reference to the tibial plateau cut 278. In some such methods, although the posterior chamfer cut 122 may be made after the tibial plateau cut 278, the posterior chamfer cut 122 may be the first cut on the femur 110.

Figure 7F:
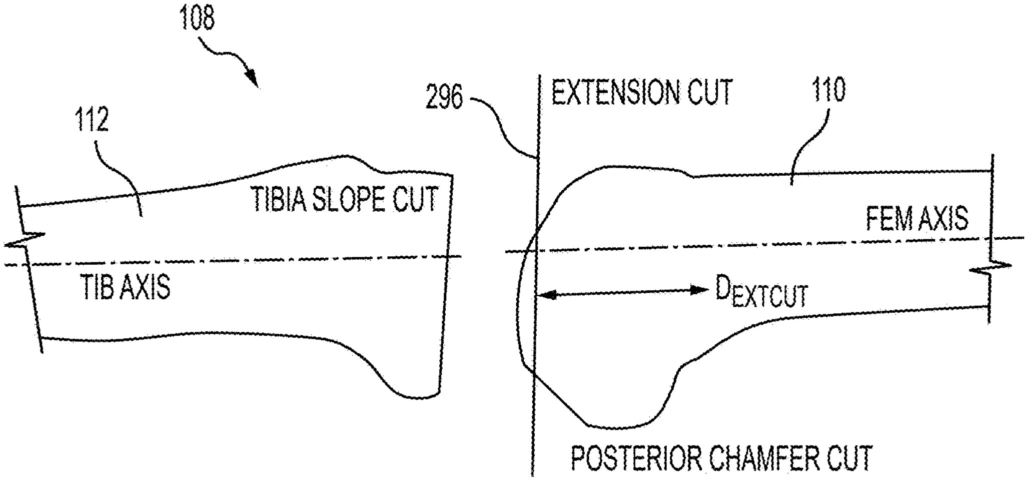
Figure 7G:
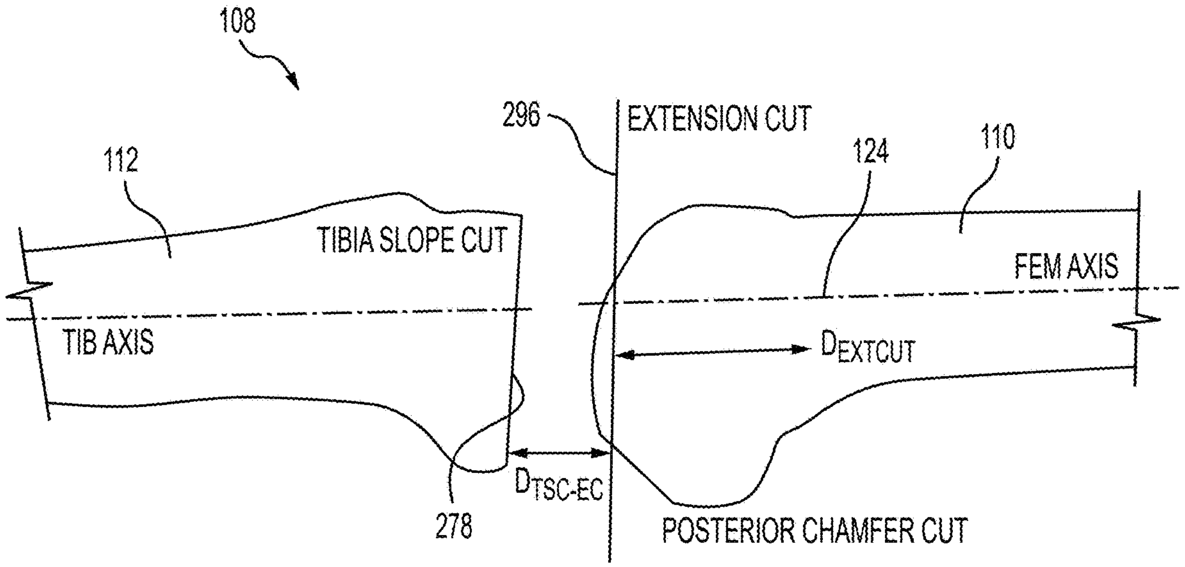
Figure 7H:
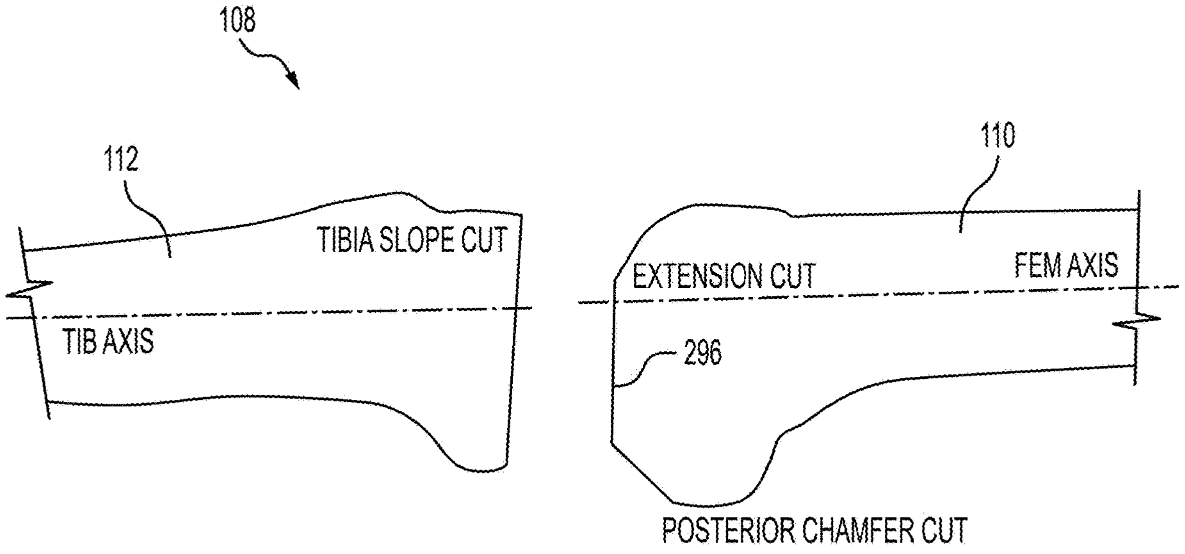

Referring to FIG. 7F, the knee 108 is positioned in full extension. The location and orientation of a femoral extension cut 296 is determined. Referring to FIG. 7G, the distance between the tibial plateau cut 278 and the femoral extension cut 296 may be matched to the distance between the posterior chamfer cut 122 and the tibial plateau cut 278 (FIG. 7E), such as by selecting the location of the femoral extension cut 296 along the femoral canal axis 124 that yields the desired geometry. Referring to FIG. 7H, the femoral extension cut 296 is performed. In various example methods, additional measurements, balancing, and/or cuts may be performed to prepare the knee 108 to receive the implant trials and orthopedic implants.

Figure 8:
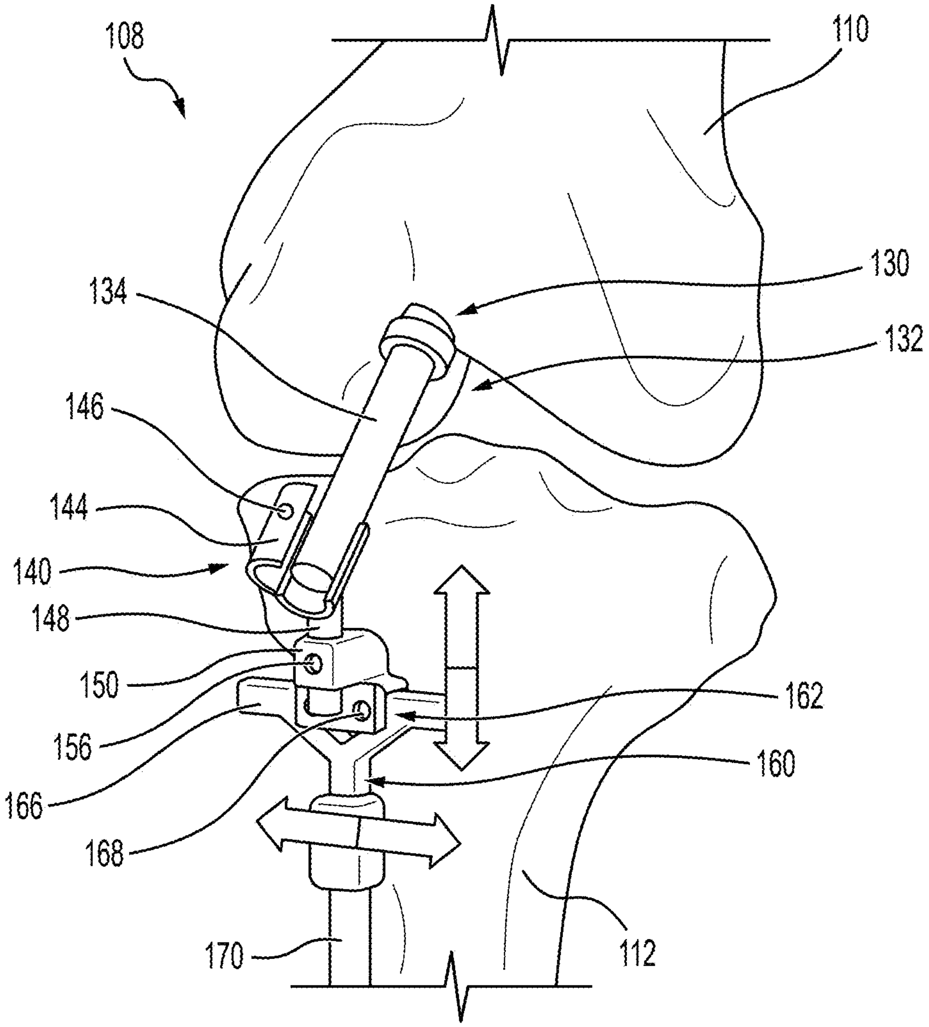
FIG. 8 is a perspective view of a femoral intramedullary rod mated with a receiving device of an example knee balancing jig.
Figure 9:
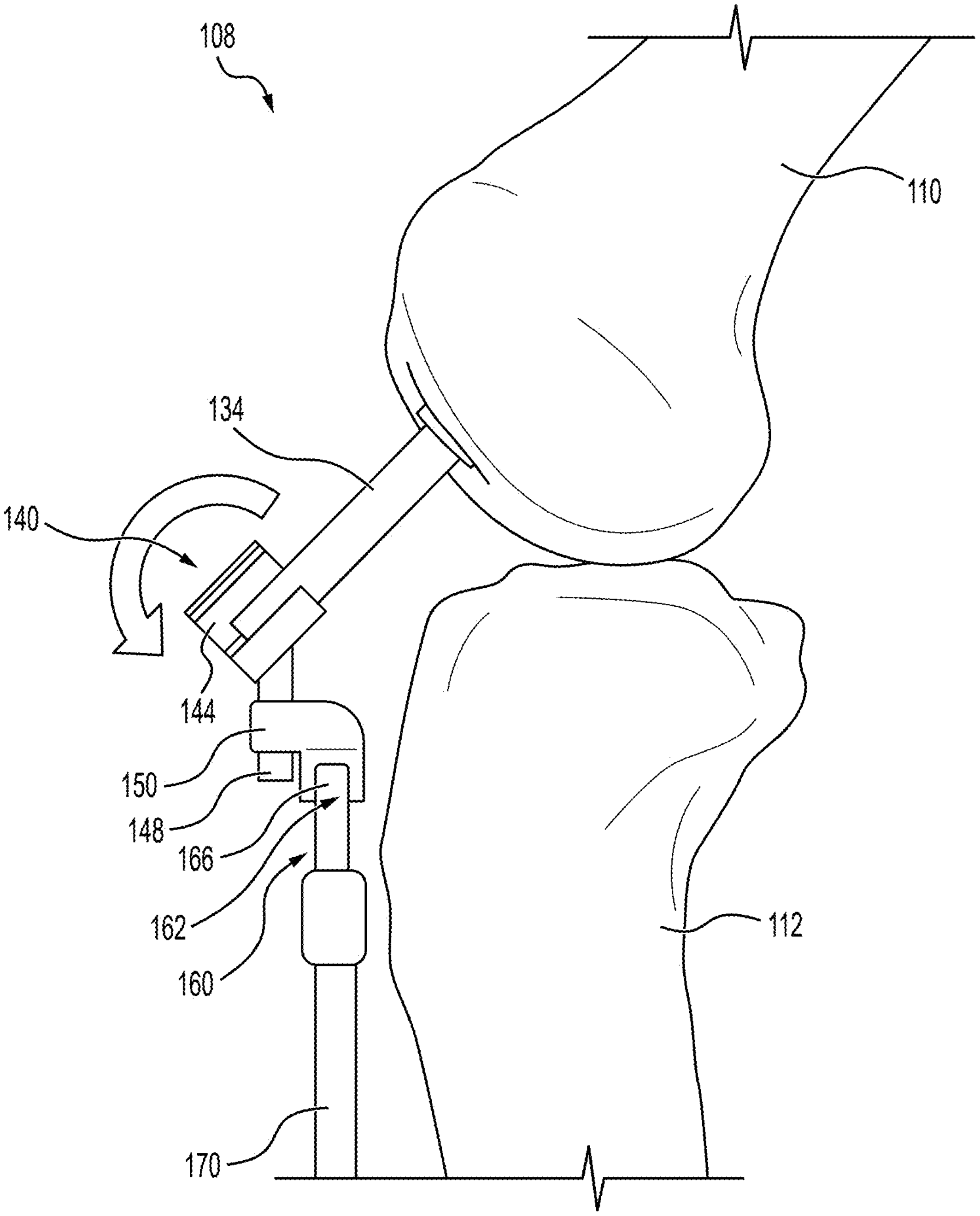
FIG. 9 is a lateral view of the femoral intramedullary rod mated with the receiving device of the knee balancing jig.

FIG. 8 is a perspective view of a femoral intramedullary rod mated with a receiving device of an example knee balancing jig, and FIG. 9 is a lateral view of the femoral intramedullary rod mated with the receiving device of the knee balancing jig, all according to at least some aspects of the present disclosure. Referring to FIGS. 7A, 7B, 8, and 9, making the posterior chamfer cut 122 can be accomplished in a number of ways. By way of example, an opening 130 is drilled into the distal femur 110 just above the top of the femoral intercondylar notch 132 so that a drill bit (not shown) performing the bone removal to create the opening is coaxial with the femoral canal axis 124 in both coronal (anterior view) and sagittal planes (lateral view). After the opening 130 is drilled, an intramedullary rod 134 is inserted into the opening 130 and seated to be secured within the opening, with a portion of the intramedullary rod 134 extending distally from the femur 110. In exemplary form, the intramedullary rod 134 includes a straight longitudinal shape with a circular cross-section normal to the straight shape.

In various example embodiments, the intramedullary rod 134 may have a cross-section that is round, oval, square, rectangular or any shape suitable for mating with other components as described below. The intramedullary rod 134 may include a stop device that will come flush with the femoral bone on the outer surface of the intramedullary canal so that the whole rod 134 doesn't sink into the intramedullary canal. Therefore, when this stop device comes flush with the bone, a portion of the intramedullary rod will protrude outward. In some alternative example embodiments, an extramedullary rod may be substituted for the intramedullary rod 134.

A femoral placement guide 140 engages the intramedullary rod 134 and is used to properly locate various components throughout the remainder of the TKA procedure. In exemplary form, the placement guide 140 may include a receiving device comprising a cylindrical collar 144, which may be in the form of a hinged, catcher's-mitt-like receiver, or may be any shape that can receive the intramedullary rod 134 at a prescribed flexion angle. The collar 144 includes a cylindrical through bore sized to accommodate throughput of at least a portion of the intramedullary rod 134 distally extending from the femur 110 and is arranged to receive the rod 134 at the prescribed angle. By way of further example, the through bore is dimensioned with relatively tight internal circumference tolerances with respect to the outside circumference of the intramedullary rod 134 so that the rod freely slides with respect to the collar 144, but does not have enough play so that travel of the collar occurs along an axis angled greater than five degrees with respect to a longitudinal axis of the intramedullary rod. In exemplary form, the collar 144 may include a set screw 146 or other retainer to fix the longitudinal motion of the collar with respect to the intramedullary rod 134 when the desired position is reached.

In alternative embodiments, the receiving device or catcher's mitt may have any suitable shape that mates with the intramedullary rod. The receiving device 144 may have the same diametrical or dimensional shape as the intramedullary rod 134 or may be larger, allowing for some relative movement, if needed. For purposes of explanation, the motion of the collar 144 with respect to the intramedullary rod 134 will be described as angular motion along two axes, a Z-axis and a Y-axis perpendicular to the Z-axis.

In some alternative embodiments, one or more external femoral components may be utilized in place of or in addition to the intramedullary rod 134. For example, an extramedullary rod and/or an external clamping or positioning component may be used as an external femoral component.

Extending from the collar 144 is a shaped shaft 148. In this exemplary embodiment, the shaped shaft 148 may be repositionably or rigidly mounted to an exterior circumference of the collar 144 and may be angled with respect to the collar incorporating a predetermined angle. This shaft 148, if not rigid, may be rotatable along one or three directions and/or translate around one or three directions. In the illustrated embodiment, the predetermined angle may be between 35 and 55 degrees (e.g., about 45 degrees), for example, again depending on the implant and the implant chamfer angle. Other similar embodiments may be associated with other predetermined angles as described elsewhere herein, such as mid-flexion angles generally between 30 and 70 degrees of flexion. In any event, the shaped shaft 148 is generally straight and incorporates a shape that allows a follower 150 to traverse along the shaped shaft in a linear manner. In exemplary form, the shaped shaft 148 may include a constant rectangular cross-section or include other constant cross-sectional shapes that facilitate motion along a single axis.

By way of example, the follower 150 may include a first shaped opening sized to accommodate throughput of at least a portion of the shaped shaft 148. By way of further example, the opening is dimensioned with relatively tight internal tolerances with respect to the outside tolerances of the shaped shaft 148 so that the follower 150 freely slides with respect to the shaped shaft, but does not have enough play so that travel of the follower occurs along an axis angled greater than five degrees with respect to a longitudinal axis of the shaped shaft. In this fashion, interaction between the shaped shaft 148 and follower 150 provides adjustment in only one of three axes. For purposes of explanation, the vertical motion of the follower 150 with respect to the shaped shaft 148 will be described as motion along the Y-axis. In a case where the shaped shaft 148 is rectangular in cross-section, the first shaped opening may be correspondingly rectangular in cross-section or otherwise bounded on the periphery to constrain motion of the shaped shaft to occur along only a single axis. In some example embodiments, these components could also allow for rotation around one or more axis and then, once positioned correctly, could be locked to achieve the proper angle.

In exemplary form, the follower 150 may include a set screw 156 or other retainer to fix the vertical motion of the follower with respect to the shaped shaft 148 when the desired vertical position and/or orientation is reached. As will be discussed in more detail hereafter, the relative position of the femoral placement guide 140, the follower 150, and a tibial placement guide 160 are fixed relative to one another after achieving balancing of the knee joint at or proximate mid-flexion.

In this exemplary embodiment, the follower 150 also includes a second shaped opening 162 sized to accommodate throughput of at least a portion of a beam 166 of the tibial placement guide 160. By way of further example, the opening 162 is dimensioned with relatively tight internal tolerances with respect to the outside tolerances of the beam 166 so that the follower 150 freely slides with respect to the beam, but does not have enough play so that travel of the follower occurs along an axis angled greater than five degrees with respect to a longitudinal axis of the beam. In this fashion, interaction between the beam 166 and follower 150 provides adjustment in only one of three axes. For purposes of explanation, the horizonal motion of the follower 150 with respect to the beam 166 will be described as motion along an X-axis, where the X-axis is perpendicular to the Y-axis and concurrently perpendicular to the Z-axis. In other words, the motion of the follower 150 along the beam 166 occurs along an axis that is perpendicular to an axis along which the follower 150 traverses with respect to the shaped shaft 148. In a case where the beam 166 is rectangular in cross-section, the second shaped opening 162 may be correspondingly rectangular in cross-section or otherwise bounded on the periphery to constrain motion of the beam to occur only along a single axis, the X-axis.

In exemplary form, in addition to the beam 166, the tibial placement guide 160 may be disposed on a tibial reference, such as a cylindrical rod 170, which may include an extramedullary tibial rod, extending perpendicularly from the beam. In the illustrated embodiment, the tibial placement guide 160 mounted to the rod 170 generally anterior to the knee 108 so that the beam 166 is oriented generally in a medial-lateral orientation. When the tibial placement guide 160 is properly aligned, the cylindrical rod 170 may extend substantially parallel to the tibial longitudinal axis 174 and/or may be secured to the patient's lower leg.

The adjustability of the receiving device 144 relative to the tibial rod 170 may allow for translation and orientation changes so that the retrieving device can properly mate with the femoral rod 134. As shown in the figures, various components may be installed on and removed from the tibial placement guide 160 as needed throughout an example TKA procedure. Additionally, it should be understood that, for clarity and ease of view, some of the figures herein may not include components that may remain in place from step to step in some example procedures.

In practice, after the opening 130 is drilled into the distal femur 110 and the intramedullary rod 134 is inserted therein, a portion of the intramedullary rod extends distally from the femur. The femoral placement guide 140 is then repositioned so that the collar 144 traverses along the intramedullary rod 134. Thereafter, during, or before placing the collar 144 around the intramedullary rod 134, the follower 150 is positioned to traverse along the shaped shaft 148, in addition to the follower engaging and traversing along the beam 166. In exemplary form, the component parts of the femoral placement guide 140 and the tibial placement guide 160 allow for repositioning of the component parts so that the cylindrical rod 170 is positioned adjacent the tibial tubercle and parallel to the tibial longitudinal axis 174, while the collar 144 circumscribes the intramedullary rod 134. After reaching this arrangement, the component parts are secured to one another so that the collar 144 is fixed in position with respect to the intramedullary rod 134 (such as by tightening the set screw 146), and the follower 150 is fixed in position with respect to the shaped shaft 148 (such as by tightening the set screw 156). By securing in fixed position the femoral placement guide 140 with respect to the intramedullary rod 134, motion of the femoral placement guide 140 along the Z-axis is in inhibited. Likewise, by securing in fixed position the femoral placement guide 140 with respect to the follower 150, motion of the follower along the Y-axis is inhibited. The follower 150 is secured with respect to the beam 166 using one or more set screws 168, for example.

Figure 10A:
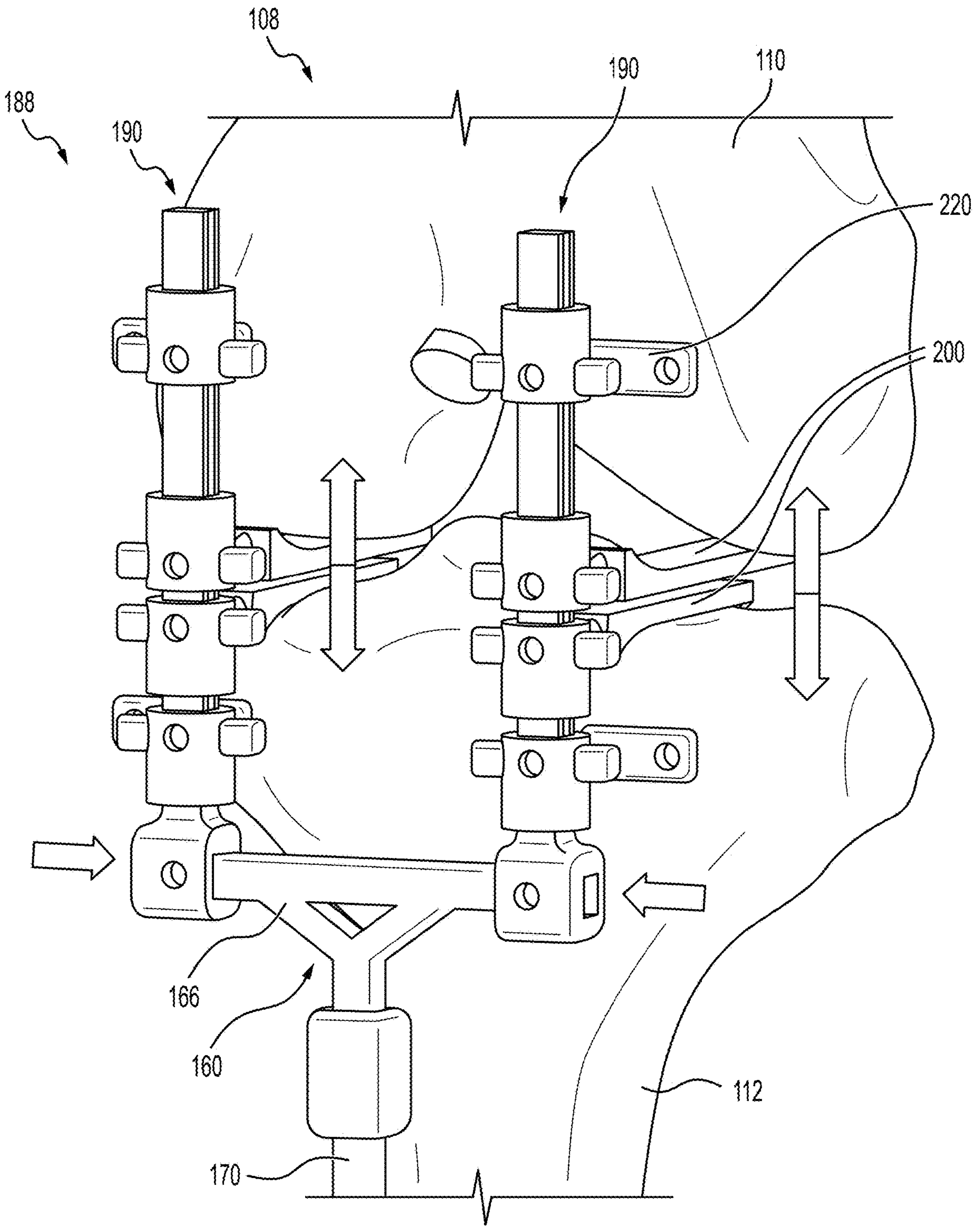
FIG. 10A is a perspective view of the example knee balancing jig with balancing assemblies installed in use on a knee joint.
Figure 10B:
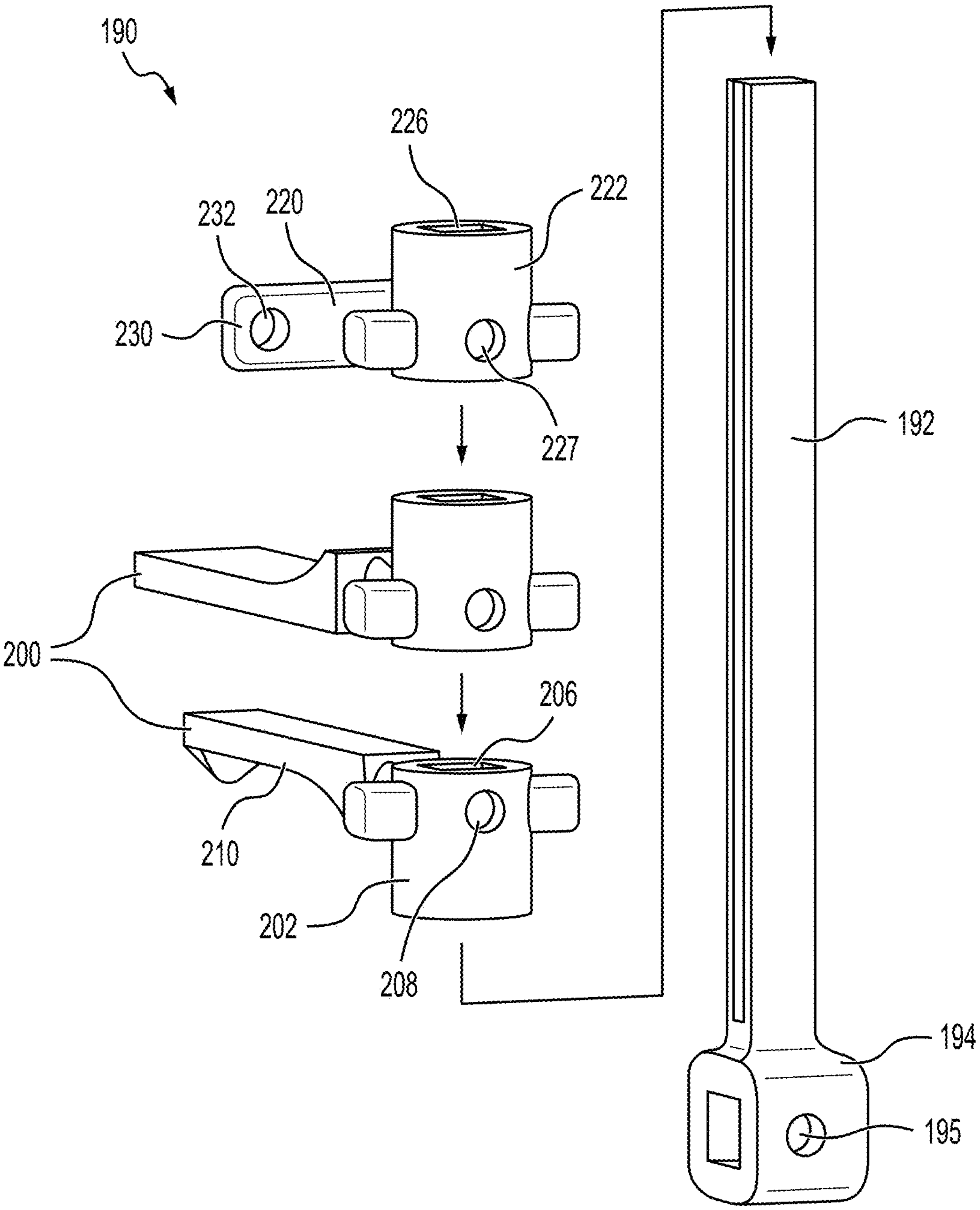
FIG. 10B is an exploded perspective view of an example balancing assembly.
Figure 10C:
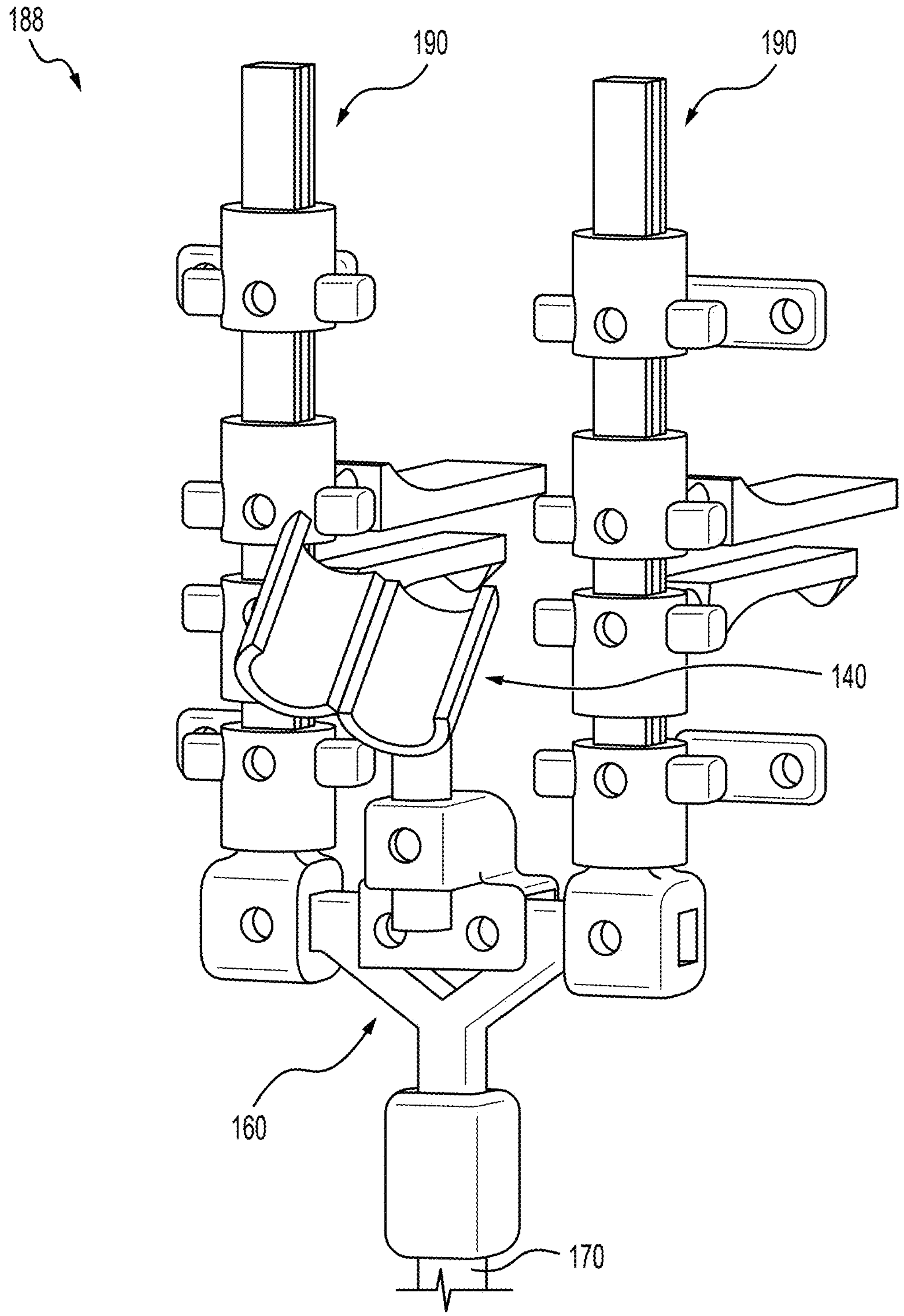
FIG. 10C is a perspective view of the example knee balancing jig with the receiving device and the balancing assemblies installed.

FIG. 10A is a perspective view of an example knee balancing jig 188 with balancing assemblies 190 installed in use on a knee joint 108, and FIG. 10B is an exploded perspective view of an example balancing assembly 190, and FIG. 10C is a perspective view of the example knee balancing jig with the receiving device and the balancing assemblies installed, all according to at least some aspects of the present disclosure. Although the knee balancing jig 188 may be configured for and/or used at any flexion angle, its use is described below in connection with an example mid-flexion balancing approach.

In exemplary form, the knee balancing jig 188 is initially used in connection with making the posterior chamfer cut 122 on the femur 110. With the knee 108 secured at the desired initial flexion angle, such as using the receiving device 140 and the intramedullary rod 134 and/or external fixation, the balancing jig 188 is used to balance the ligaments. In the illustrated embodiment, the knee is held in mid-flexion—at about 45 degrees of flexion—which corresponds to the proper chamfer angle for the intended implant. In other embodiments, the mid-flexion position may be between about 30 degrees and about 75 degrees of knee flexion, for example. As alternative femoral component designs may have different chamfer angles, in some embodiments the receiving device 140 may be adjustable to rotate to a proper angle corresponding with the femoral component chamfer angle.

Figure 9A:
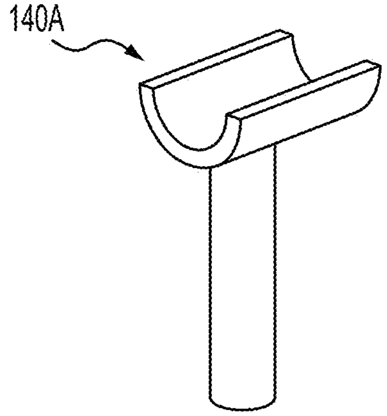
FIG. 9A is a perspective view of an alternative receiving device 140A configured for about 90 degrees of flexion.
Figure 9B:
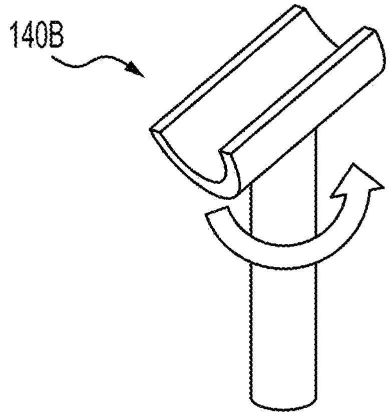
FIG. 9B is a perspective view of an alternative receiving device 140B configured for about 60 degrees of flexion.
Figure 9C:
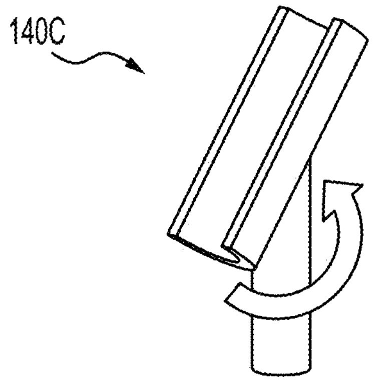
FIG. 9C is a perspective view of an alternative receiving device 140C configured for about 30 degrees of flexion.

In some embodiments, the receiving device 140 may be modular and/or removable/replaceable on the balancing jig 188, and a plurality of receiving devices 140 corresponding to different chamfer angles may be provided. FIG. 9A is a perspective view of an alternative receiving device 140A configured for about 90 degrees of flexion, FIG. 9B is a perspective view of an alternative receiving device 140B configured for about 60 degrees of flexion, and FIG. 9C is a perspective view of an alternative receiving device 140C configured for about 30 degrees of flexion, all according to at least some aspects of the present disclosure. Generally, if the chamfer angle is 45 degrees, then the receiving device 140 that will be used by the surgeon may be angled at a fixed angle of 45 degrees. Alternatively, for other chamfer angles, an appropriate receiving device 140A, 140B, 140C may be selected and used. Further, other positioning devices can also be used, such as an external brace or external positioner.

In some example procedures, the intramedullary rod 134 may be removed from the femur 110 and removed from the collar 144. In addition, the femoral placement guide 140 and the follower 150 may be disengaged from the tibial placement guide 160, thus leaving the tibial placement guide 160 mounted with respect to the tibia and retained in position via the tibial extramedullary rod 170. Knee position may be maintained using external fixation, for example. In other example procedures, the intramedullary rod 134 and receiving device 140 may remain in place and/or may be used to maintain the position of the knee.

Referring to FIGS. 10A-10C, an example knee balancing jig 188 may include a pair of balancing assemblies 190 mounted to the beam 166, with one balancing assembly 190 disposed generally medially (e.g., for use on the medial condyle) and the other balancing assembly being disposed generally laterally (e.g., for use on the lateral condyle). In exemplary form, a balancing assembly 190 may include a vertical guide 192 having a rectangular cross-section. It should be noted that the cross-section of the vertical guide 192 may differ from that of a rectangular cross-section and include any other shape (e.g., triangular, rounded, four or more sided, etc.) repetitively reproduced vertically to maintain a constant or near constant horizontal cross-section. In this exemplary embodiment, the vertical guide 192 is configured to releasably mount to the tibial placement guide 160 in a generally inferior-superior orientation. For example, in the illustrated embodiment, the vertical guide 192 includes an adapter 194 configured to engage the beam 166 and retain the three-dimensional position of the vertical guide with respect to the beam. In the illustrated embodiment, the adapter is releasably secured to the beam 166 using a set screw. Both sides are opened so that medial/lateral sliding can occur.

One exemplary component of the balancing assembly 190 may include a paddle 200, which may extend generally posteriorly relative to the vertical guide 192. By way of example, a balancing assembly 190 may include one or more paddles 200, such as a superior paddle and an inferior paddle. As will be discussed in more detail hereafter, one or more paddles 200 may be utilized to measure the spacing between the tibia 112 and femur 110. In exemplary form, a paddle 200 may include a connector 202 configured to engage the vertical guide 192 and allow for selective vertical repositioning of the paddle with respect to the vertical guide. By way of example, the connector 202 may include an opening or cavity 206 resembling the cross-section of the vertical guide 192, but slightly larger to accommodate throughput of the vertical guide. The connector 202 may also include a set screw 208 or spring-loaded projection that extends into the cavity 206 and it used to selectively secure the paddle 200 to the vertical guide 192. Extending from the connector 202 is a blade 210 that, in exemplary form, has a dominant longitudinal dimension extending away from the connector, and a rectangular profile from both horizontal and vertical directions. By way of example, the blade 210 may embody a cuboid shape. Other shapes can be used such as spoons or even pre-operative derived shapes that mimic the shape of each condyle. This may be accomplished with pre-operative imaging. Another shape could be a rectangular shape. In some example embodiments, the blade 210 may be quite thin, while being sufficiently rigid to perform the balancing functions described herein. The shape could also be patient specific based on the shape of the patient's condyles.

While not required, the vertical dimension (i.e., thickness) of the paddle 200 may be constant along its longitudinal length. Moreover, while not required, the horizontal widthwise dimension across the entire paddle 200 may be constant. Further, while not required, the horizontal length across the paddle 200 may be constant. Still further, while not required, the uppermost and bottommost surfaces of the blade 210 and the connector 202 may be coplanar with one another. In this manner, measurements involving the uppermost or bottommost surface of the blade 210 can be readily utilized.

Another exemplary component of the balancing assembly 190 may be one or more pin guides 220. By way of example, the pin guide 220 may include a connector 222 configured to engage the vertical guide 192 and allow for selective vertical repositioning of the pin guide with respect to the vertical guide. By way of example, the connector 222 may include an opening or cavity 226 resembling the cross-section of the vertical guide 192, but slightly larger to accommodate throughput of the vertical guide. The connector 222 may also include a set screw 227 or spring-loaded projection that extends into the cavity 226 and is used to selectively secure the pin guide 220 to the vertical guide 192. Extending from the connector 222 is a pin flange 230 that, in exemplary form, includes an opening 232 configured to receive throughput of at least one of a drill bit and a bone pin as described below.

While not required, the vertical dimension (i.e., thickness) of the pin guide 220 may be constant. In this manner, measurements at the uppermost or bottommost surface of the pin flange 230 can be readily utilized.

Turning specifically to FIG. 10A, in use, prior to mounting the vertical guides 192 to the beam 166, each vertical guide may have mounted thereto a pair of paddles 200 and a pin guide 220. In exemplary form, the paddles 200 mounted to each vertical guide 192 are oriented to overlap one another so that the medial vertical guide 192 has its paddles orientated to interpose the femoral medial condyle articular surface and the medial tibial condyle receiver articular surface. Similarly, the lateral vertical guide 192 has its paddles orientated to interpose the femoral lateral condyle articular surface and the lateral tibial condyle receiver articular surface.

While the knee joint 108 is bent at approximately 45 degrees or another desired mid-flexion angle (e.g., the same angle of the posterior chamfer cut angle) and retained in position (such as by using an external brace, not shown), the surgeon performs a soft tissue balance for the medial and lateral sides of the knee. As part of this soft tissue balance, the surgeon manipulates the spacing between the overlapping paddles 200 on both the medial and lateral sides until reaching the desired balance. After reaching the desired balance on the medial and lateral sides, the surgeon records the spacing of the paddles on both sides (medial and lateral) such as by using the position of the paddles 200 with respect to the vertical guide 192. In cases where the vertical guides 192 include measurement markings, these markings may be utilized to record the spacing between the paddles 200 simply by using the position of the connectors 202 with respect to the vertical guides.

Figure 10D:
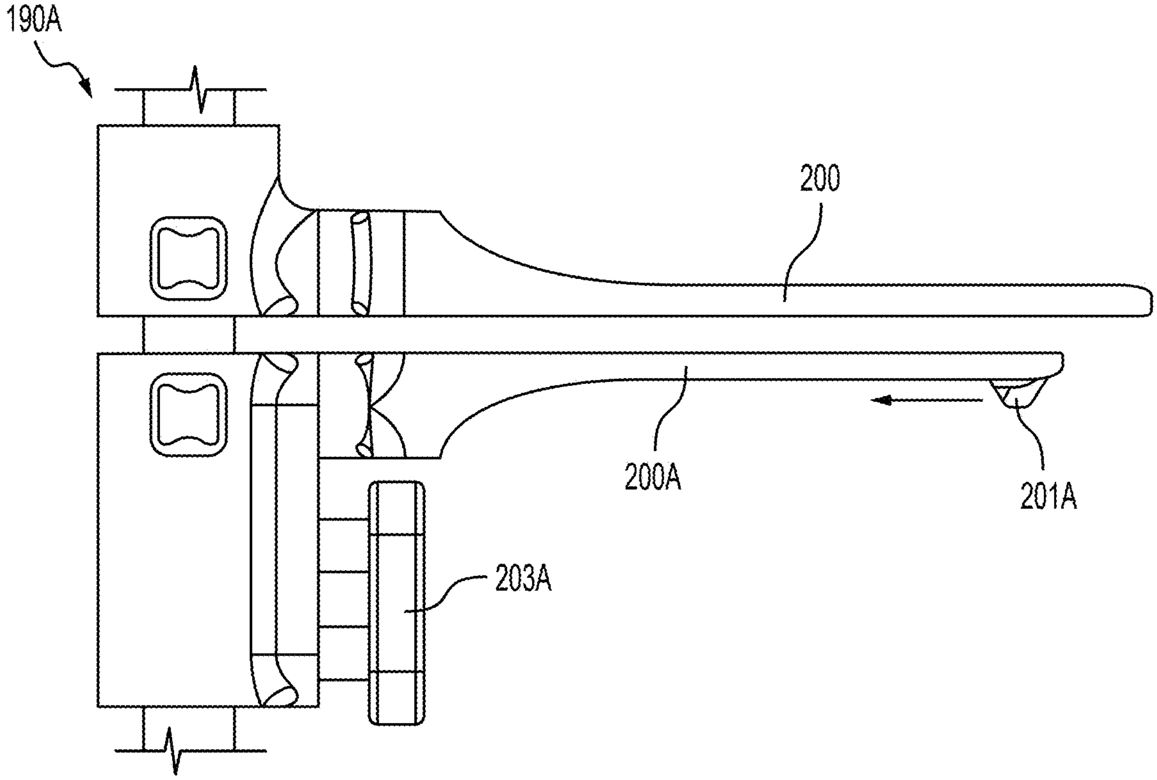
FIG. 10D is a lateral elevation view of an alternative example balancing assembly including an adjustable tibial element in a posterior position.
Figure 10E:
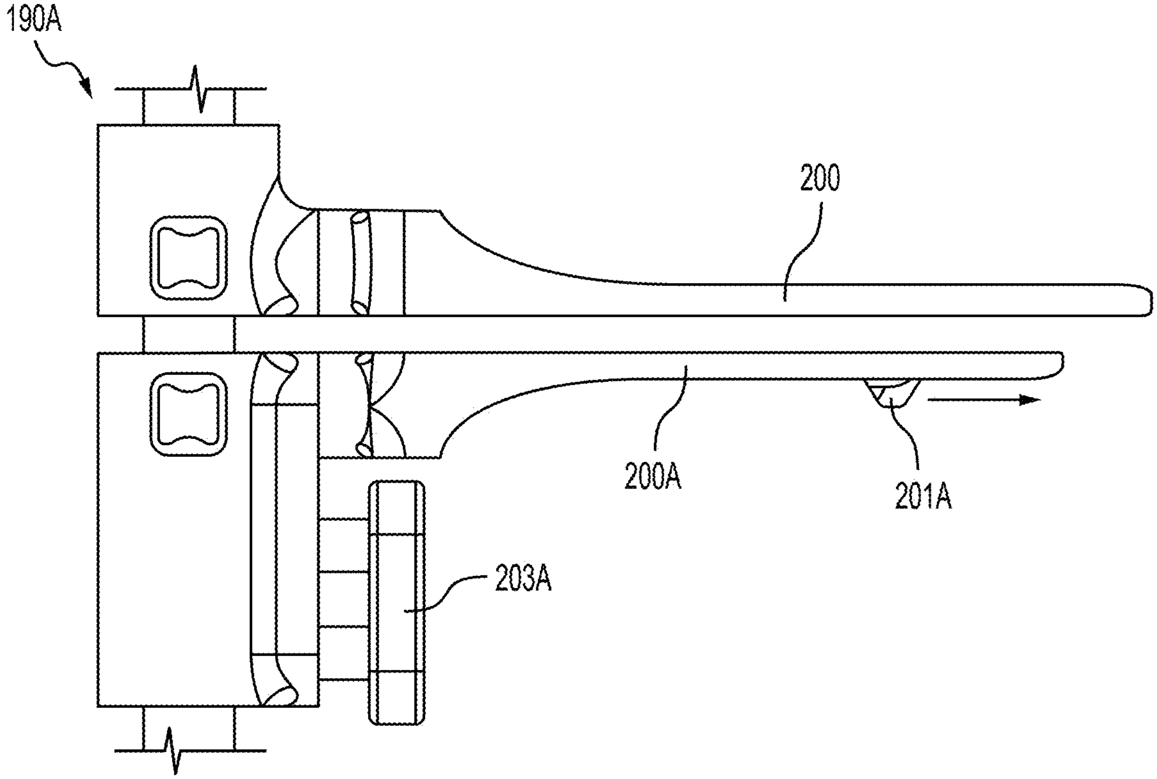
FIG. 10E is a lateral elevation view of balancing assembly of FIG. 10D with the adjustable tibial element in an anterior position.
Figure 10F:
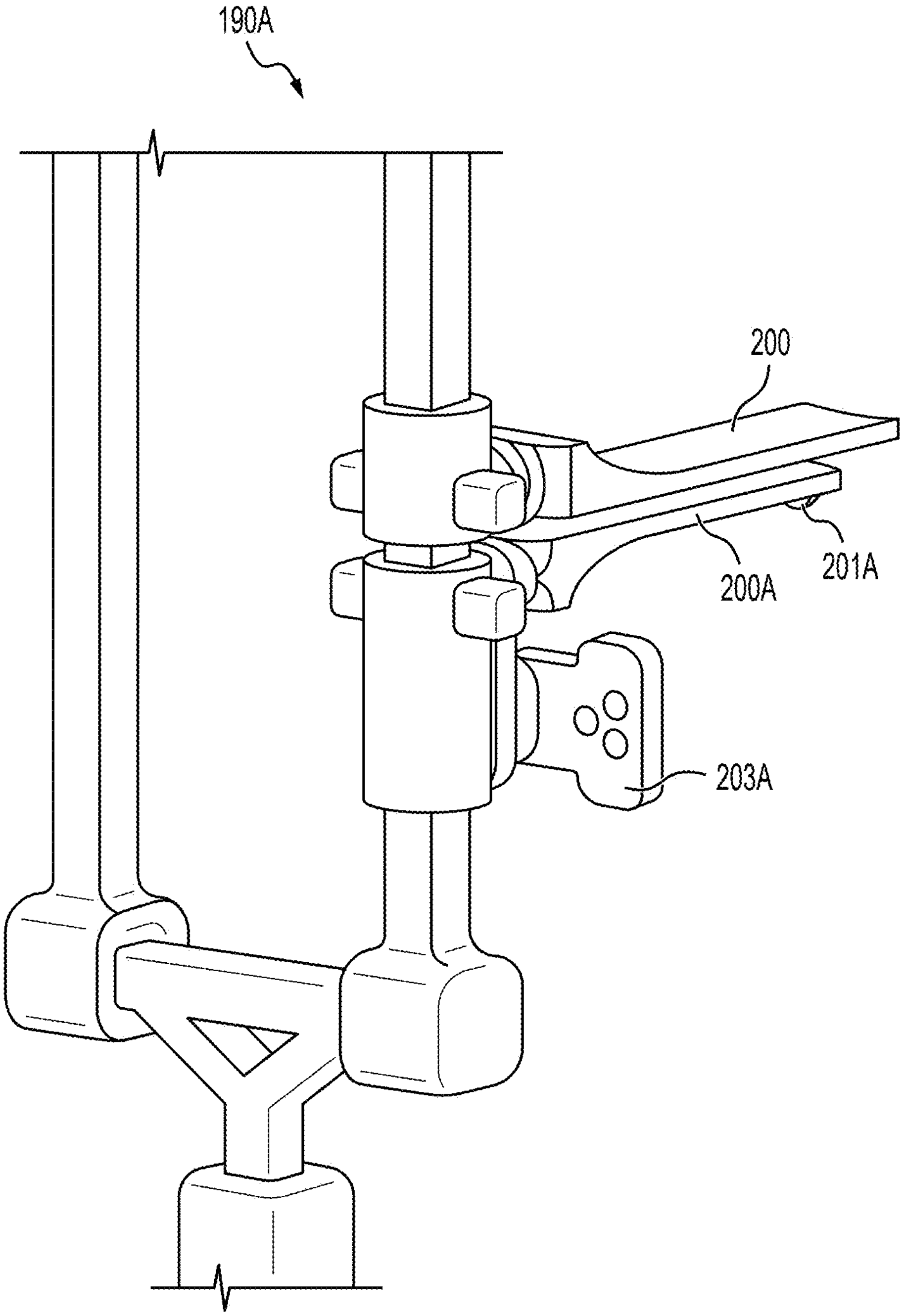
FIG. 10F is a perspective view of the example balancing assembly of FIGS. 10D and 10E.

In some embodiments, components that mate with bones may be adjustable to allow for different bone sizes. For example, the portion of a balancing assembly that mates with the tibial may be adjustable (e.g., in the anterior-posterior direction) for use with different sizes of tibias. FIG. 10D is a lateral elevation view of an alternative example balancing assembly 190A including an adjustable tibial element in a posterior position; FIG. 10E is a lateral elevation view of the balancing assembly 190A of FIG. 10D with the adjustable tibial element in an anterior position; and FIG. 10F is a perspective view of the example balancing assembly 190A of FIGS. 10D and 10E, all according to at least some aspects of the present disclosure. Various elements of the balancing assembly 190A are similar in structure and operation to corresponding components in other embodiments described herein, and repeated description is omitted for brevity. Further, features described in connection with the balancing assembly 190A may be utilized in connection with any other embodiment described herein. For example, generally similar adjustable femoral elements may be utilized in some embodiments.

In the balancing assembly 190A, one of the paddles 200A comprises an adjustable engagement feature 201A. In the illustrated embodiment, the engagement feature 201A is linearly repositionable generally in an anterior-posterior direction, such as between the posterior position illustrated in FIG. 10D and the anterior position illustrated in FIG. 10E. Accordingly, the tibial element may be adjusted to better fit a particular tibia. In the illustrated embodiment, the adjustable engagement feature 201A may be movable by operation of actuator 203A, which may be disposed on the connector 202A. For example, sliding and/or rotating the actuator 203A may cause the engagement feature 201A to traverse anteriorly and/or posteriorly along a track formed on the distal side of the paddle 200A.

Figure 11:
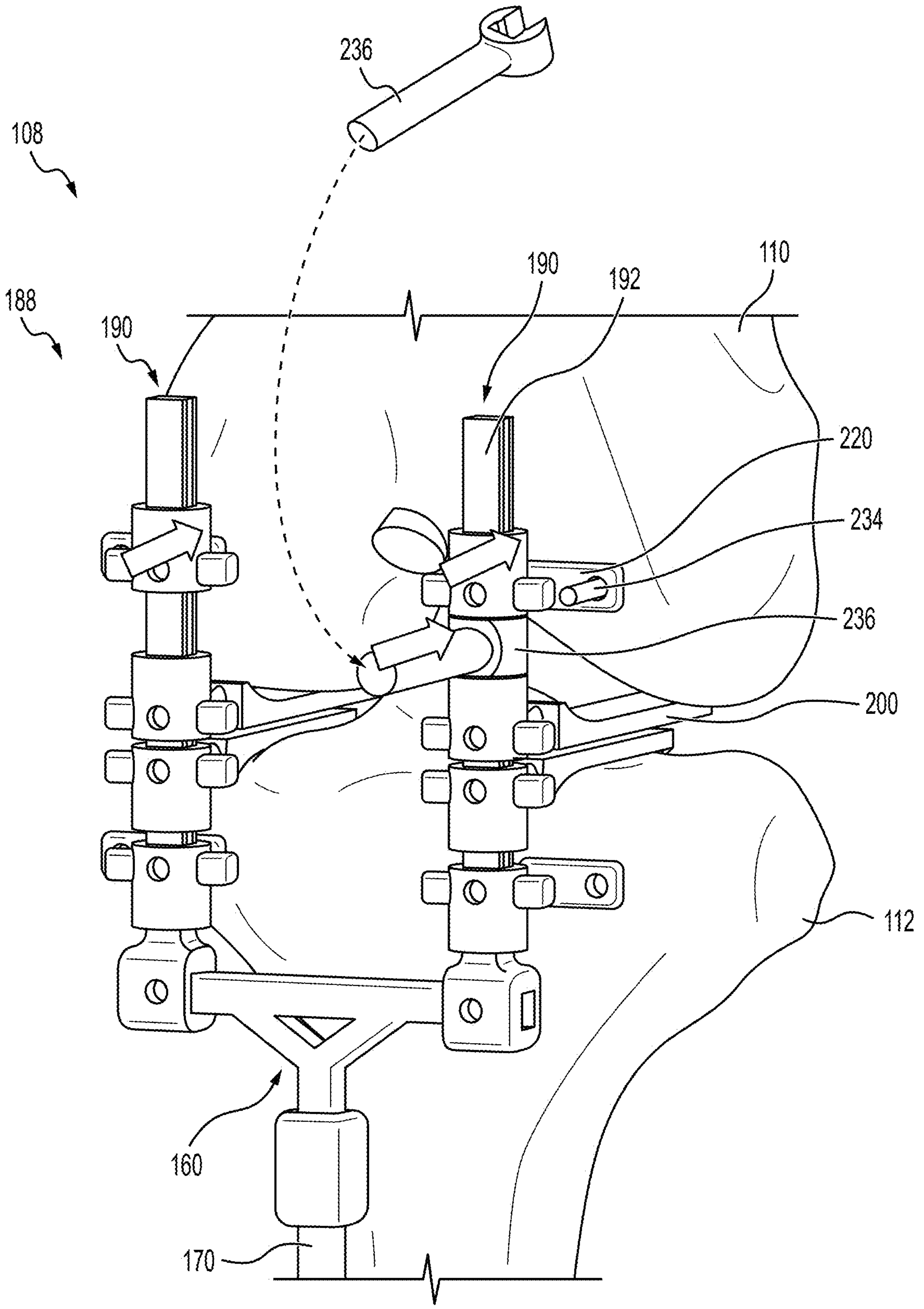
FIG. 11 is a perspective view of the balancing jig with a spacer establishing a femoral bone pin location.
Figure 12:
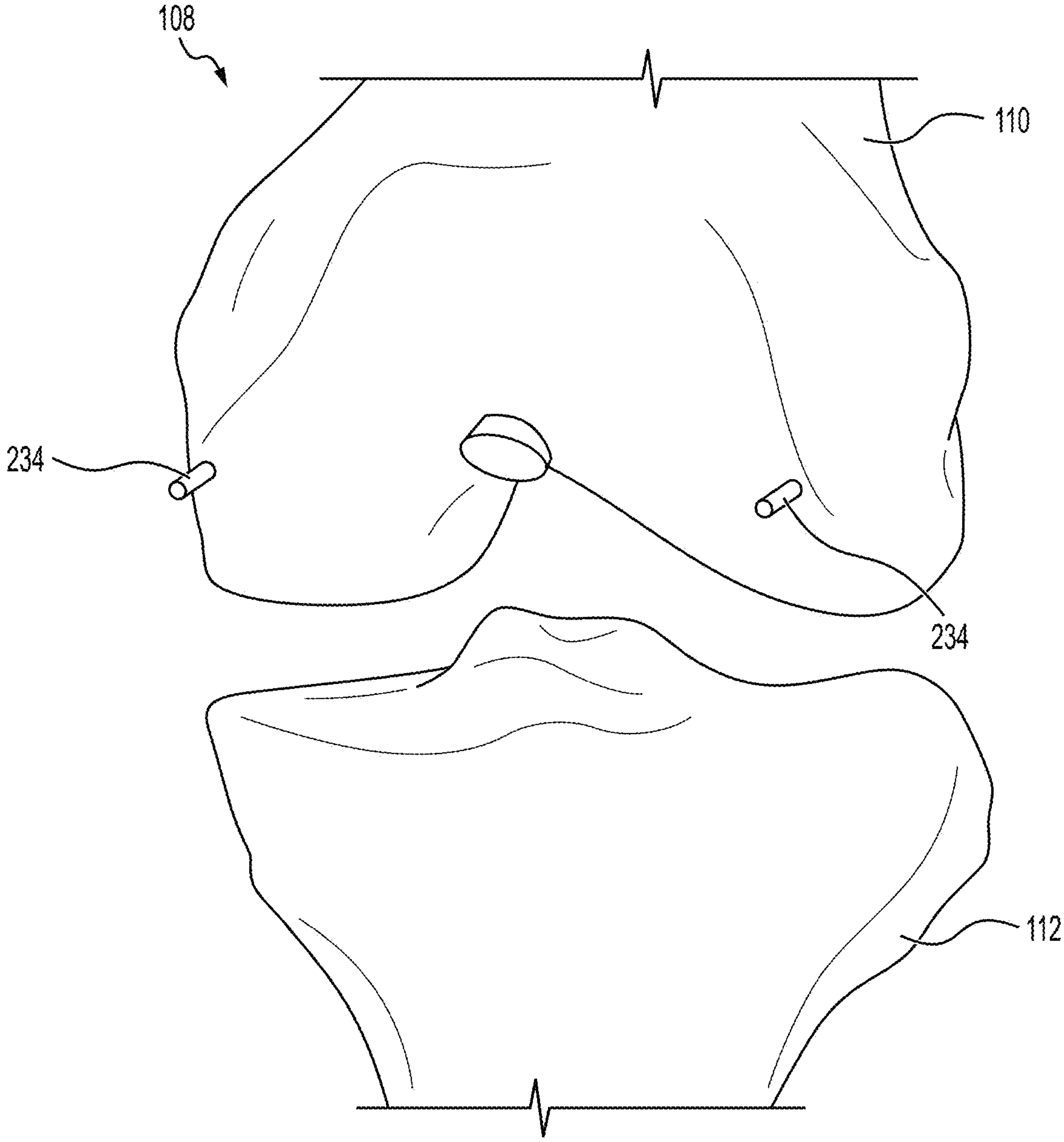
FIG. 12 is a perspective view of the knee with femoral bone pins installed.

FIG. 11 is a perspective view of the balancing jig 188 with a spacer 236 establishing a femoral bone pin location, and FIG. 12 is a perspective view of the knee with femoral bone pins installed, all according to at least some aspects of the present disclosure. After the desired balance is achieved, locations of one or more femoral bone pins 234 are determined. In the illustrated embodiment, a spacer 236 is positioned on the vertical guide 192 above and against the paddle 200 associated with one of the femoral condyles. Then, the respective pin guide 220 is positioned above and against the spacer 236. Thus, the spacer 236, having a known vertical dimension, locates the pin guide 220 at a known position relative to the paddle 200. A similar procedure is performed for the paddle 200 associated with the other femoral condyle. These steps of paddle distraction of the joint then allow pins to be placed in both the femur and the tibia that have a rectangular relationship for symmetric balancing or a trapezoid for asymmetric spacing based on ligament balance and predicated on standard TKA resection levels.

After the position of each pin guide 220 is finalized, a bone drill bit (not shown) is inserted through the opening 232 so that the walls of the flange 230 delineating the opening act as a guide for the drill bit. Two holes are drilled into the distal femur that are aligned with the respective openings 232. Thereafter, a pair of bone pins 234 are inserted through the respective openings 232 of the pin guide 220 and secured within the drilled femoral cavities. Post bone pin 234 placement, the remining components may be removed (pin guide 220, paddles 200, vertical guides 192, tibial placement guide 160), resulting in the configuration depicted in FIG. 12. The tibial guide and/or the EM rod can be removed for cutting bones or to reposition the leg. The guide and/or rod can be replaced at a later time to recreate the previously defined fixed relationship (for example the angle of the knee during the chamfer cut) between the femur and the tibia.

Initially balancing the ligaments at about the chamfer angle in mid-flexion may facilitate a desired ligament tension at mid-flexion positions. In some example embodiments, the knee balancing jig 188 may include one or more read-out devices configured to indicate the gap distance between the medial condyle to the medial tibial plateau and the lateral condyle to the lateral tibial plateau and/or tension in one or more ligaments. Generally, if a surgeon is gap balancing the goal will be to have these distance measurements to be equal or nearly equal. If a surgeon is attempting to anatomically balance or use a form of kinematic balancing, the gap distances for the medial and lateral condyles (and subsequently medial and lateral collateral ligaments) may be different. Either way, these values may be stored and/or recorded, such as for use as the future goal (or in calculations for future goals) for gaps and tensions at other flexion angles. In some example procedures, the mid-flexion readings may be used as the baseline as well as the desired gaps and tensions for that individual person's knee. As discussed above, mid-flexion may be an important flexion range for balancing and/or it may be easier for a surgeon to maintain this balance at full extension and 90 degrees of knee flexion.

Figure 36A:
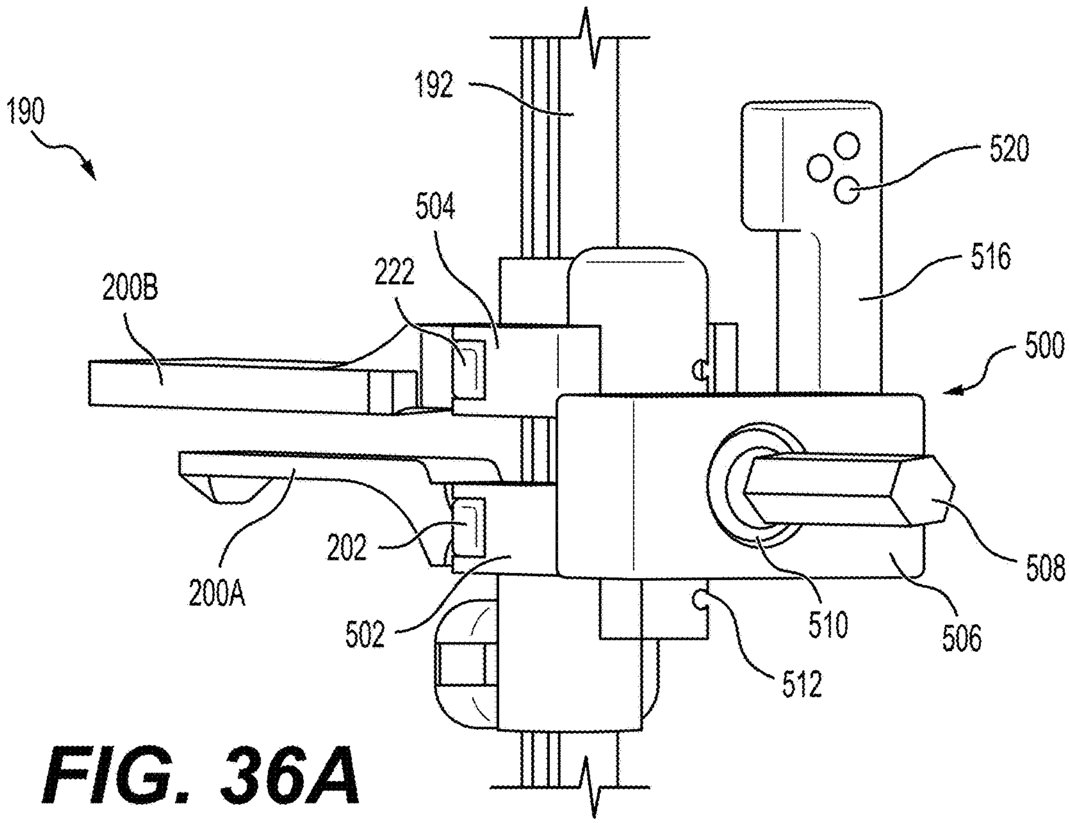
FIGS. 36A and 36B are perspective views illustrating an example gap tensioner disposed on a balancing assembly.
Figure 36B:
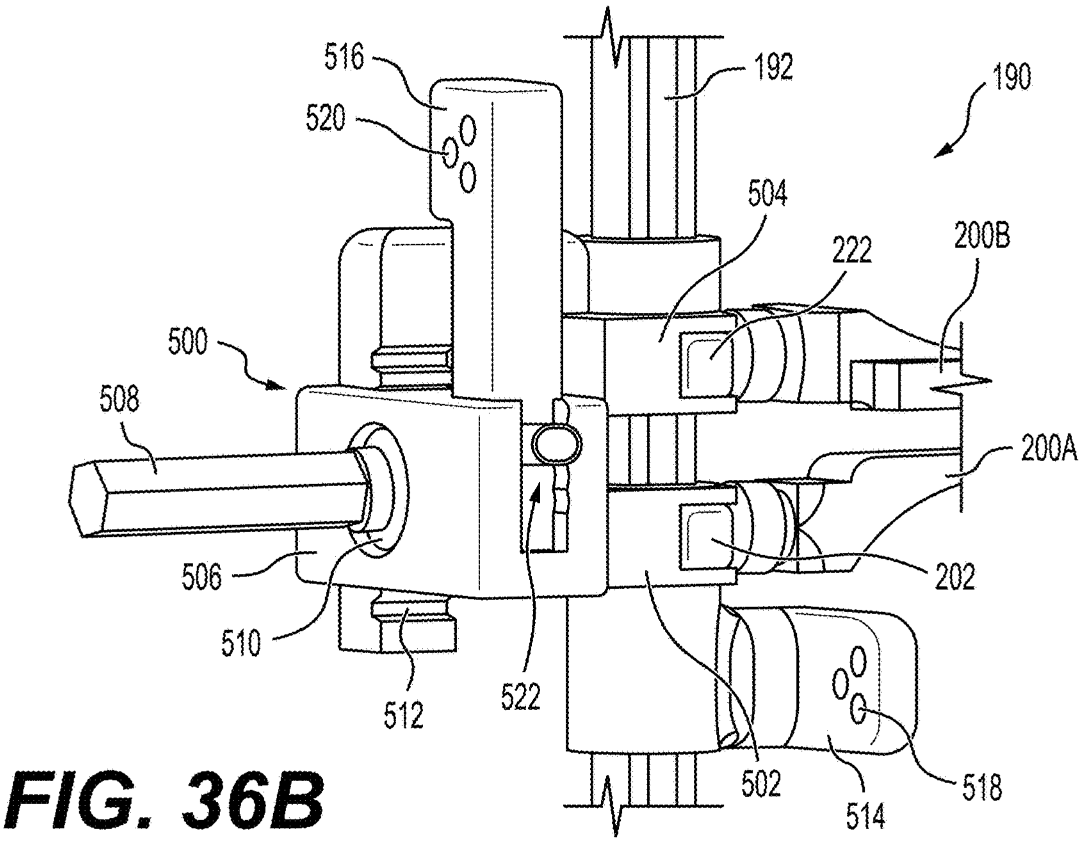

FIG. 36A is a perspective view of an example gap tensioner 500 disposed on a balancing assembly 190, and FIG. 36B is a perspective view of the gap tensioner 500, all according to at least some aspects of the present disclosure. Generally, the gap tensioner 500 includes a linear actuating mechanism operatively coupled between a lower (first) paddle 200A and an upper (second) paddle 200B so that operating of the mechanism changes the vertical spacing between the paddles 200A, 200B.

In the illustrated embodiment, the gap tensioner 500 includes a lower (first) engagement element 502 configured to engage the connector 202 associated with the lower paddle 200A and an upper (second) engagement element 504 configured to engage the connector 222 associated with the upper paddle 200B. In the illustrated embodiment, the lower engagement element 502 is rigidly mounted relative to a gap tensioner housing 506, and the upper engagement element 504 is vertically slidably disposed relative to the housing 506. An actuating shaft 508 is rotatably disposed relative to the housing 506 and is configured to be selectively engaged by a rotational tool, such as a torque wrench (not shown).

A linear actuating mechanism may operatively interpose the actuating shaft 508 and the movable upper engagement element 504. In the illustrated embodiment, the linear actuating mechanism is generally in the form of a rack and pinion mechanism. A pinion 510 (e.g., a circular gear) is mounted for rotation with the actuating shaft 508. A rack 512 (e.g., a linear gear) is mounted for linear movement with the upper engagement element 504 so that the teeth of the rack 512 and the teeth of the pinion 510 are intermeshed. In the illustrated embodiment, rotation of the shaft 508 in a clockwise direction causes the rack 512 and pinion 510 mechanism to move the upper and lower paddles 200A, 200B apart. Rotation of the shaft 508 in a counterclockwise direction causes the rack 512 and pinion 510 mechanism to move the upper and lower paddles 200A, 200B closer together. In alternative embodiments, the arrangement may be reversed, so that the mechanism moves the lower engagement element 502 relative to the housing 506.

In operation, the gap tensioner 500 may be used to apply separating forces to the femur and tibia as described elsewhere herein. In the illustrated embodiment, a torsional force applied to the shaft 508 results in a linear force exerted by the paddles 200A, 200B. One of skill in the art will appreciate that, in the illustrated embodiment, a linear separating force exerted by the paddles 200A, 200B will be directly related to a torsional force applied to the shaft 508. Accordingly, application of a measured or mechanically limited torsional force to the shaft 508 may be used to apply a desired linear separating force to the femur and tibia via the paddles 200A, 200B, such as to provide a desired ligament or other soft tissue tension in connection with an arthroplasty procedure. For example, a torque wrench with a clutch mechanism may be set at a specific torque value associated with a desired gap tension. The torque wrench may be used to apply torsion to the shaft 508, up to the preset torque value. Alternatively, a torque wrench with a torque read-out may be used to apply a desired torque and/or to measure an applied torque, such as may be indicative of ligament tension at a particular gap distance.

Although the gap tensioner 500 has been illustrated and described as comprising a manually operated, rack-and-pinion-type, linear actuating mechanism, it is within the scope of this disclosure to utilize any suitable actuating mechanism. For example, any other mechanical or electromechanical mechanism capable of applying a controlled separating force to the femur and tibia via the paddles 200A, 200B may be utilized in alternative embodiments.

In the illustrated embodiment, the gap tensioner 500 is provided with pin guides 514, 516, which may be generally similar to other pin guides 220 described herein. In the illustrated embodiment, a lower pin guide 514 is rigidly disposed relative to the housing 506 of the gap tensioner 500. Accordingly, the location of one or more openings 518 is fixed with respect to the housing 506. The openings 518 of the lower pin guide 514 may be used to locate pins associated with a tibial cut guide, as described elsewhere herein.

In the illustrated embodiment, an upper pin guide 516 may be movably disposed relative to the housing 506 of the gap tensioner 500. For example, the upper pin guide 516 may be vertically slidably disposed on the housing 506. Accordingly, the vertical location of one or more openings 520 may be adjusted relative to the housing 506. In some embodiments, the upper pin guide 516 may be incrementally adjustable, such as in steps of about 2 mm. In some embodiments, a locking mechanism 522 may be operable to releasably secure the upper pin guide 516 with respect to the housing 506. The openings 520 of the upper pin guide 516 may be used to locate pins associated with a femoral cut guide, as described elsewhere herein.

Figure 13:
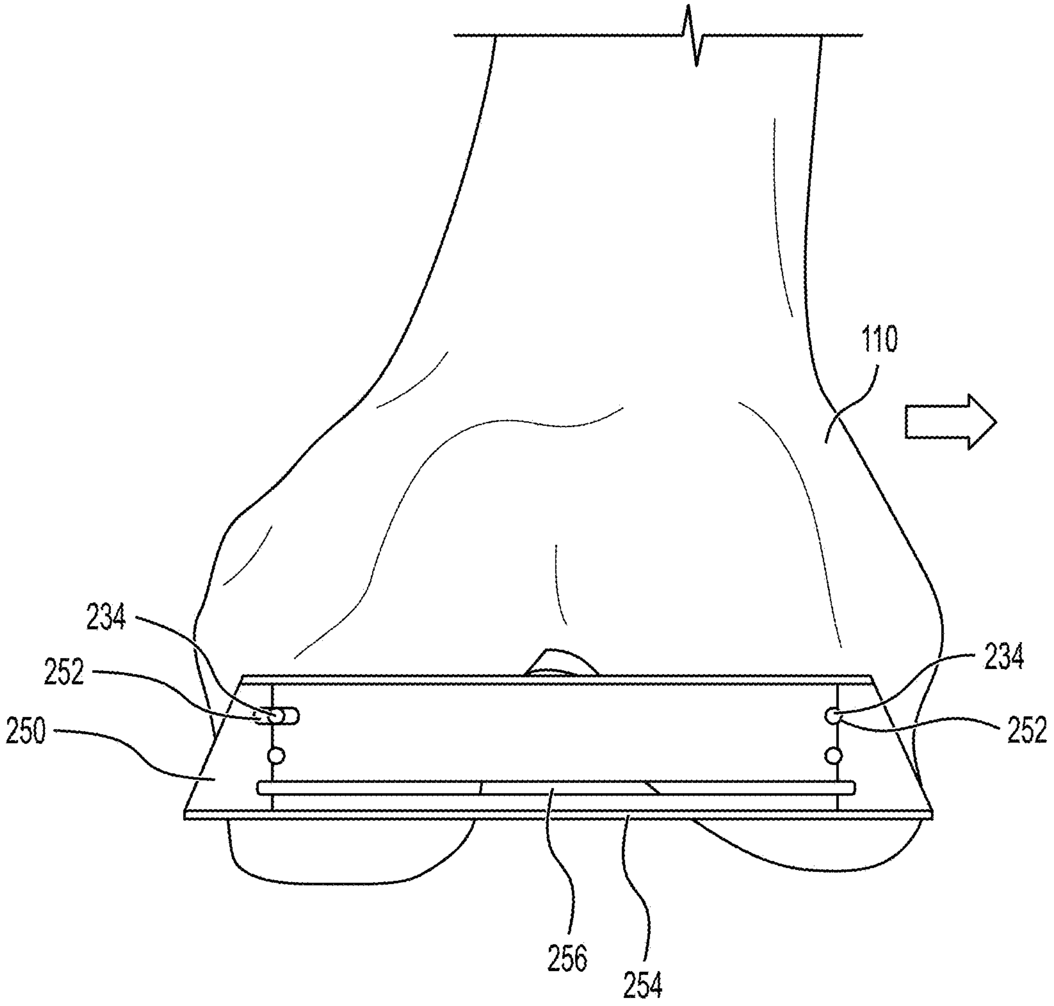
FIG. 13 is an anterior view of the femur with a posterior chamfer cut guide installed.
Figure 14A:
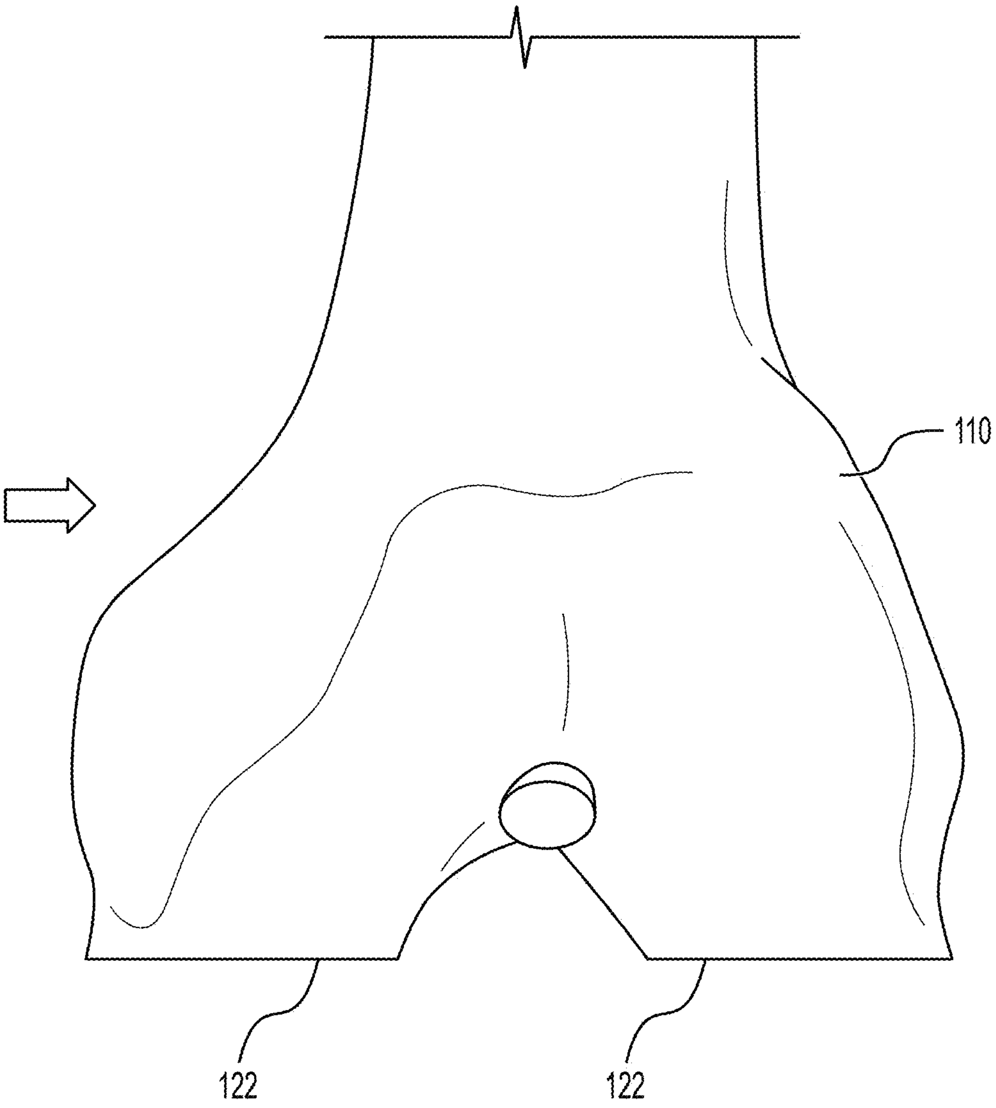
FIG. 14A is an anterior view of the femur showing the posterior chamfer cut.
Figure 14B:
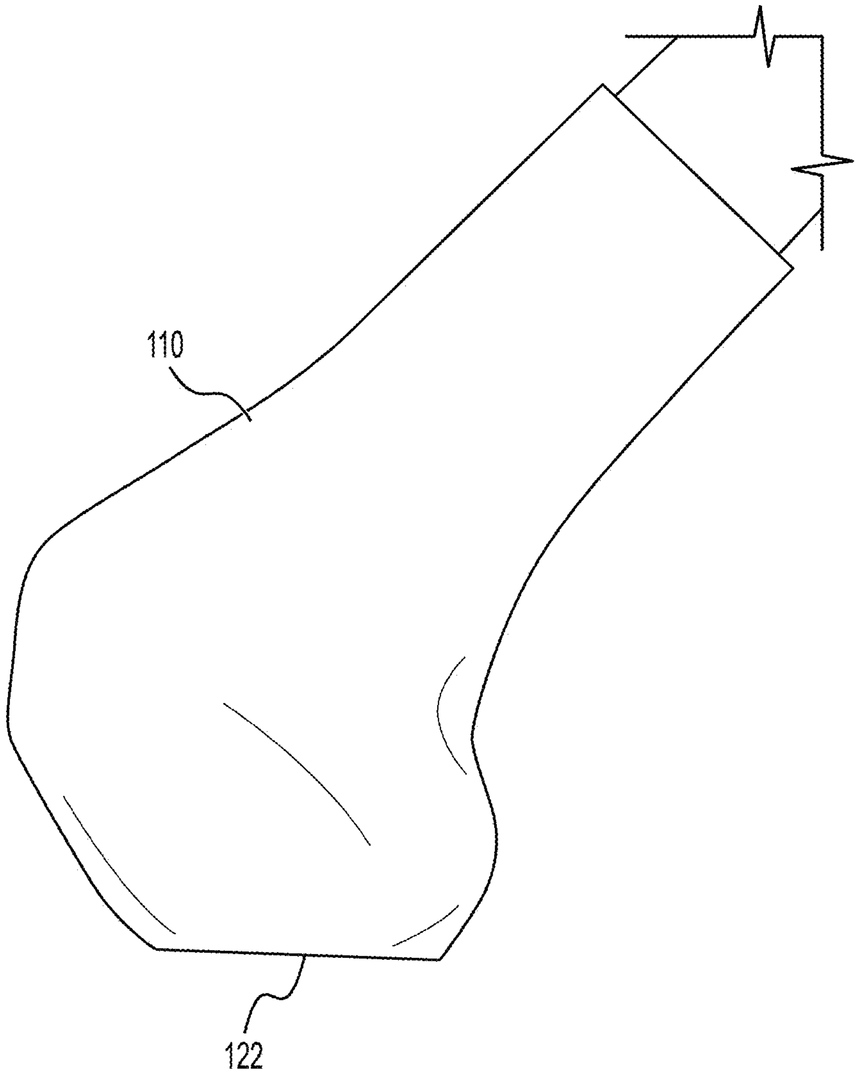
FIG. 14B is a lateral view of the femur showing the posterior chamfer cut.

FIG. 13 is an anterior view of the femur with a posterior chamfer cut guide installed, FIG. 14A is an anterior view of the femur showing the posterior chamfer cut, and FIG. 14B is a lateral view of the femur showing the posterior chamfer cut, all according to at least some aspects of the present disclosure. Referring to FIGS. 13, 14A, and 14B, a posterior chamfer cut guide 250 is mounted to the distal femur 110 using the bone pins 234 for use in performing a resection to create a posterior chamfer cut 122. Specifically, the posterior chamfer cut guide 250 may comprise a pair of through holes 252 that are sized to receive respective bone pins 234. In the illustrated embodiment, one of the through holes 252 is substantially circular to match the shape of the respective bone pin 234, and the other through hole 252 is generally horizontally elongated. As a result, small horizontal variations in locating the bone pins 234 may be accommodated while the desired vertical positioning—and thus location and orientation of the cut plane—of the posterior chamfer cut guide 250 is maintained. The specific shape of the posterior chamfer cut guide 250 is freely assignable so long as the guide includes an appropriate guide surface, such as a flat surface 254 or cutting slit 256 adapted to guide a surgical saw blade (not shown) or burring device to make the posterior chamfer cut. In this exemplary embodiment, the posterior chamfer cut guide 250 includes both a flat bottom surface 254 and a cutting slit 256 that are adapted to guide the surgical saw blade while effectuating the posterior chamfer cut 122. It should be understood, however, that the posterior chamfer cut guide 250 may omit the slit 256 or the flat surface 254. Moreover, it should be understood that the posterior chamfer cut guide 250 may include a plurality of slits 256. In any event, the posterior chamfer cut guide 250 is utilized by a surgeon to guide the surgical saw blade in order to make a planar posterior chamfer cut 122. After the posterior chamfer cut is complete, the posterior chamfer cut guide 250 and bone pins 234 may be removed from the femur 110, resulting in the femur depicted in FIGS. 14A and 14B with the posterior chamfer cut 122 being the first completed bone cut on the femur. In some alternative example procedures, the bone pins 234 may remain in the femur 110 for later use, such as in connection with locating a tibial plateau cut as described below.

The present disclosure contemplates that some conventional TKA procedures may not include referencing of tibial cuts with respect to the femoral cuts or vice versa. That is, in some conventional surgeries, femoral bone cuts and tibial bone cuts are made independently. In contrast, in some example embodiments according to at least some aspects of the present disclosure, knee balancing and bone cuts are made with devices and jigs that are referenced with respect to each other. For example, since the femoral chamfer cut is initially made, then ligament balancing has been determined at mid-flexion or the prescribed angle of flexion, leading to the tibial bone cut may be which is made with respect to the femoral chamfer cut and therefore, the tibial bone cut is made with respect to the chamfer cut and ligaments were properly balanced to ensure a desired relationship of the femur with respect to the tibia. In contrast, some conventional TKA procedures do not spatially link one bone cut to another.

Figure 15:
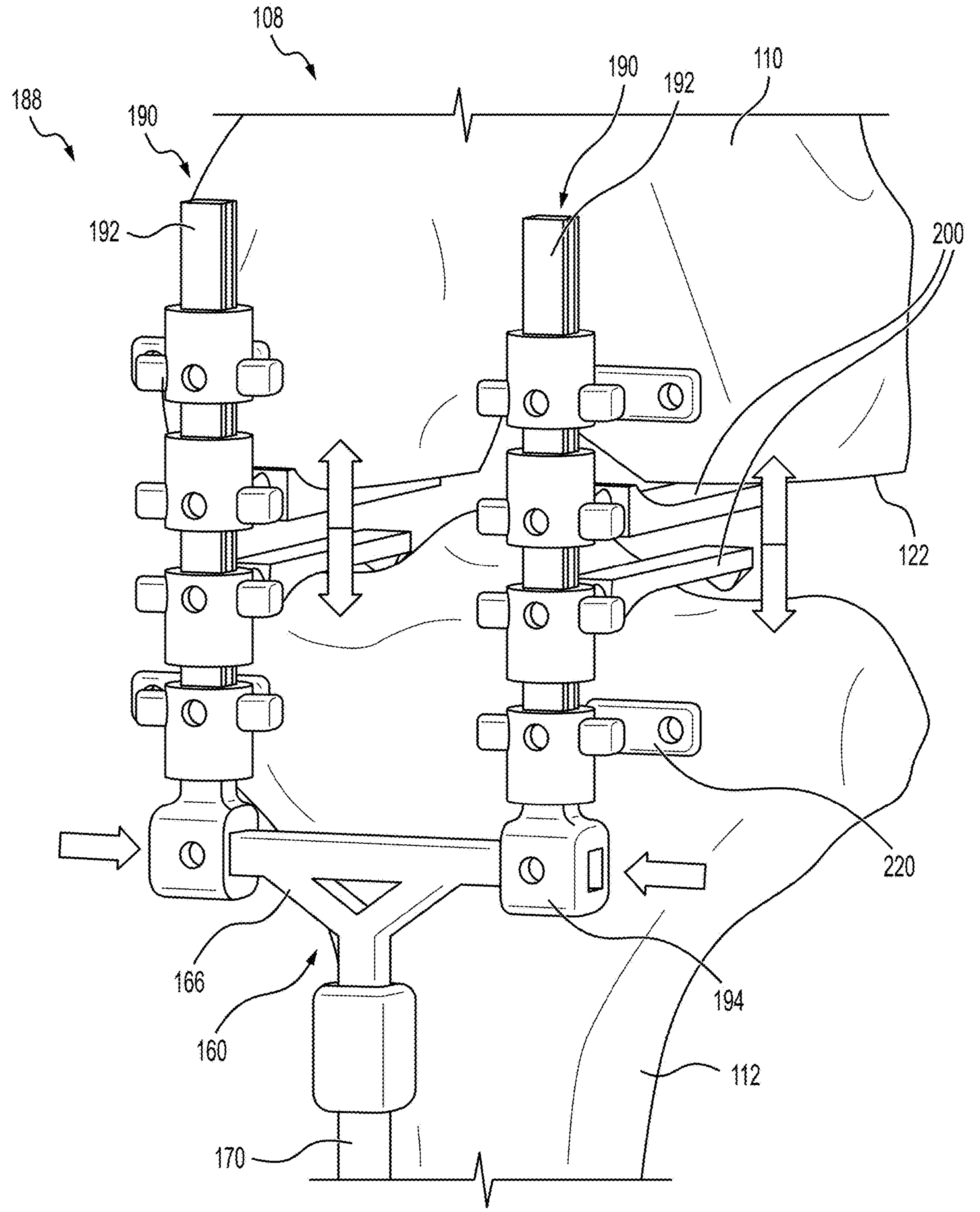
FIG. 15 is a perspective view of the balancing jig in use on the knee after the posterior chamfer cut.

FIG. 15 is a perspective view of the balancing jig in use on the knee after the posterior chamfer cut, according to at least some aspects of the present disclosure. With reference to FIG. 15, the tibial placement guide 160 may be mounted to the tibia 112 after making the posterior chamfer cut 122. The vertical guides 192 may also be mounted to the tibial placement guide 160, specifically mounted to the beam 166. When mounted to the beam 166, each vertical guide 192 may include one or more pin guides 220 and one or more paddles 200. In exemplary form, a pair of paddles 200 may be mounted to each vertical guide 192, as well as a pin guide 220, so that the pin guide is closer to the adapter 194 than are the paddles. In exemplary form, the paddles 200 mounted to each vertical guide 192 are oriented to overlap one another so that the medial vertical guide 192 has its paddles orientated to interpose the femoral medial chamfer cut surface and the medial tibial condyle receiver articular surface. Similarly, the lateral vertical guide 192 has its paddles orientated to interpose the femoral lateral chamfer cut surface and the lateral tibial condyle receiver articular surface.

While the knee joint is bent at approximately 45 degrees or mid-flexion (same angle of the posterior chamfer cut angle) and retained in position (such as by using an external brace, not shown or the intramedullary canal rod mated with respect to the receiver on the tibial jig), the surgeon performs a soft tissue balance for the medial and lateral sides of the knee. As part of this soft tissue balance, the surgeon manipulates the spacing between the overlapping paddles 200 on both the medial and lateral sides until reaching the desired balance. For example, the ligament length and/or tensions and/or condylar separation from the tibial plateau are recorded and set as the goal for balancing at other degrees of flexion, such as full extension and at 90 degrees of flexion. After reaching the balance on the medial and lateral sides, as previously stated the surgeon records the spacing of the paddles on both sides (medial and lateral) using the position of the paddles 200 with respect to the vertical guide 192. In cases where the vertical guide 192 includes markings, these markings may be utilized to record the spacing between the paddles 200 simply by using the position of the connectors 202 with respect to the vertical guides.

After the desired balance is achieved, locations of one or more tibial bone pins 264 are determined. In some example embodiments, a spacer may be used in a manner generally similar to the use of spacer 236, above, except that the spacer may be positioned below and against the respective paddle 200 and the pin guide 220 may be positioned below and against the respective spacer.

Figure 15A:
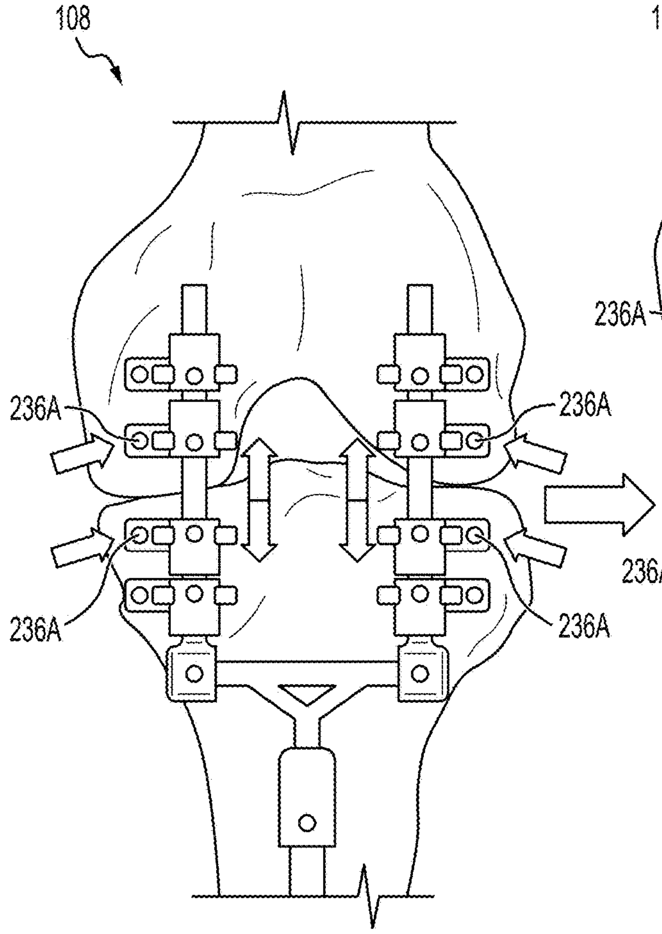
FIG. 15A is a perspective view of an alternative balancing jig in use on the knee after the posterior chamfer cut.
Figure 15B:
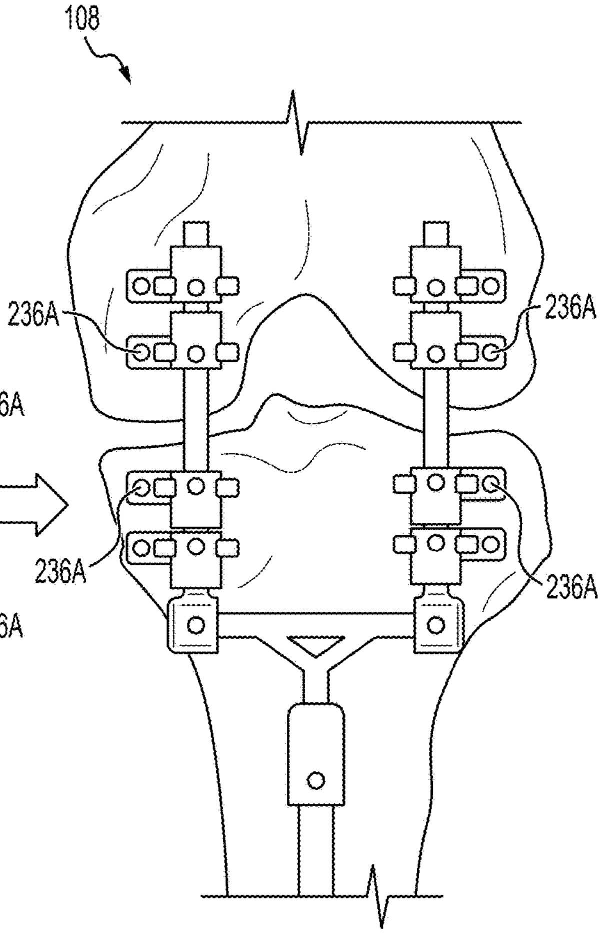
FIG. 15B is a perspective view of the alternative balancing jig of FIG. 15A in use on the knee after the posterior chamfer cut.

FIG. 15A is a perspective view of an alternative balancing jig 188A in use on the knee 108 after the posterior chamfer cut, and FIG. 15B is a perspective view of the alternative balancing jig 188A in use on the knee 108 after the posterior chamfer cut, all according to at least some aspects of the present disclosure. The alternative balancing jig 188A is generally similar in construction and operation to the balancing jig 188 described elsewhere herein, and repeated description is omitted for brevity. The alternative balancing jig 188A may be useful when the gap between the condyle and the tibial plateau is too tight for use of paddles 200, for example. In the illustrated embodiment, balancing pins 236A can be used instead of spacers 236. Once the jig 188A is fixated to the femur and the tibia, the gap between the condyles and the plateau can be created and measured in a manner generally similar to that for jig 188, generating a balanced gap, using the balancing pins 236A.

Figure 16A:
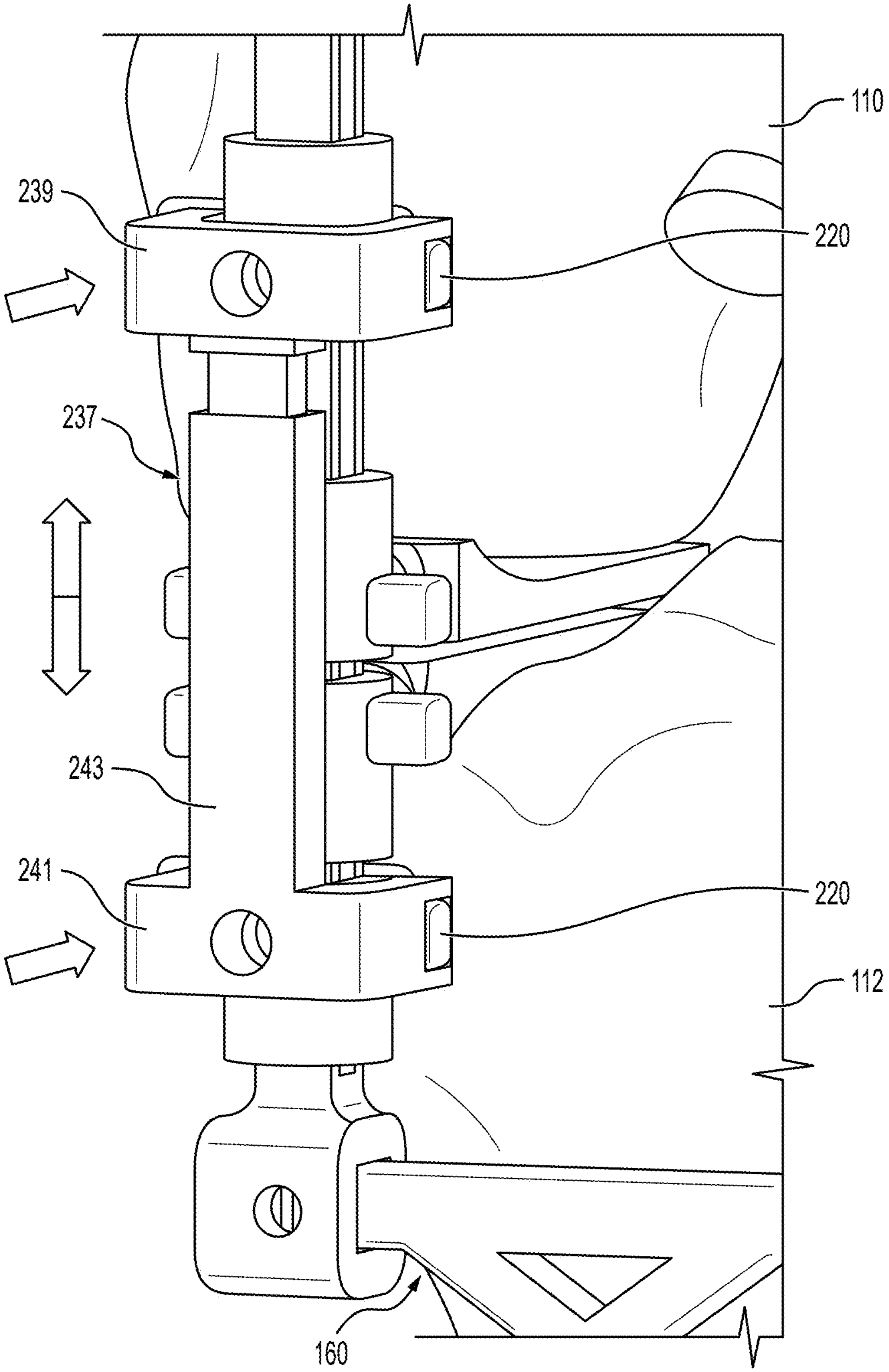
FIG. 16A is a detailed perspective view of an example balancing assembly including a pin-pin spacer for establishing a desired vertical separation between a femoral bone pin and a tibial bone pin.

FIG. 16A is a detailed perspective view of an example balancing assembly including a pin-pin spacer for establishing a desired vertical separation between a femoral bone pin and a tibial bone pin, according to at least some aspects of the present disclosure. Referring to FIG. 16A, in some alternative example embodiments, a pin-pin spacer 237 may be used to establish a desired vertical separation between a femoral bone pin 234 and a tibial bone pin 264. The soft tissue balance has been done by application of the balancing jig 188. That leads to the pin placement for the posterior chamfer cut and the proximal tibial cut. In the illustrated embodiment, the pin-pin spacer 237 includes a femoral component 239, a tibial component 241, and a spacing section 243 interposing the femoral component 239 and the tibial component 241. The femoral component 239 is configured to engage the pin guide 220 for one of the femoral bone pins 234. The tibial component 241 is configured to engage the pin guide 220 for one of the tibial bone pins 264. The spacing section 243 is configured to define the distance between the femoral component 239 and the tibial component 241. In some example embodiments, the spacing section 243 may provide a fixed distance between the femoral component 239 and the tibial component 241. In the illustrated embodiment, the spacing section 243 has an adjustable length so that the distance between the femoral component 239 and the tibial component 241 is adjustable.

Figure 16B:
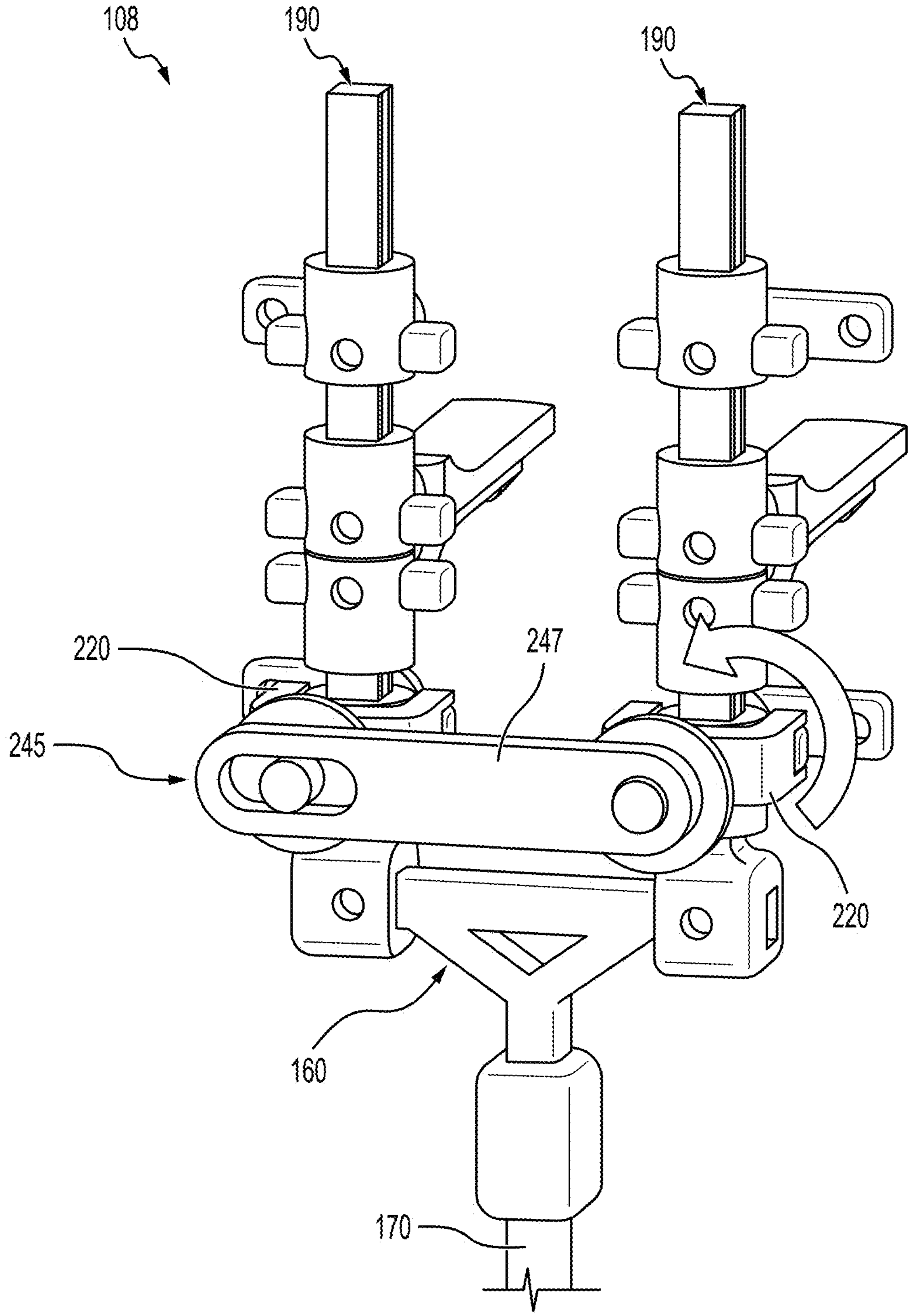
FIG. 16B is a perspective view of the knee balancing jig with a varus-valgus alignment tool installed.

FIG. 16B is a perspective view of the knee balancing jig with a varus-valgus alignment tool installed, according to at least some aspects of the present disclosure. Referring to FIG. 16B, in some alternative example embodiments, a varus-valgus alignment tool 245 may be utilized to determine and/or establish varus-valgus angles for tibial plateau cuts, for example. In the illustrated embodiment, the varus-valgus alignment tool 245 includes a connecting bar 247 pivotably coupled to one tibial pin guide 220 and pivotably and slidably coupled to the other tibial pin guide 220. By determining the angle of the connecting bar 247 relative to the other components of the balancing jig 188, the varus-valgus angle may be measured. Similarly, if it is desired to establish a particular varus-valgus angle, the connecting bar 247 may be positioned relative to the other components of the balancing jig 188 at the desired angle.

In some embodiments, the balancing jig 188 may act as one or both of a ligament balancing device, allowing a force to be imposed upon two paddles that rest respectively against the medial distal femur (superior medial paddle) and medial proximal tibia (inferior medial paddle), and a force to be imposed upon two paddles that rest respectively against the lateral distal femur (superior lateral paddle) and lateral proximal tibia (inferior lateral paddle); and/or a bony resection guide, based upon accepted principles of TKA. A TKA when viewed from a lateral perspective may be described as a composite thickness of three heights, comprising the metallic height of the femoral component, an anticipated height of the polyethylene insert, and a metallic height of the tibial component. Using the balancing jig 188, that composite height can be applied to the distal femur and proximal tibia in many locations. For adherence to accepted TKA technique, the medial distal paddle's accompanying pin may generally sit about 2-4 millimeters below the surface of the native medial tibia. The lateral medial paddle's accompanying pin may generally sit about 8-10 millimeters below the surface of the native lateral tibia. These pins may then represent a 6 degrees of freedom tibial cut plane that may be referenced off of the posterior chamfer cut plane and may be geometrically related to the posterior chamfer cut. This geometric relationship may become rectangular, such as if 45 degrees is added to the tibial cut.

Figure 17:
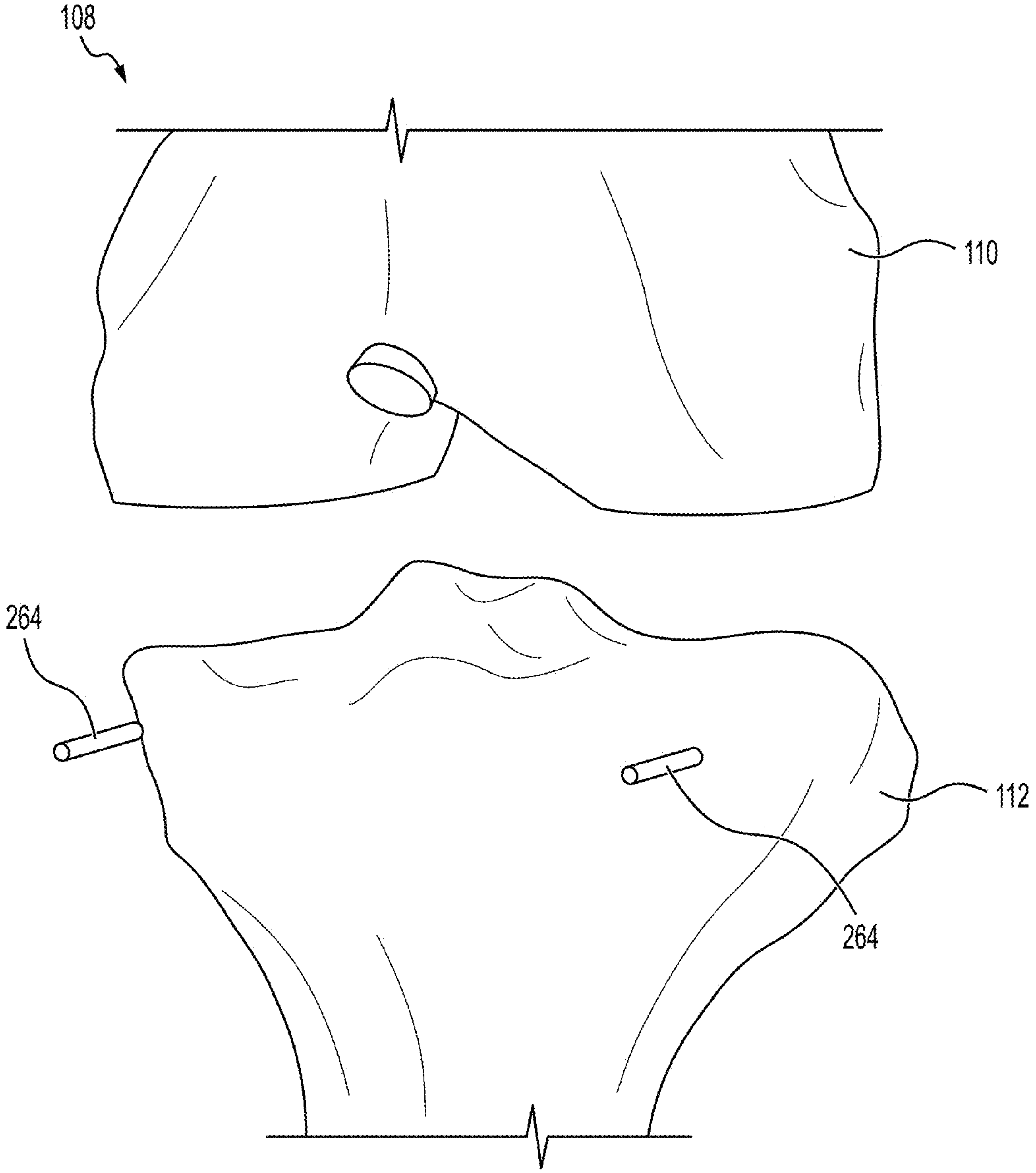
FIG. 17 is a perspective view of the knee with tibial bone pins installed.

FIG. 17 is a perspective view of the knee with tibial bone pins installed, according to at least some aspects of the present disclosure. Referring to FIGS. 15 and 17, similar to the procedure described above for the femur, after the position of each pin guide 220 for the tibial bone pins 264 is finalized, a bone drill bit (not shown) is inserted through the opening 232 so that the walls of the flange 230 delineating the opening act as a guide for the drill bit. Two holes are drilled into the proximal tibia 112 that are aligned with the respective openings 232. Thereafter, a pair of bone pins 264 are inserted through the respective openings 232 of the pin guide 220 and secured within the drilled tibial cavities. Post bone pin 264 placement, the remining components may be removed (pin guide 220, paddles 200, vertical guides 192, tibial placement guide 160), resulting in the configuration depicted in FIG. 17.

Figure 18:
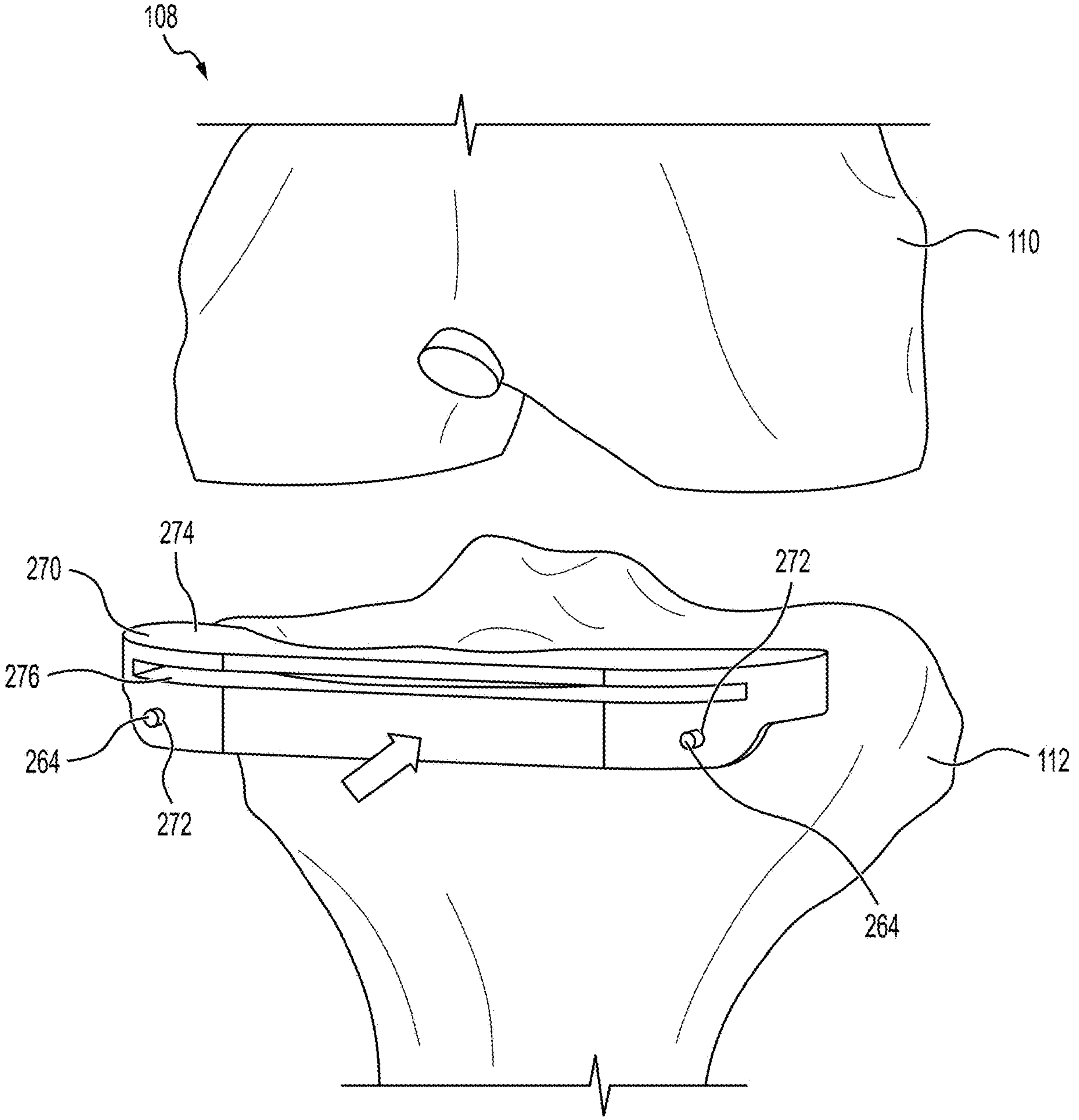
FIG. 18 is a perspective view of the knee with an example tibial cutting guide installed.
Figure 19:
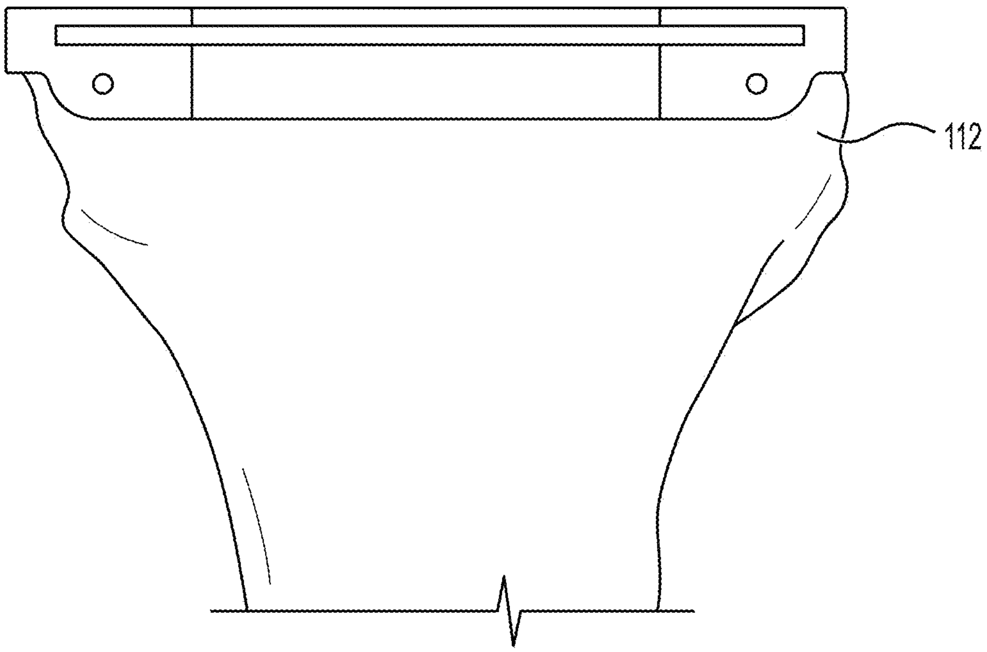
FIG. 19 is an anterior view of the tibia showing the tibial plateau cut.
Figure 20:
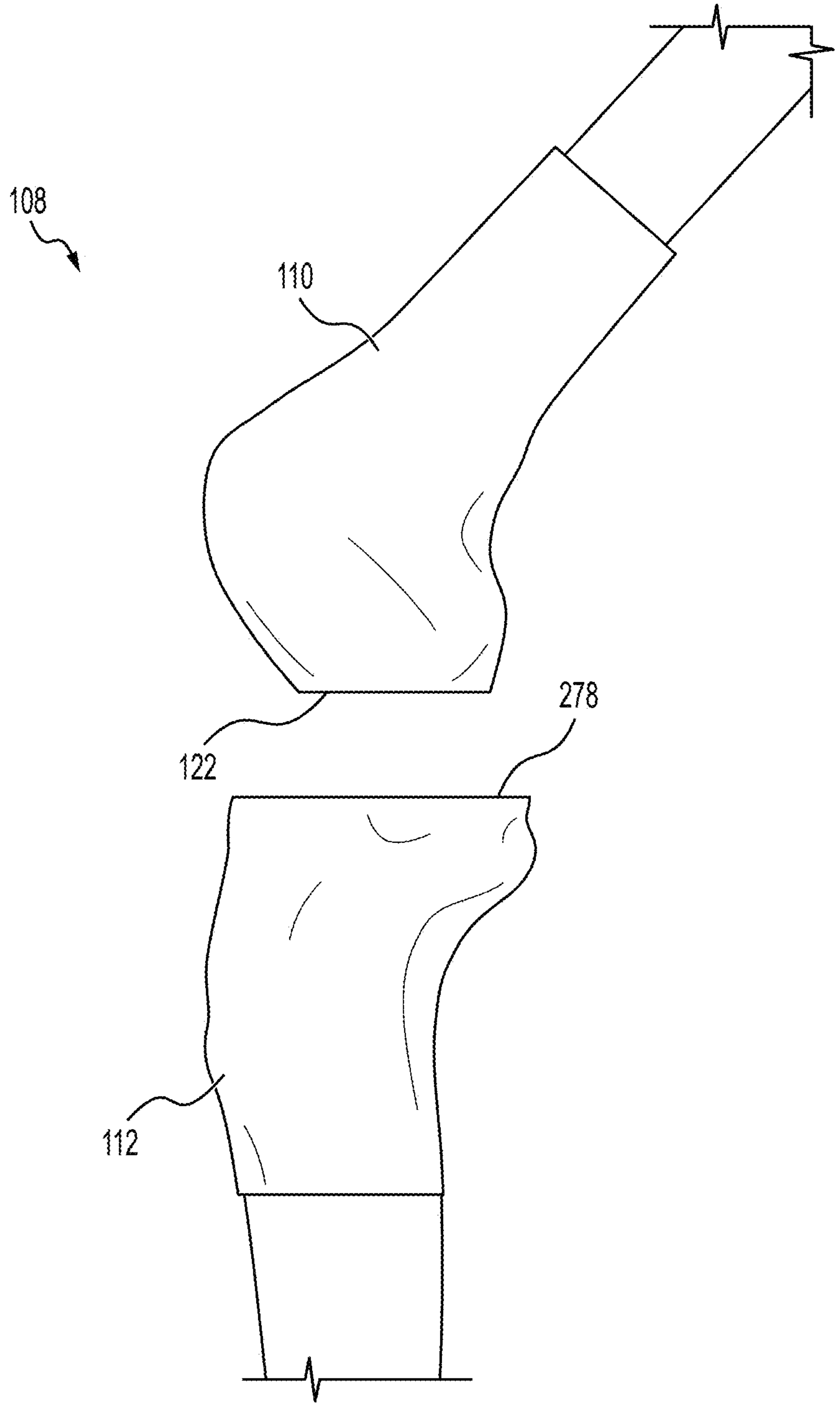
FIG. 20 is a lateral view of the knee showing the tibial plateau cut and the posterior chamfer cut.

FIG. 18 is a perspective view of the knee with an example tibial cutting guide installed, FIG. 19 is an anterior view of the tibia showing the tibial plateau cut, and FIG. 20 is a lateral view of the knee showing the tibial plateau cut and the posterior chamfer cut, all according to at least some aspects of the present disclosure. Turning to FIGS. 18-20, a tibial cutting guide 270 is mounted to the proximal tibia using the bone pins 264. Specifically, the tibial cutting guide 270 may comprise a pair of through holes 272 that are sized to receive respective bone pins 264. The specific shape of the tibial cutting guide 270 is freely assignable so long as the guide includes an appropriate guide surface, such as a flat surface 274 or cutting slit 276 adapted to guide a surgical saw blade or burring device (not shown) to make the tibial plateau cut. In this exemplary embodiment, the tibial cutting guide 270 includes both a flat top surface 274 and a cutting slit 276 that are adapted to guide the surgical saw blade while effectuating the tibial plateau cut 278. It should be understood, however, that the tibial cutting guide 270 may omit the slit 276 or the flat surface 274. Moreover, it should be understood that the tibial cutting guide 270 may include a plurality of slits 276. In any event, the tibial cutting guide 270 is utilized by a surgeon to guide the surgical saw blade in order to make a planar tibial plateau cut 278. After the tibial plateau cut 278 is complete, the tibial cutting guide 270 and the remaining bone pins 234, 264 may be removed, resulting in the tibia depicted in FIG. 20 with the tibial plateau cut being the first completed bone cut on the tibia and the second completed bone cut for the overall procedure.

In some alternative procedures, the tibial plateau cut 278 may be performed before the femoral posterior chamfer cut 122, using generally similar operations to those described above. For example, the location of the tibial plateau cut 278 may be determined first, and the tibial bone pins 264 may be placed. The tibial cutting guide 270 may be installed, and the tibial plateau cut 278 may be made. Then, the balancing jig 188 may be used to balance the knee 108 relative to the tibial plateau cut 278 and the locations of the femoral bone pins 234 may be established. The posterior chamfer cut guide 250 may be installed, and the posterior chamfer cut 122 may be made.

Figure 21:
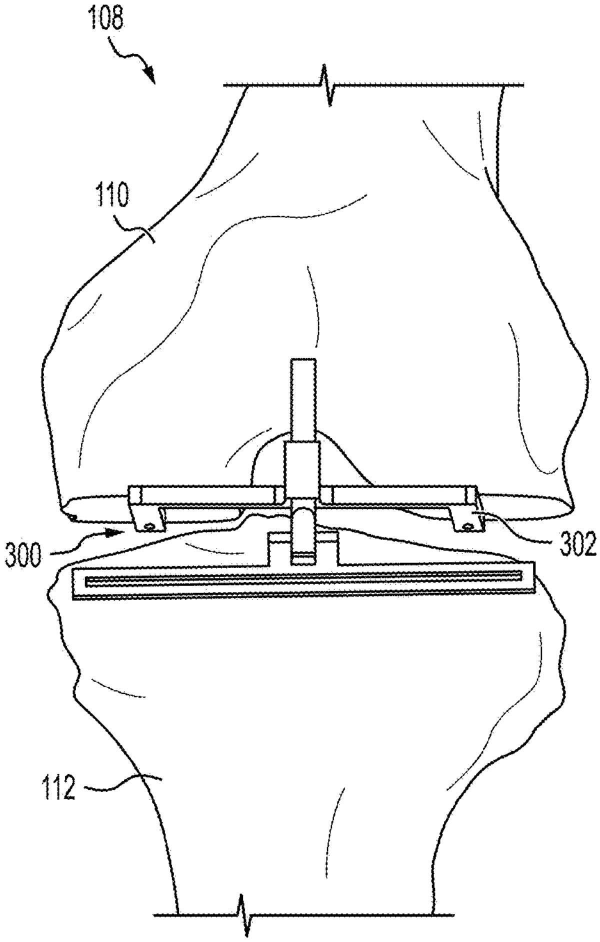
FIG. 21 is an anterior view of an alternative example tibial plateau cut guide.
Figure 22:
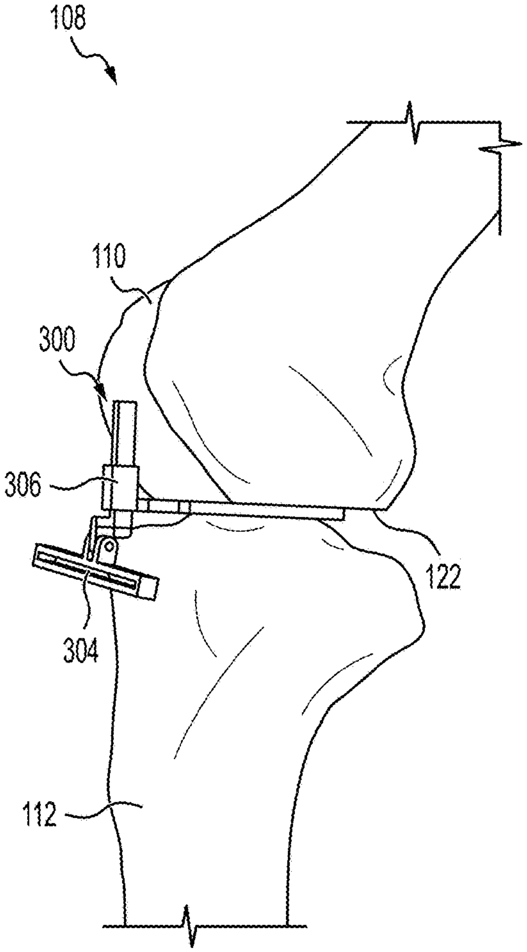
FIG. 22 is a lateral view of the alternative example tibial plateau cut guide.

FIG. 21 is an anterior view of an alternative example tibial plateau cut guide, and FIG. 22 is a lateral view of the alternative example tibial plateau cut guide, all according to at least some aspects of the present disclosure. Referencing FIGS. 21 and 22, an alternate exemplary tibial plateau cut guide 300 may be utilized to effectuate the tibial plateau cut 278. The plateau cut guide 300 can be adjusted before installation or after installation and may serve to rigidly connect the femur 110 to the desired tibial cut.

By way of example, after the posterior chamfer cut 122 is complete, and the posterior chamfer cut guide 250 and bone pins 234 are removed from the femur 110. The cut guide 300 is mounted to the femoral posterior chamfer cut 122 by means of the chamfer cut reference mounting plate 302. The tibial cut guide slot 304 can be translated superiorly or inferiorly through the extension mechanism 306, which may allow the vertical distance between the posterior chamfer cut 122 and the tibial plateau cut 278 to be adjusted. Additionally, pivot coupling mechanisms integrated into the extension mechanism 306 can be used to adjust the varus/valgus or slope angle of the tibial cut, per the discretion of the surgeon. Necessary distance and angle readouts can be viewed on the extension mechanism 306, and once the desired tibial position is determined, the system is locked in place and the tibial plateau cut 278 is made through tibial cut guide slot 304.

Figure 23:
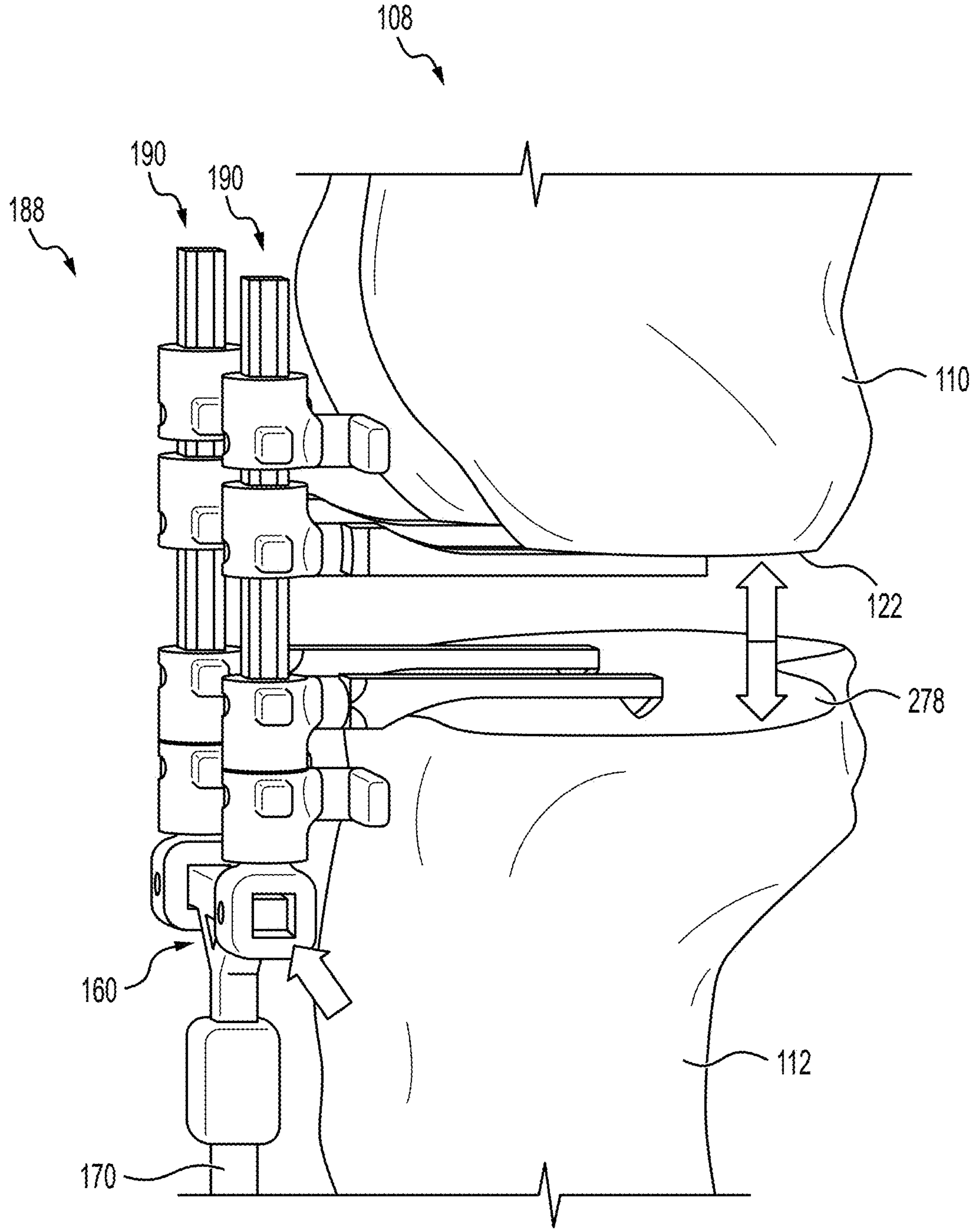
FIG. 23 is a perspective view of the knee balancing jig in use on the knee after the tibial plateau cut.

FIG. 23 is a perspective view of the knee balancing jig in use on the knee after the tibial plateau cut, according to at least some aspects of the present disclosure. Turning to FIGS. 10A-10C and 23, after the posterior chamfer cut 122 and the tibial plateau cut 278 are completed, the tibial placement guide 160 may be mounted to the tibia 112. The vertical guides 192 of the balancing assemblies 190 may also be mounted to the tibial placement guide 160, specifically mounted to the beam 166. When mounted to the beam 166, each vertical guide 192 may include one or more pin guides 220. In exemplary form, a pair of paddles 200 may be mounted to each vertical guide 192 and oriented to overlap one another so that the medial vertical guide 192 has its paddles orientated to interpose the femoral medial chamfer cut surface 122 and the tibial plateau cut surface 278. Similarly, the lateral vertical guide 192 has its paddles orientated to interpose the femoral lateral chamfer cut surface 122 and the tibial plateau cut surface 278. The jig is configured for cut distance measurement. Specifically, the distance between the posterior chamfer cut 122 and the tibial slope cut 278 (D_PCC_TSC) is measured.

Figure 24:
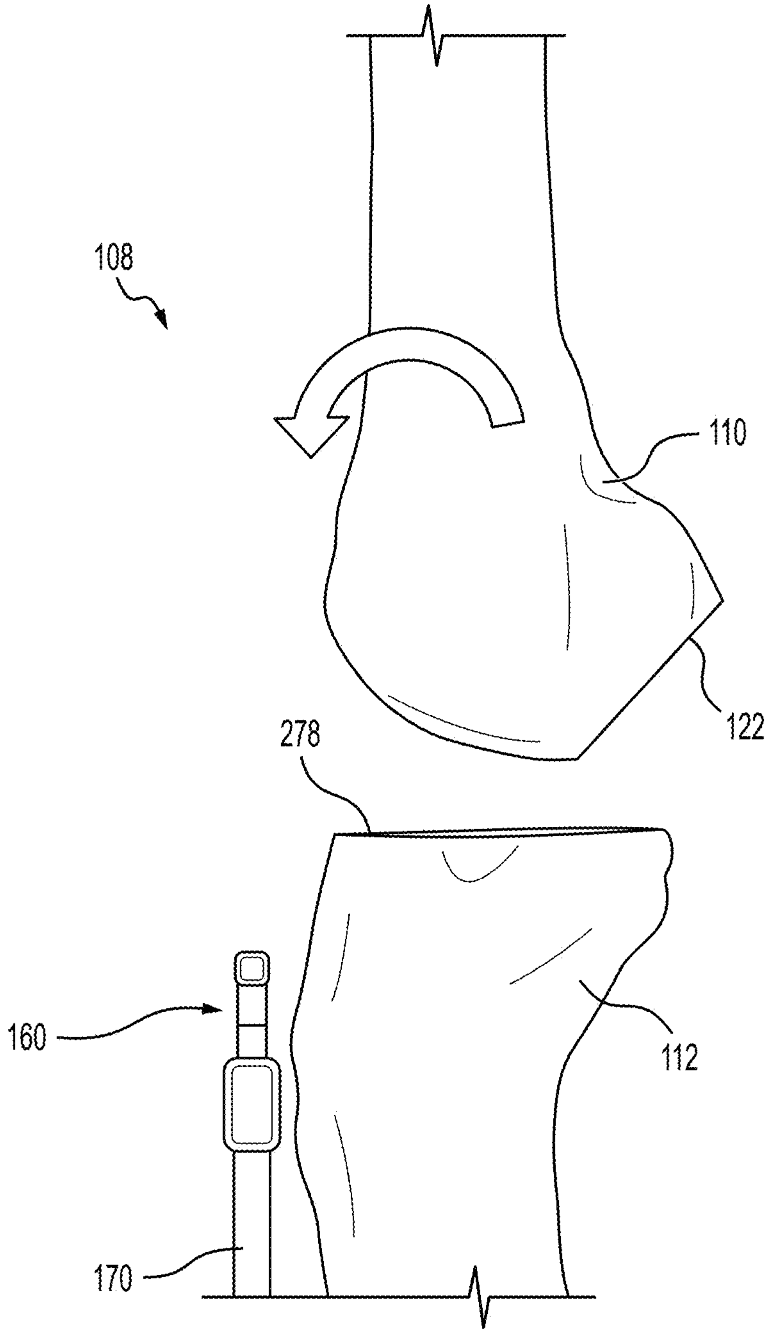
FIG. 24 is a lateral view of knee rotated to a full extension position.

FIG. 24 is a lateral view of knee rotated to a full extension position, according to at least some aspects of the present disclosure. Referring to FIG. 24, the surgeon may rotate the tibia 112 with respect to the femur 110 to reach a full extension position. While the knee joint 108 is retained in full extension (such as by using an external brace, not shown), the surgeon performs a soft tissue balance for the medial and lateral sides of the knee, balancing the knee again with the information gained for mid-flexion balancing and making of the femoral chamfer cut. The same distance and soft-tissue tensions derived for the chamfer cut with respect to the tibial cut may be maintained for the femoral extension cut.

Figure 25:
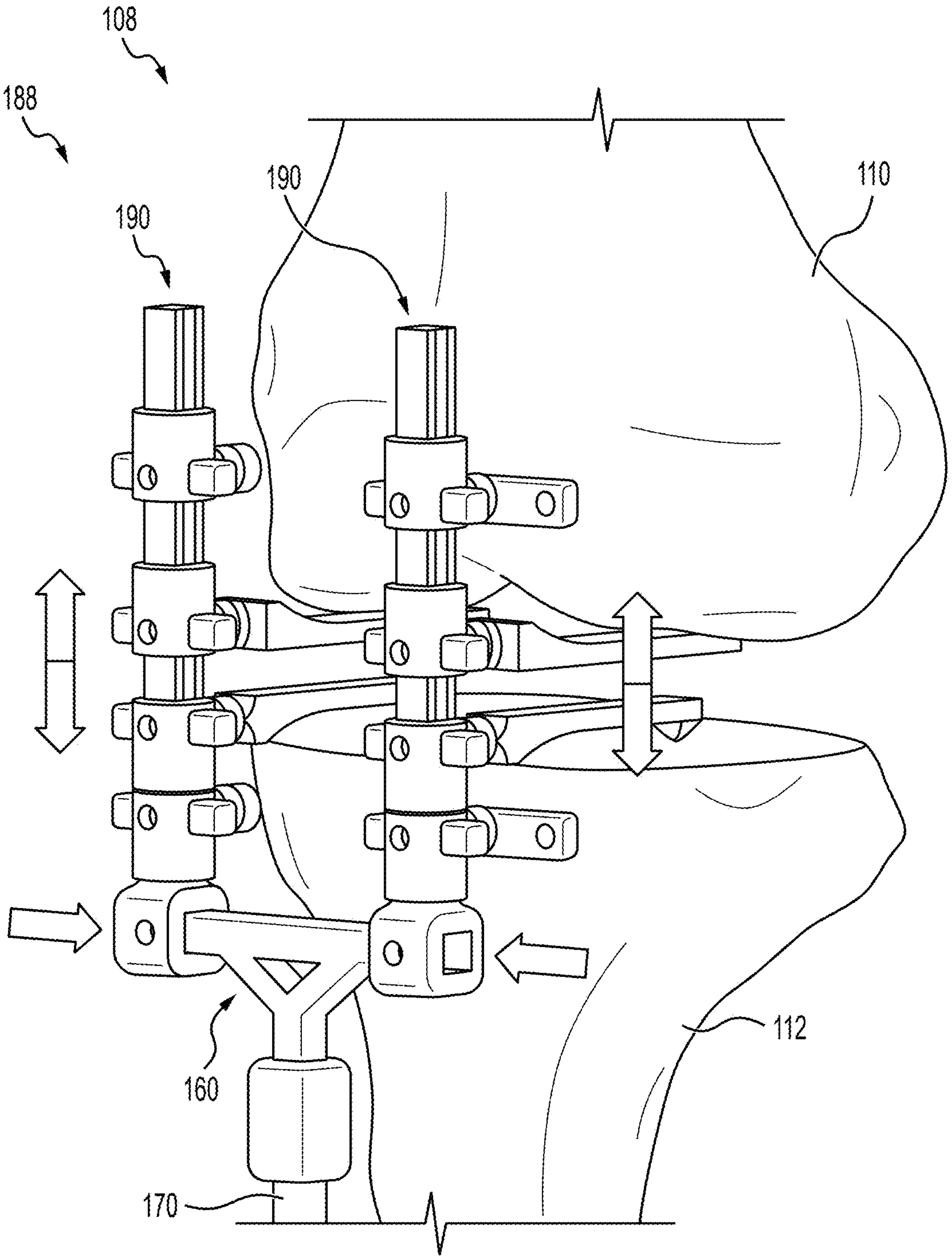
FIG. 25 is a perspective view of the knee balancing jig in use on the knee in preparation for the femoral extension cut.

FIG. 25 is a perspective view of the knee balancing jig in use on the knee in preparation for the femoral extension cut, according to at least some aspects of the present disclosure. Referring to FIGS. 10A-10C and 25, as part of this soft tissue balance, the surgeon manipulates the spacing between the overlapping paddles 200 of the balancing assemblies 190 on both the medial and lateral sides until reaching the desired balance. The determined distance (width) between the posterior chamfer cut and the proximal tibial resection is maintained by imposing the same distance, now based on the proximal tibial resection, to the distal femur and defining the distal femoral cut plane. After reaching the balance on the medial and lateral sides, the surgeon records the spacing of the paddles on both sides (medial and lateral) using the position of the paddles 200 with respect to the vertical guide 192. In cases where the vertical guide 192 includes markings, these markings may be utilized to record the spacing between the paddles 200 simply by using the position of the connectors 202 with respect to the vertical guides.

Post soft tissue balancing at full extension, positions of pin guides 220 mounted to the vertical guides 192 are determined in a manner similar to that described above, and the pin guides 220 are secured in position. After the position of each pin guide 220 is finalized, a bone drill bit (not shown) is inserted through the opening 232 of the pin guide so that the walls of the flange 230 delineating the opening act as a guide for the drill bit. Two holes are drilled into the distal femur that are aligned with the respective openings 232.

Figure 26:
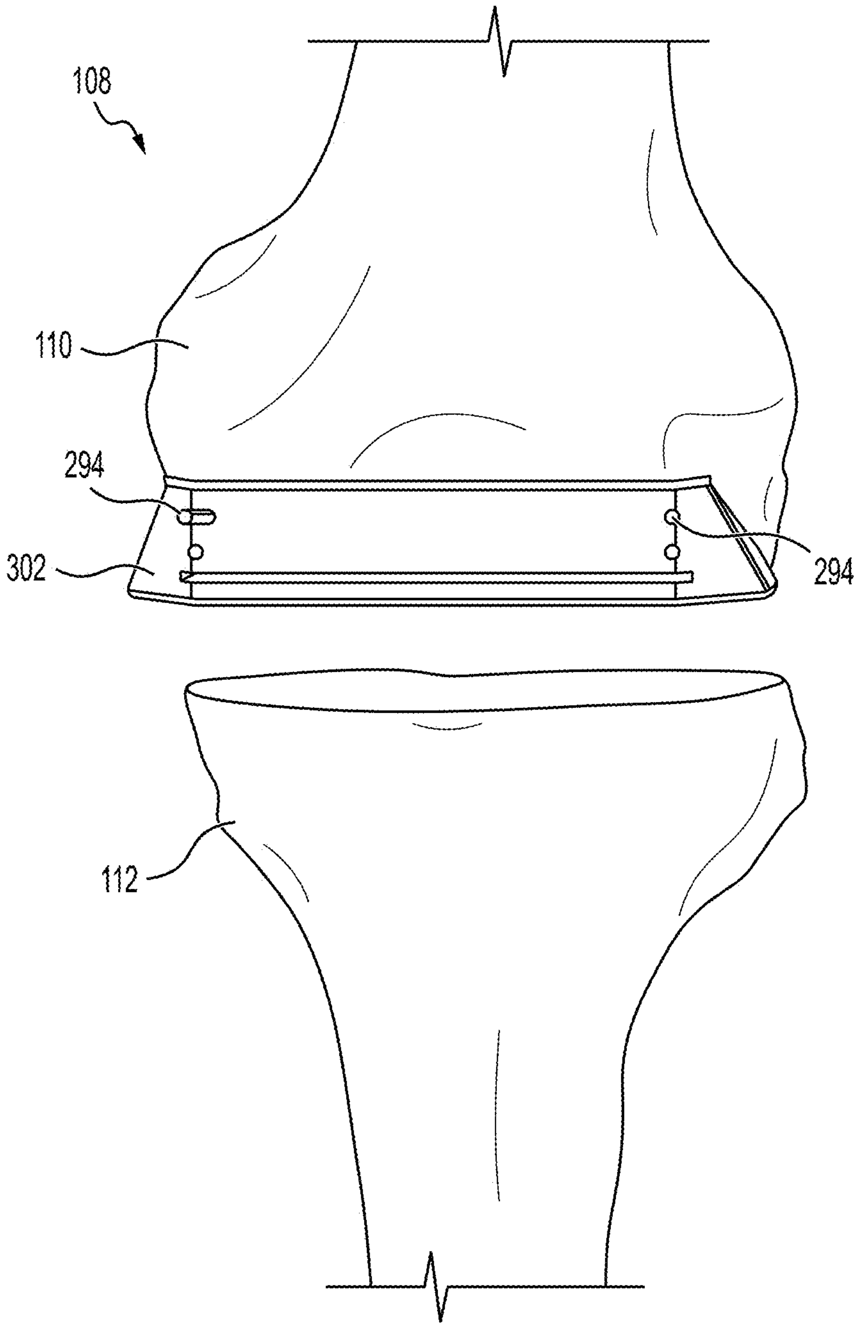
FIG. 26 is an anterior view of the knee with an example femoral extension cut guide installed.

FIG. 26 is an anterior view of the knee with an example femoral extension cut guide installed, according to at least some aspects of the present disclosure. Referring to FIGS. 25 and 26, a pair of bone pins 294 are inserted through the respective openings 232 of the pin guide 220 and secured within the drilled femoral cavities. Post bone pin 294 placement, the remining components may be removed (pin guides 220, paddles 200, vertical guides 192, tibial placement guide 160). Referring to FIG. 26, a femoral extension cut guide 302 is installed on the bone pins 294 in a manner similar to that described above.

Figure 27:
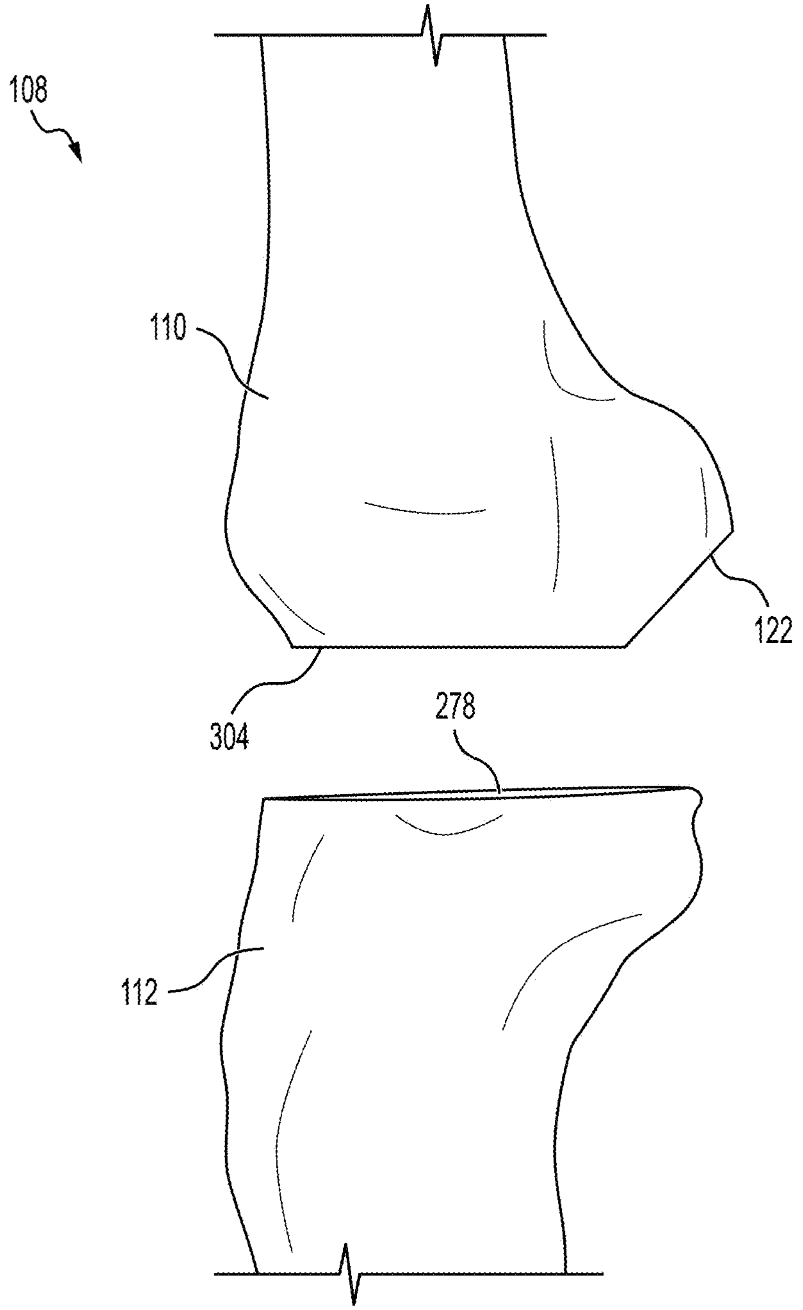
FIG. 27 is a lateral view of the knee showing the femoral extension cut, tibial plateau cut, and posterior chamfer cut.

FIG. 27 is a lateral view of the knee showing the femoral extension cut, tibial plateau cut, and posterior chamfer cut, according to at least some aspects of the present disclosure. The femoral extension cut 304 is made, resulting in the bone configuration shown in FIG. 27. As shown in the lateral view, the distal femoral cut 304 and the proximal tibial cut 278 may be substantially parallel and of known separation, which may result from use of the balancing jig 188 as described. In similar fashion, the posterior chamfer cut 122 and proximal tibial cut 278 have a substantially similar relationship. At this time, the surgeon performs femoral component sizing, which can be performed with anterior referencing or posterior referencing or a combination of both.

Figure 28:
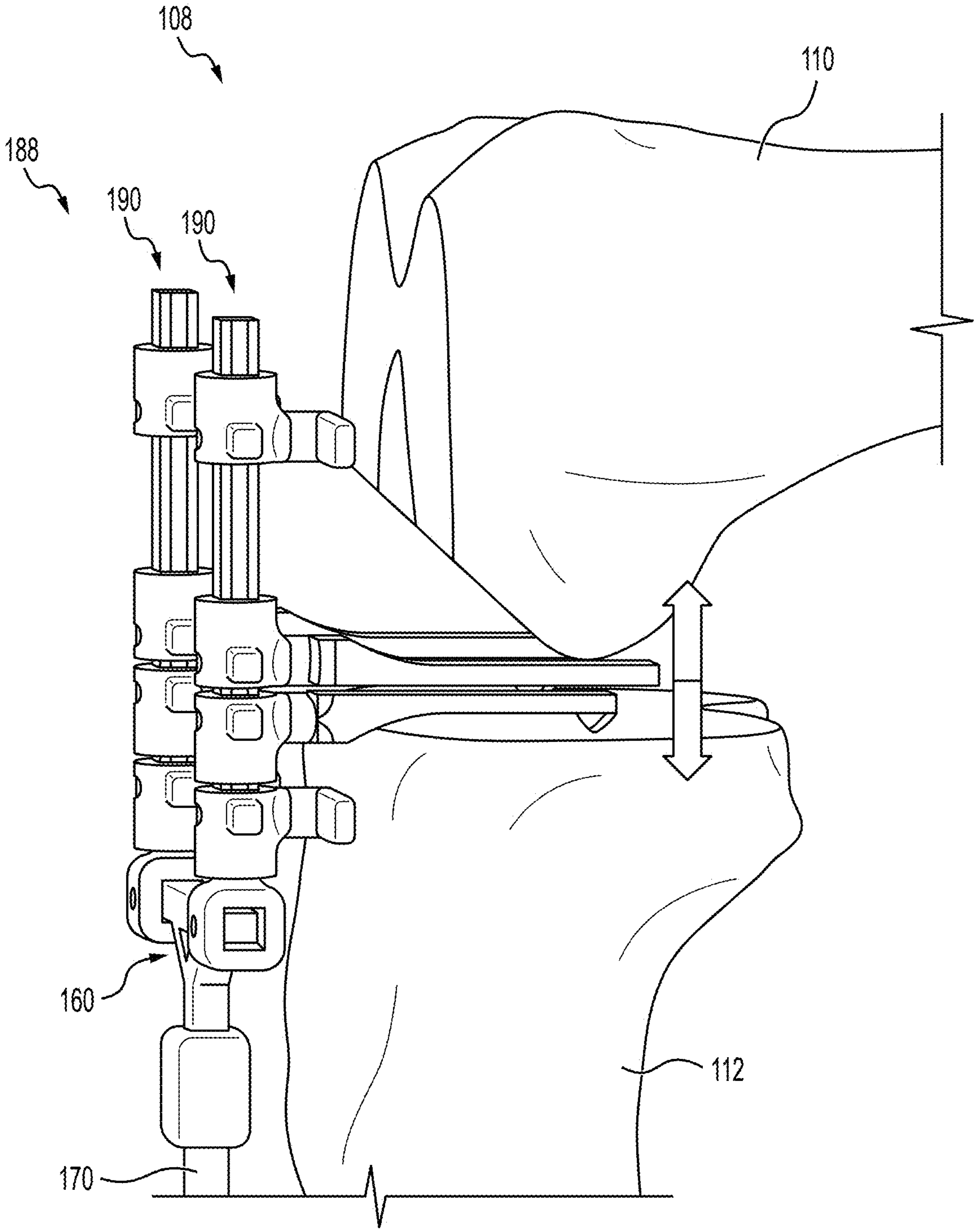
FIG. 28 is a perspective view of the knee balancing jig in use on the knee for posterior referencing.

FIG. 28 is a perspective view of the knee balancing jig in use on the knee for posterior referencing, according to at least some aspects of the present disclosure. Referring to FIG. 28, if posterior referencing is the choice, the knee is positioned at about 90 degrees of knee flexion, for example. Then, the knee is balanced as desired, such as by using the values derived between the chamfer cut and tibial cut and maintained for the femoral extension cut and tibial cut. Therefore, the same ligament lengths and tension and femoral tibial gaps may be maintained throughout the range of knee flexion. The femoral flexion cut location is determined, and the cut is made using a femoral cut guide mounted to bone pins in a manner similar to that described above.

Figure 29:
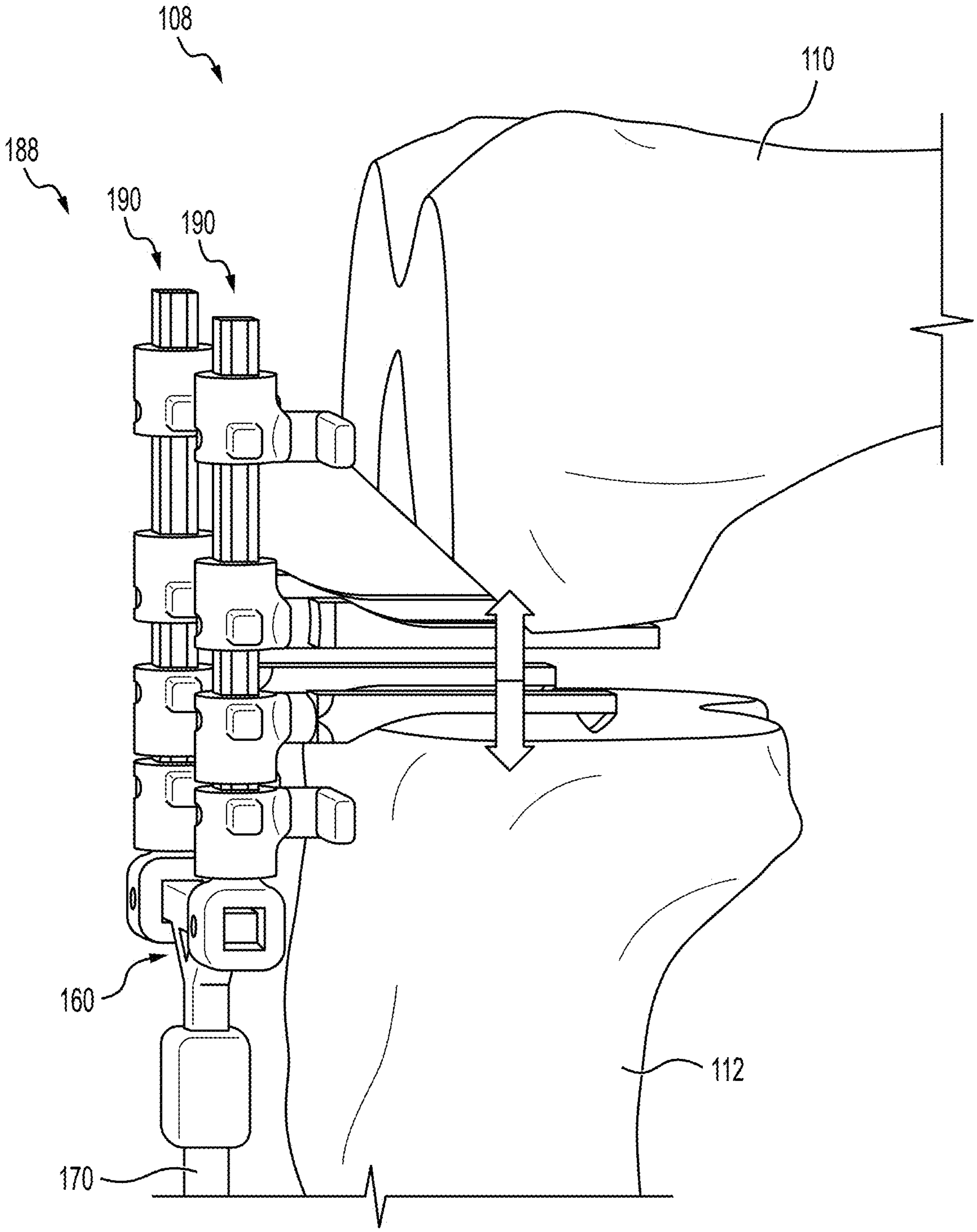
FIG. 29 is a perspective view of the knee balancing jig in use on the knee after the femoral flexion cut.

FIG. 29 is a perspective view of the knee balancing jig in use on the knee after the femoral flexion cut, according to at least some aspects of the present disclosure. Referring to FIG. 29, if desired, the balance of the knee can be confirmed using the balancing jig 188 in a manner similar to that described above. The femoral component is now sized and proper balancing is derived and maintained.

Figure 30:
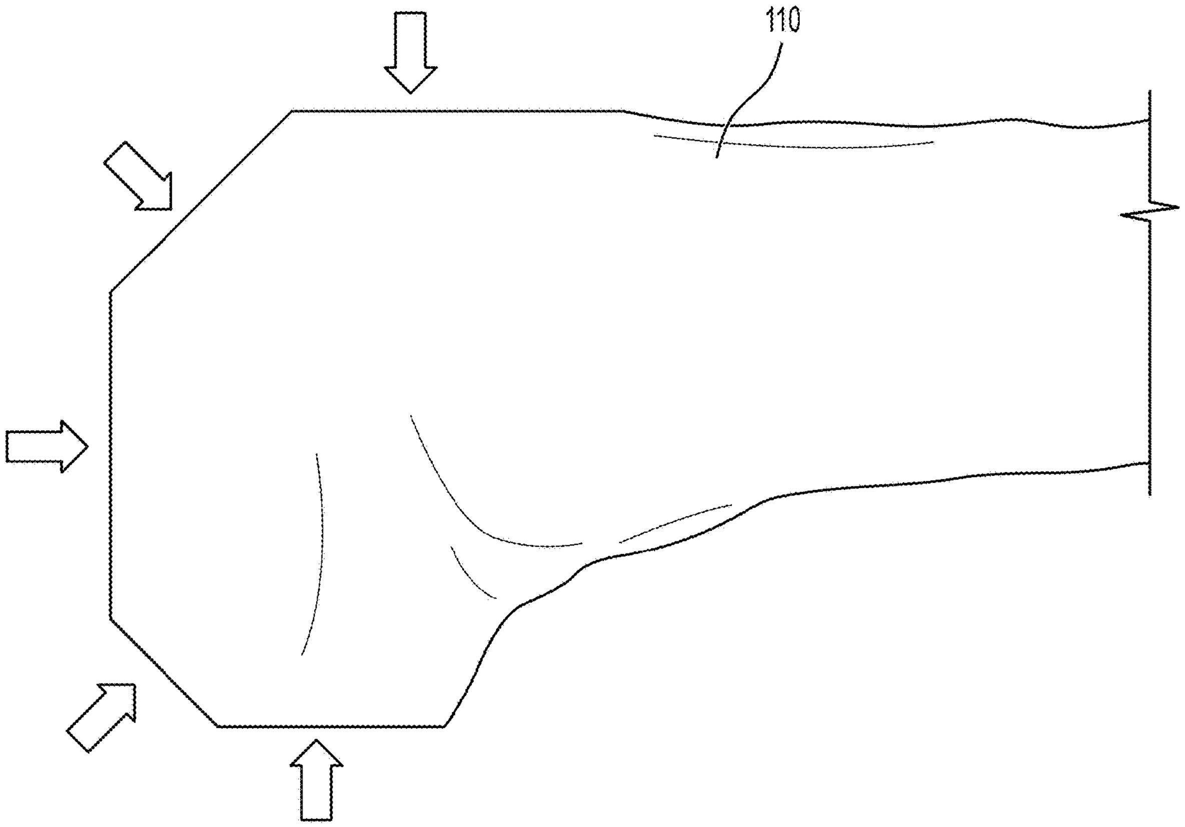
FIG. 30 is a lateral view of a distal femur showing various cuts in preparation for mounting of a femoral implant.

FIG. 30 is a lateral view of a distal femur showing various cuts in preparation for mounting of a femoral implant, according to at least some aspects of the present disclosure. Referring to FIG. 30, the remaining anterior and anterior chamfer cuts may be made, such as to fit a required implant size and/or configuration. In some example embodiments, the chosen manufacturer's femoral sizing guide may be positioned against the posterior femoral cut and posterior chamber cut and the size of the femoral component that will not result in notching of the distal femur may be selected. The manufacturer's cut guide may be positioned to be planar to the posterior femoral and distal femoral resections, and the anterior and anterior chamfer cuts may be made.

Figure 31A:
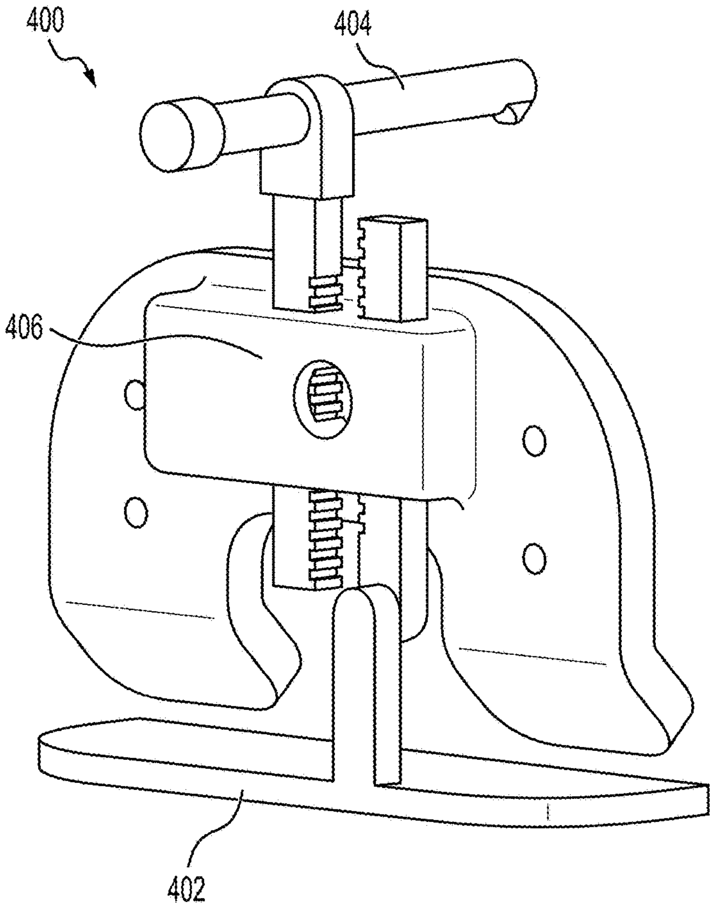
FIG. 31A is a perspective view of an example anterior reference guide.
Figure 31B:
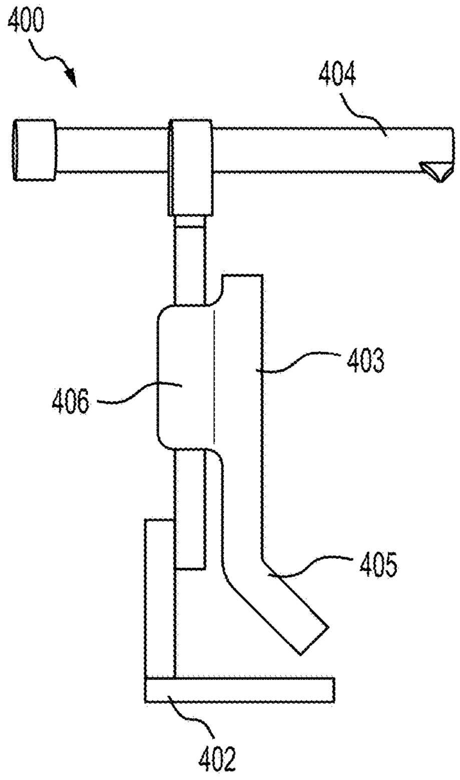
FIG. 31B is a lateral view of the anterior reference guide.
Figure 32:
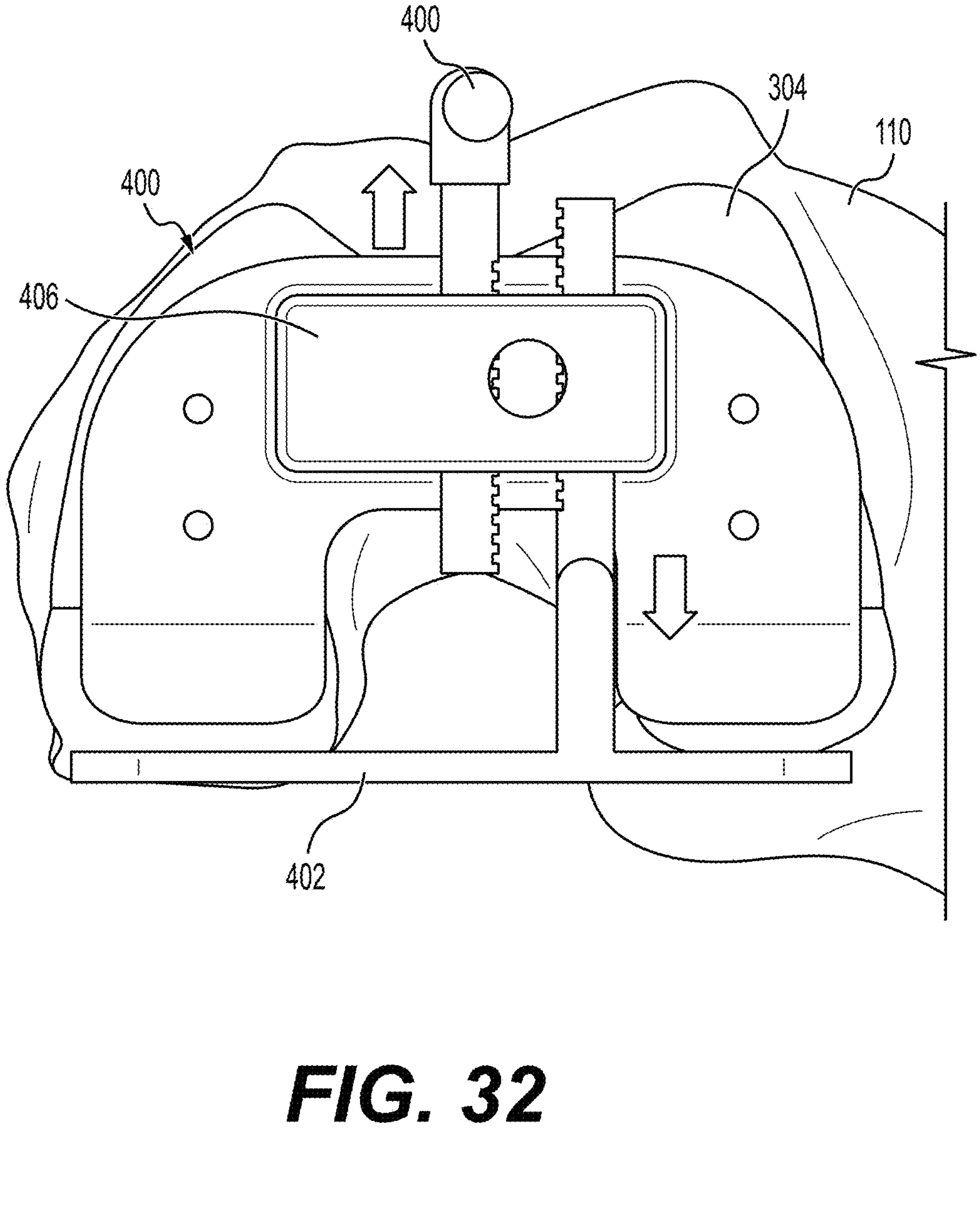
FIG. 32 is a distal view of the anterior reference guide in use on the femur.
Figure 33:
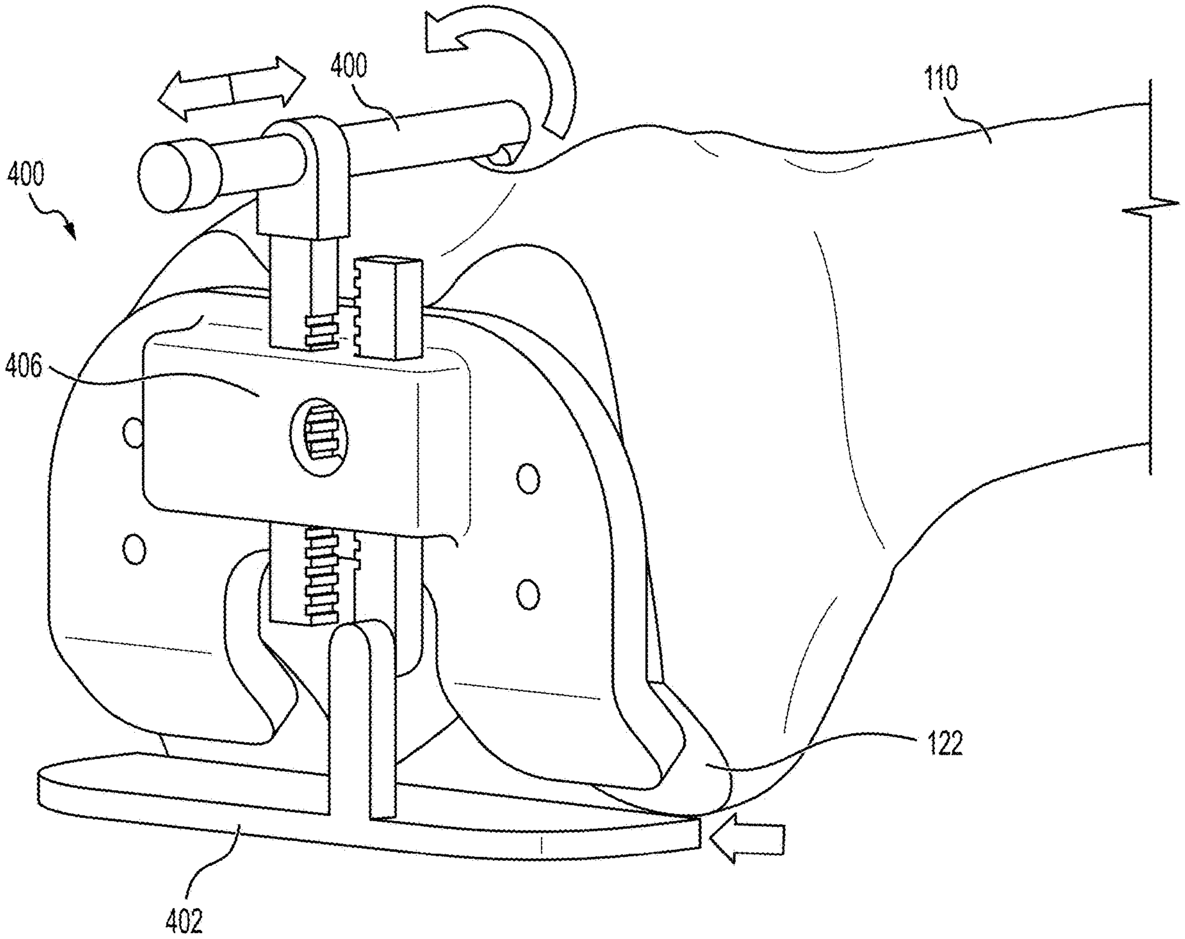
FIG. 33 is a perspective view of the anterior reference guide in use on the femur.

FIG. 31A is a perspective view of an example anterior reference guide, FIG. 31B is a lateral view of the anterior reference guide, FIG. 32 is a distal view of the anterior reference guide in use on the femur, and FIG. 33 is a perspective view of the anterior reference guide in use on the femur, all according to at least some aspects of the present disclosure. Referring to FIGS. 31A-33, if a surgeon chooses to utilize anterior referencing the following procedure may be used, such as with the knee positioned at 90 degrees of flexion. An anterior reference guide 400 with a posterior cutting plane indicator 402 is used for anterior referencing. A femoral extension cut contact surface 403 is placed against the femoral extension cut 304. Some embodiments may include a posterior chamfer cut contact surface 405, which may be placed against the posterior chamfer cut 122. An anterior stylus 404 is linked in the anterior/posterior direction with the posterior cutting plane indicator 402. As the anterior stylus 404 translates and sweeps to find the correct component size, the posterior indicator 402 will translate accordingly. For example, the guide 400 may include a mechanism 406 with opposed racks operatively connected by a rotatable pinon gear. Translation of one rack (e.g., which may be coupled to the anterior stylus 404) may cause rotation of the pinon, which may cause translation—in the opposite direction—of the other rack (e.g., which may be coupled to the posterior cutting plan indicator 402). The posterior indicator 402 shows the location of the posterior cutting plane. Once the guide 400 is properly positioned and the femoral component sized, the posterior femoral cut may be made (e.g., at 90 degrees).

Figure 34A:
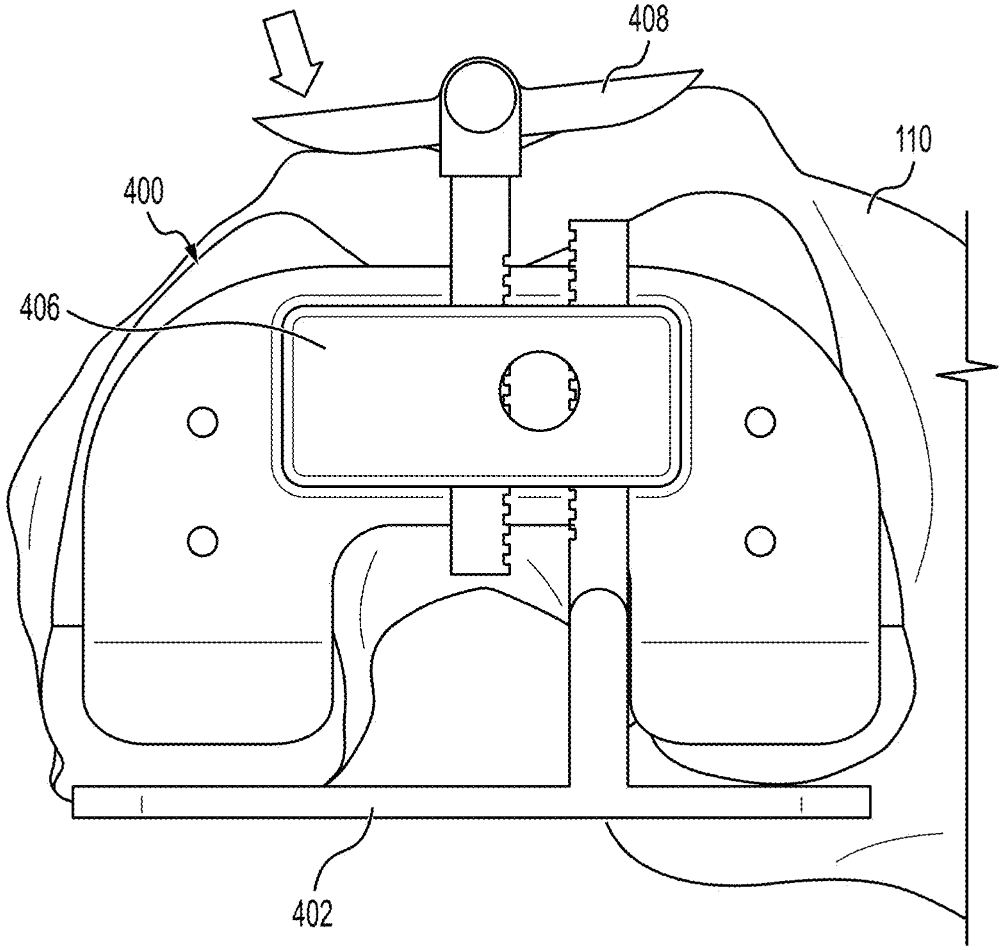
FIG. 34A is a distal view of the anterior reference guide including an alternative anterior stylus in use on the femur.
Figure 34B:
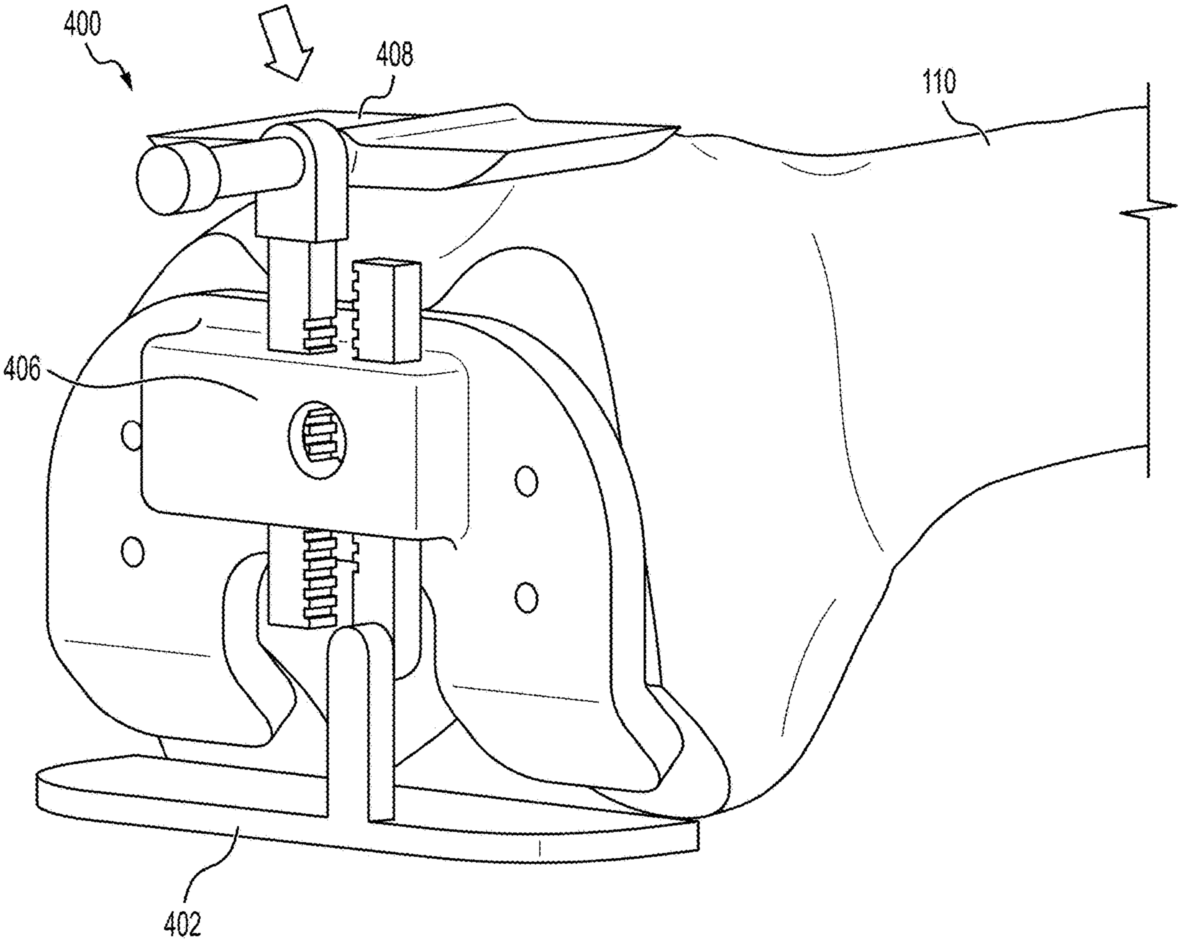
FIG. 34B is a perspective view of the anterior reference guide including the alternative anterior stylus in use on the femur.

FIG. 34A is a distal view of the anterior reference guide including an alternative anterior stylus in use on the femur, and FIG. 34B is a perspective view of the anterior reference guide including the alternative anterior stylus in use on the femur, all according to at least some aspects of the present disclosure. Referring to FIGS. 34A and 34B, alternative anterior styluses may be attached for alternative anterior referencing methods. In the illustrated embodiment, an alternative stylus 408 can be in the shape of a trough, spoon, or saucer, for example, and may be positioned in the trochlear groove. In some example methods, the shape of the trochlear groove may be derived using preoperative planning (such as using pre-operative imaging) and then this shape can be made into a patient-specific jig, which may be disposable. A patient-specific-shaped-jig may fit in the trochlear groove tightly and/or may minimize errors that may be introduced by use of a pointed stylus that could contact the trochlear groove in multiple positions. If it is not desirable to create a patient-specific, trough-like stylus using pre-operative imaging, multiple sizes and/or shapes of styluses may be provided, and such styluses could be disposable or re-used after sterilization.

Figure 35A:
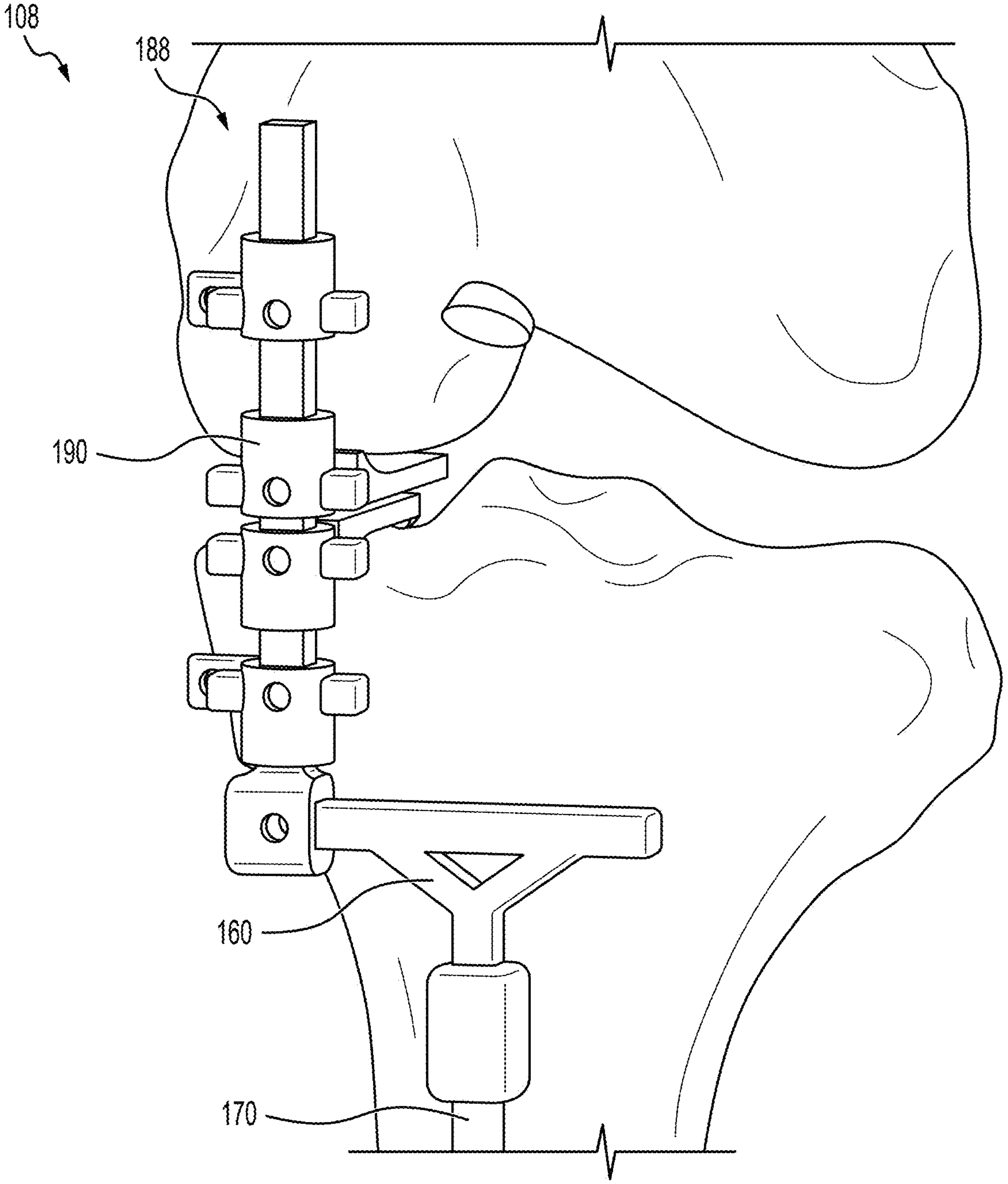
FIGS. 35A and 35B are perspective views illustrating unicompartmental use of the knee balancing jig.
Figure 35B:
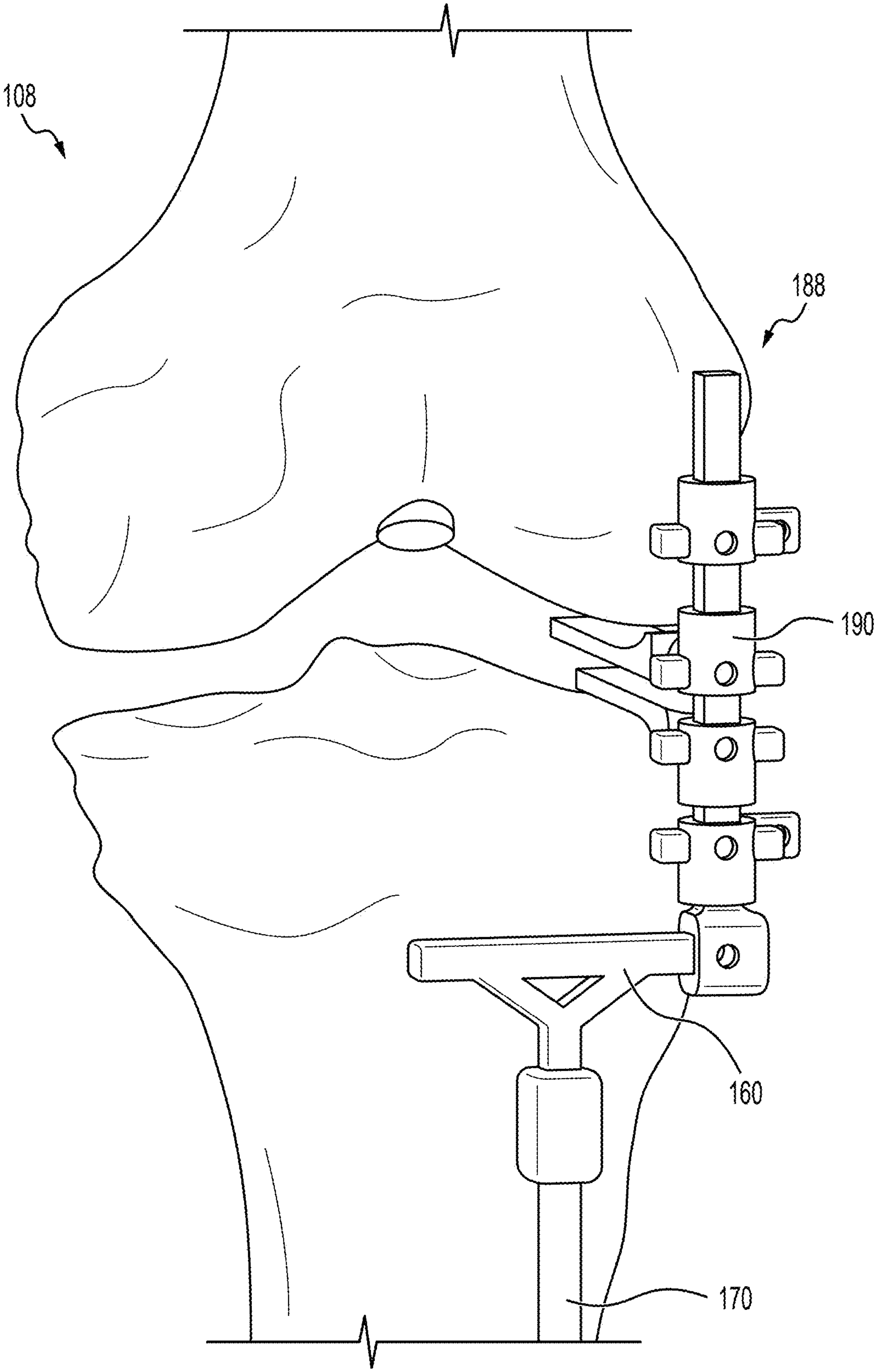

FIGS. 35A and 35B are perspective views illustrating unicompartmental use of the knee balancing jig 188. Generally, the balancing jig 188 may be used in a manner described above for TKA; however, in some circumstances, only one of the balancing assemblies 190 may be utilized in connection with the affected portion of the knee.

In some example embodiments according to at least some aspects of the present disclosure, the order in which bone cuts are made may include, without limitation, any of the following exemplary cut orders: (1) posterior chamfer cut, tibial cut, distal femoral cut, anterior chamfer and other cuts; (2) posterior chamfer cut, tibial cut, posterior femoral cut, anterior chamfer and other cuts; (3) tibial cut, posterior chamfer cut, distal femoral cut, anterior chamfer cut and other cuts; or (4) tibial cut, posterior chamfer cut, posterior femoral cut, anterior chamfer cut and other cuts.

Following from the above description, it should be apparent to those of ordinary skill in the art that, while the methods and apparatuses herein described constitute exemplary embodiments of the present invention, the invention described herein is not limited to any precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A method of preparing a body to receive a knee implant, the method comprising:

positioning a knee joint comprising a distal femur and a proximal tibia at a mid-flexion angle;

performing soft tissue balancing of the knee joint at the mid-flexion angle that includes adjusting a spacing between tibial and femoral contacts inserted between a distal femur condyle and a native proximal condyle receiver of the knee joint;

post soft tissue balancing at the mid-flexion angle, mounting a series of pins to the proximal tibia and the distal femur exhibiting at least one of a rectangle relationship and a trapezoidal relationship to the distal femur and the proximal tibia; and post mounting the series of pins, resecting at least one of the distal femur and the proximal tibia.

2. The method of claim 1, wherein positioning the knee comprising the distal femur and the proximal tibia at the mid-flexion angle includes exposing an interior of a knee capsule.

3. The method of claim 1, wherein performing soft tissue balancing of the knee at the mid-flexion angle includes inserting the tibial and femoral contacts between the distal femur and the proximal tibia and applying an expansion force to the tibial and femoral contacts to tension soft tissues of the knee.

4. The method of claim 3, wherein:

the distal femur includes a medial femoral condyle and a lateral femoral condyle;

the proximal tibia includes a medial tibial condyle receiver and a lateral tibial condyle receiver;

performing soft tissue balancing of the knee at the mid-flexion angle includes inserting a first pair of tibial and femoral contacts between the medial femoral condyle and the medial tibial condyle receiver; and performing soft tissue balancing of the knee at the mid-flexion angle includes inserting a second pair of tibial and femoral contacts between the lateral femoral condyle and the lateral tibial condyle receiver.

5. The method of claim 4, wherein mounting the series of pins includes mounting a first pair of pins to the distal femur and mounting a second pair of pins to the proximal tibia in a rectangular relationship.

6. The method of claim 5, wherein:

the first pair of pins includes a first pin and a second pin;

the first pair of tibial and femoral contacts includes a first medial femoral contact and a first medial tibial contact;

the second pair of tibial and femoral contacts includes a first lateral femoral contact and a first lateral tibial contact;

a first location where the first pin is mounted to the distal femur is determined by adding a fixed distance to a location of the first medial femoral contact when the knee is soft tissue balanced;

a second location where the second pin is mounted to the distal femur is determined by adding a fixed distance to a location of the first lateral femoral contact when the knee is soft tissue balanced.

7. The method of claim 6, wherein:

the second pair of pins includes a third pin and a fourth pin;

a third location where the third pin is mounted to the proximal tibia is determined by adding a fixed distance to a location of the first medial tibial contact when the knee is soft tissue balanced;

a fourth location where the fourth pin is mounted to the proximal tibia is determined by adding a fixed distance to a location of the first lateral tibial contact when the knee is soft tissue balanced.

8. The method of claim 4, wherein mounting the series of pins includes mounting a first pair of pins to the distal femur and mounting a second pair of pins to the proximal tibia in a trapezoidal relationship.

9. The method of claim 1, wherein performing soft tissue balancing includes tensioning soft tissues of the knee and, when tensioned, determining a gap between the distal femur and the proximal tibia at least partially occupied by the tibial and femoral contacts.

10. The method of claim 1, wherein adjusting the spacing between the tibial and femoral contacts includes wedging the tibial and femoral contacts between the distal femur and the proximal tibia.

11. The method of claim 10, wherein wedging the tibial and femoral contacts between the distal femur and the proximal tibia includes:

wedging a medial femoral contact and a medial tibial contact between medial portions of the distal femur and the proximal tibia;

wedging a lateral femoral contact and a lateral tibial contact between lateral portions of the distal femur and the proximal tibia.

12. The method of claim 11, wherein a first vertical spacing between the medial femoral contact and the medial tibial contact is independently controllable from a second vertical spacing between the lateral femoral contact and the lateral tibial contact.

13. The method of claim 1, wherein the mid-flexion angle corresponds approximately to a posterior chamfer angle of a femoral component of a knee implant.

14. The method of claim 1, wherein the mid-flexion angle is between about 30 degrees of flexion and about 70 degrees of flexion.

15. The method of claim 1, wherein the mid-flexion angle is between about 30 degrees of flexion and about 60 degrees of flexion.

16. The method of claim 1, wherein the mid-flexion angle is about 45 degrees of flexion.

17. The method of claim 1, further comprising mounting a cutting guide to at least one of the proximal tibia and the distal femur using at least one of the series of pins, wherein resecting at least one of the distal femur and the proximal tibia includes using the cutting guide to make a resection cut.

18. The method of claim 1, further comprising positioning the distal femur and the proximal tibia at a secondary angle representative of at least one of full knee extension and right angle flexion;

performing soft tissue balancing of the knee at the secondary angle that includes adjusting an ancillary spacing between the tibial and femoral contacts inserted between the distal femur and the proximal tibia;

post soft tissue balancing at the secondary angle, mounting an ancillary pin to the distal femur; and post mounting the ancillary pin, resecting the distal femur and the proximal tibia.

19. The method of claim 1, further comprising using the series of pins to establish a cutting plane with respect to at least one of the distal femur and the proximal tibia, wherein the cutting plane is used to resect at least one of the distal femur and the proximal tibia.

20. The method of claim 19, wherein using the series of pins to establish the cutting plane includes repositioning a cutting tool in parallel to a line established by the series of pins to resect at least one of the distal femur and the proximal tibia.

21. A method of preparing a body to receive a knee implant, the method comprising:

positioning a knee joint comprising a distal femur and a proximal tibia at a mid-flexion angle;

performing soft tissue balancing of the knee at the mid-flexion angle that includes adjusting a spacing between tibial and femoral contacts inserted between a distal femur condyle and a native proximal condyle receiver of the knee joint;

post soft tissue balancing at the mid-flexion angle, mounting a series of pins to the distal femur and the proximal tibia; and post mounting the series of pins, resecting the distal femur and the proximal tibia.

22. A method of preparing a body to receive a knee implant, the method comprising:

positioning a knee joint comprising a distal femur and a proximal tibia at a mid-flexion angle;

performing soft tissue balancing of the knee joint at the mid-flexion angle that includes adjusting a spacing between tibial and femoral contacts inserted between a distal femur condyle and a native proximal condyle receiver of the knee joint;

post soft tissue balancing at the mid-flexion angle, mounting a series of pins to the distal femur; and post mounting the series of pins, resecting the distal femur to create a posterior chamfer planar surface.

23. The method of claim 22, wherein performing soft tissue balancing of the knee joint at the mid-flexion angle includes inserting the tibial and femoral contacts between the distal femur and the proximal tibia and applying an expansion force to the tibial and femoral contacts to tension soft tissues of the knee joint and, when tensioned, determining a gap between the distal femur and the proximal tibia at least partially occupied by the tibial and femoral contacts.

24. The method of claim 23, wherein:

the distal femur includes a medial femoral condyle and a lateral femoral condyle;

the proximal tibia includes a medial tibial condyle receiver and a lateral tibial condyle receiver;

performing soft tissue balancing of the knee joint at the mid-flexion angle includes inserting a first pair of tibial and femoral contacts between the medial femoral condyle and the medial tibial condyle receiver; and performing soft tissue balancing of the knee joint at the mid-flexion angle includes inserting a second pair of tibial and femoral contacts between the lateral femoral condyle and the lateral tibial condyle receiver.

25. The method of claim 24, wherein:

the series of pins includes a first pin and a second pin;

the first pair of tibial and femoral contacts includes a first medial femoral contact and a first medial tibial contact;

the second pair of tibial and femoral contacts includes a first lateral femoral contact and a first lateral tibial contact;

a first location where the first pin is mounted to the distal femur is determined by adding a fixed distance to a location of the first medial femoral contact when the knee is soft tissue balanced;

a second location where the second pin is mounted to the distal femur is determined by adding a fixed distance to a location of the first lateral femoral contact when the knee is soft tissue balanced.

26. The method of claim 22, further comprising:

post soft tissue balancing at the mid-flexion angle, mounting a second series of pins to the proximal tibia; and post mounting the second series of pins, resecting the proximal tibia to create a tibial planar surface;

wherein:

performing soft tissue balancing of the knee joint at the mid-flexion angle includes inserting a first set of tibial and femoral contacts between a medial femoral condyle and a medial tibial condyle receiver, and inserting a second set of tibial and femoral contacts between a lateral femoral condyle and a lateral tibial condyle receiver;

the second series of pins includes a first tibial pin and a second tibial pin;

a first location where the first tibial pin is mounted to the proximal tibia is determined by adding a fixed distance to a location of a tibial contact of the first set of tibial femoral contacts post soft tissue balancing;

a second location where the second tibial pin is mounted to the proximal tibia is determined by adding a fixed distance to a location of a tibial contact of the second set of tibial femoral contacts post soft tissue balancing.

27. The method of claim 22, wherein:

adjusting the spacing between the tibial and femoral contacts includes wedging the tibial and femoral contacts between the distal femur and the proximal tibia;

wedging the tibial and femoral contacts between the distal femur condyle and the proximal tibia condyle receiver includes:

wedging a medial femoral contact and a medial tibial contact between a medial distal femur condyle and a medial proximal tibia condyle receiver;

wedging a lateral femoral contact and a lateral tibial contact between a lateral distal femur condyle and a lateral proximal tibia condyle receiver.

28. The method of claim 22, further comprising mounting a cutting guide to the distal femur using the series of pins, wherein resecting the distal femur includes using the cutting guide to create the posterior chamfer planar surface.

29. The method of claim 22, further comprising:

positioning the distal femur and the proximal tibia at a secondary angle representative of at least one of full knee extension and right angle flexion;

performing soft tissue balancing of the knee joint at the secondary angle that includes adjusting an ancillary spacing between the tibial and femoral contacts inserted between the distal femur and the proximal tibia;

post soft tissue balancing at the secondary angle, mounting an ancillary pin to the distal femur; and post mounting the ancillary pin, resecting at least one of the distal femur and the proximal tibia.

* * * * *